US012351873B2

(12) United States Patent
Snyder et al.

(10) Patent No.: US 12,351,873 B2
(45) Date of Patent: Jul. 8, 2025

(54) METHOD FOR TREATMENT OF HYPERTENSION

(71) Applicant: Geneticure Inc., Minnetonka, MN (US)

(72) Inventors: Eric Snyder, Rochester, MN (US); Ryan Sprissler, Tucson, AZ (US); Benjamin Bowman, St. Paul, MN (US); Scott C. Snyder, Minnetonka, MN (US)

(73) Assignee: Geneticure Inc., Minnetonka, MN (US)

( * ) Notice: Subject to any disclaimer, the term of this patent is extended or adjusted under 35 U.S.C. 154(b) by 840 days.

(21) Appl. No.: 16/956,215

(22) PCT Filed: Dec. 21, 2018

(86) PCT No.: PCT/US2018/067300

§ 371 (c)(1),
(2) Date: Jun. 19, 2020

(87) PCT Pub. No.: WO2019/126757

PCT Pub. Date: Jun. 27, 2019

(65) Prior Publication Data

US 2023/0203582 A1 Jun. 29, 2023

Related U.S. Application Data

(60) Provisional application No. 62/608,769, filed on Dec. 21, 2017.

(51) Int. Cl.
*C12Q 1/6883* (2018.01)
*C12Q 1/6858* (2018.01)

(52) U.S. Cl.
CPC ......... *C12Q 1/6883* (2013.01); *C12Q 1/6858* (2013.01); *C12Q 2600/156* (2013.01)

(58) Field of Classification Search
None
See application file for complete search history.

(56) References Cited

U.S. PATENT DOCUMENTS

2007/0092888 A1 4/2007 Diamond et al.

FOREIGN PATENT DOCUMENTS

WO WO-2015183938 A1 12/2015
WO WO-2016033543 A1 3/2016
WO WO-2019126757 A1 6/2019

OTHER PUBLICATIONS

"International Application Serial No. PCT US2018 067300, International Preliminary Report on Patentability mailed Jul. 2, 2020", 9 pgs.
"European Application Serial No. 18845334.4, Response filed Jan. 14, 21 to Communication pursuant to Rules 161(1) and 162 mailed Jul. 31, 2020", 20 pgs.
"European Application Serial No. 18845334.4, Communication Pursuant to Article 94(3) EPC mailed Jul. 22, 2021", 8 pgs.
"International Application Serial No. PCT/US2018/067300, International Search Report mailed Mar. 27, 2019", 5 pgs.
"International Application Serial No. PCT/US2018/067300, Written Opinion mailed Mar. 27, 2019", 7 pgs.
Eadon, Michael T, et al., "A Physiologic Approach to the Pharmacogenomics of Hypertension", Advances in Chronic Kidney Disease, vol. 23, No. 2, (Mar. 2016), 91-105.
Johnson, Micah William, et al., "Multi-Gene Pharmacogenetics and Blood Pressure Control in Patients with Hypertension", FASEB Journal, vol. 30, No. Suppl, (Apr. 1, 2016), 942.1.
"European Application Serial No. 18845334.4, Response Filed Jan. 18, 2022 to Communication Pursuant to Article 94(3) EPC mailed Jul. 22, 2021", 13 pgs.
"European Application Serial No. 18845334.4, Communication Pursuant to Article 94(3) EPC mailed Mar. 9, 2023", 5 pgs.
"European Application Serial No. 18845334.4, Response filed Jun. 22, 2023 to Communication Pursuant to Article 94(3) EPC mailed Mar. 9, 2023", 2 pgs.

*Primary Examiner* — Carla J Myers
(74) *Attorney, Agent, or Firm* — Schwegman Lundberg & Woessner, P.A.

(57) ABSTRACT

The present invention concerns selective renal denervation treatment of drug resistant hypertensive patients by correlating the patients' genetic panel by categorization and hierarchy according to patients' genetic variants within the functional genes for heart activity, for the renin-angiotensin aldosterone system, and for renal activity.

32 Claims, 2 Drawing Sheets

Specification includes a Sequence Listing.

METHOD FOR TREATMENT OF HYPERTENSION

PRIORITY CLAIM TO RELATED APPLICATIONS

This application is a U.S. National Stage Application under 35 U.S.C. 371 from International Application Serial No. PCT/US2018/067300, filed on Dec. 21, 2018, and published as WO 2019/126757 A1 and published on Jun. 27, 2019, which claims the benefit of priority from U.S. Provisional Patent Application Ser. No. 62/608,769, filed on Dec. 21, 2017, which are herein incorporated by reference in their entirety.

BACKGROUND OF THE INVENTION

Hypertension (high blood pressure) is one of the most important preventable contributors to disease and death in the world and represents the most common condition seen in the primary care setting (1, 2). According to the American Heart Association, approximately 78 million adults (1 in 3) living in the United States have hypertension with more than 5 million new diagnoses made each year. Of these individuals, 82% are aware they have it, 75% are currently being treated for it, but only 52% have their blood pressure under control (thus, ~48% do not have adequate blood pressure control). Hypertension is known to lead to myocardial infarction (heart attack), stroke, renal failure, and death if not detected early and treated appropriately. In fact, in 2009, high blood pressure was listed as a primary or contributing cause of death in ~350,000 of the ~2.4 million U.S. deaths (14% of all deaths). From 1999-2009 the number of deaths attributable to hypertension increased by 44%. In 2009, the direct and indirect economic burden on the United States health care system associated with hypertension was estimated at $51 billion. With the advent of improved diagnostic techniques, increased rates of health care utilization and screening, and the increasing age of the population, a continual upward trend in this expenditure is expected.

Globally, nearly 1 billion individuals have been diagnosed with hypertension with an estimate of an additional 400 million living with undiagnosed hypertension. Hypertension is the leading cause of premature death and the leading cause of cardiovascular disease worldwide. Similar to the continued upward trend in prevalence as seen in the United States, it is estimated that in 2025 1.56 billion adults will be living with hypertension.

Resistant hypertension is defined as blood pressure that remains above clinical guideline goals (typically >140/>90 mmHg) in spite of concurrent use of three antihypertensive agents of different classes, including the use of a diuretic (3). Drug resistant hypertension can be defined as hypertension that has ruled out: white coat syndrome (elevations in blood pressure in response to a visit to the clinic), incorrect blood pressure measurement (typically confirmed with a 24-hr holter monitor), incorrect treatment decisions, and lack of medication adherence. Resistant hypertension is noted in up to 20% of all hypertensive cases and contributes to high levels of morbidity and mortality (3). In addition, some patients favor hypertension intervention by means other than life long antihypertensive agent therapy. All antihypertensive drugs have inescapable side effects ranging from bronco-respiratory irritation to hepatic malconditions.

For patients with hypertension, and especially patients with resistant hypertension and those who want a hypertensive therapy not based on pharmacotherapy, renal denervation (by chemical, ultrasound, electric or heat technique) has been proposed as a critical means to control blood pressure. Renal denervation has been used in patients for more than 60 years with physiologically and clinically promising results. An initial large study in humans found dramatic differences in survival in patients who received renal denervation when compared to patients who did not (4). Resistant hypertensive patients who had renal denervation (via splanchicectomy) had 19% mortality compared to 54% mortality in the group that did not receive surgery. Interestingly, this improvement in mortality following splanchicectomy occurred regardless of the changes in blood pressure. More recent work in humans was initially promising on renal denervation and the blood pressure response in resistant hypertensives. Two small studies (Symplicity HTN-1 and Symplicity HTN-2) were performed that demonstrated dramatic reductions in blood pressure with renal denervation, when compared to no intervention (5-7). However, a large randomized and controlled study found that there were no differences in blood pressure between patients who had a sham surgery and those who actually received renal denervation (8). In many of the modern sham-controlled studies there is a significant (~30%) portion of patients who have no change, or even an increase, in blood pressure following the procedure.

Therefore, there is a need to investigate and develop techniques and methods that will enable hypertensive patients to be successfully treated by renal denervation procedures. Additional need for development include investigation and development of successful renal denervation/denervation techniques.

SUMMARY OF THE INVENTION

According to the invention, it has been discovered that sympathetic nervous system (SNS), cardiac, vascular and renal genetic characteristics of hypertensive patients can be analyzed and patients with certain SNS, cardiac, vascular and renal genetic characteristics can be selected who will exhibit a positive physiological response to renal denervation/denervation procedures. According to the invention, this discovery enables methods, devices and kits for enabling successful anti-hypertensive treatment of certain patients who undergo renal denervation procedures. More specifically, the invention relates to methods, devices, and kits for identifying hypertensive patients who will affirmatively respond to renal denervation.

The methods, devices, and kits to provide a high rate of successful renal denervation treatments for hypertensive patients by coordinating the denervation treatment with common genetic variants in the SNS, cardiac, vascular, and renal systems. The coordination matches patients with techniques for renal denervation/denervation surgery so that the matched patients will respond favorably to the surgery. According to an aspect of the inventive method, there are certain genetic variants in the SNS, cardiac, vascular, and renal systems that are physiologically important in relation to renal denervation. Based on this discovery and development, clinicians can treat patients who will positively respond to renal denervation/denervation.

A step of this method is directed to the sequencing of a hypertensive patient's genetic make-up or genetic code to provide a full genetic panel. The genetic panel provides the genetic sequences at least for the following nucleic acids irrespective of polymorphs at variable positions: ADRA2A, ADRA2C, ADRB1, ADRB2, renin, AGT, ACE, AGT1R, WNK1, ADD1, SLC12A3 and SCNN1A. The genetic panel is described further in the Detailed Description. The panel is screened to determine whether the panel contains one or more of the gene sequences of categories A, B, C and D with the specified polymorphs at the variable positions.

Category A:

1. an ADRA2A nucleic acid with a cytosine at the variable position rs2484516;
2. an ADRA2A nucleic acid with a thymine at the variable position rs553668;
3. an ADRA2C nucleic acid with a DELETION at the variable position rs13118711

Category B:

1. an ADRB1 nucleic acid with a cytosine at the variable position of rs1801253;
2. an ADRB1 nucleic acid with an adenine at the variable position of rs1801252;
3. an ADRB2 nucleic acid with a guanine at the variable position of rs1042714;
4. an ADRB2 nucleic acid with a guanine at the variable position of rs1042713;

Category C:

1. a renin nucleic acid with a thymine at the variable position of rs12750834;
2. an AGT nucleic acid with a cytosine at the variable position of rs699;
3. an AGT thymine at position rs5051;
4. an AGT guanine at rs7079;

Category D:

1. an ACE nucleic acid with a deletion in rs1799752;
2. an AGT1R nucleic acid with a cytosine at the variable position of rs5186;

Category E:

1. a WNK1 nucleic acid with a cytosine at the variable nucleic acid position of rs1159744;
2. a WNK1 nucleic acid with a cytosine at the variable position of rs2107614;
3. a WNK1 nucleic acid with a cytosine at the variable position of rs2277869
4. an ADD1 nucleic acid with a thymine at the variable position of rs4961;
5. a SLC12A3 nucleic acid with a thymine at the variable amino acid position of rs1529927;
6. a SCNN1A nucleic acid with a threonine at variable amino acid position rs2228576.

The treatment step of this method is directed to nephritic nerve denervation according to the following nine protocols. The protocols coordinate the patient's genetic panel results and the success or failure of the denervation procedure. The patient will exhibit denervation responsiveness and successful treatment for hypertension by undergoing nephritic nerve denervation or the patient will not exhibit successful treatment for hypertension by undergoing nephritic nerve denervation according to these nine protocols.

Protocol 1i) the genetic panel shows that the patient has functionality of all gene sequences of categories A, B, C, D and E, and the patient treated by nephritic nerve denervation will exhibit very high denervation responsiveness.

Protocol 1ii) the genetic panel shows that the patient has functionality of all gene sequences of categories A, B, C, and D but not in category E, and the patient treated by nephritic nerve denervation will exhibit high denervation responsiveness.

Protocol 2) the genetic panel shows that the patient has functionality of all gene sequences of categories A, B and D functionality of gene sequences C1 and C2 of category C and the patient treated by nephritic nerve denervation will exhibit moderately high denervation responsiveness.

Protocol 3) the genetic panel shows that the patient has functionality of all gene sequences of categories A, B, and D, and the patient treated by nephritic nerve denervation will exhibit moderate denervation responsiveness.

Protocol 4) the genetic panel shows that the patient has functionality of all gene sequences of categories A and D and gene sequences of B1 and B2 of category B, and the patient treated by nephritic nerve denervation will exhibit minimal denervation responsiveness.

Protocol 5) the genetic panel shows that the patient has functionality of all gene sequences of categories A and D and gene sequences B2, C1 of categories B and C respectively, and the patient treated by nephritic nerve denervation will exhibit minimal denervation responsiveness.

Protocol 6) the genetic panel shows that the patient has functionality of gene sequence B2 category B, and of all gene sequences of category D, and the patient treated by nephritic nerve denervation will exhibit minimal denervation responsiveness.

Protocol 7) the genetic panel shows that the patient has functionality of all gene sequences of category D, and the patient treated by nephritic nerve denervation will exhibit almost negligible denervation responsiveness.

Protocol 8) the genetic panel shows that the patient has functionality of gene sequence D2 of category D, and the patient treated by nephritic nerve denervation will be denervation non-responsive.

Protocol 9) the genetic panel shows that the patient has no functionality of any of the gene sequences of categories A, B, C, D, and E and the patient treated by nephritic nerve denervation will be denervation non-responsive.

For each of these Protocols, if a category is not stated as part of the Protocol, the genetic panel of the Protocol does not include that category. If some sequences of a category are stated as part of the protocol but other sequences of the same category are not stated, the genetic panel of the Protocol does not include the unstated sequences.

Preferably, the successfully treated patient will have a genetic panel of Protocol 1i, 1ii or 2. More preferably, the successfully treated patient will have a genetic panel of Protocol 1i or 1ii. Most preferably, the successfully treated patient have a genetic panel of Protocol 1i. Preferably, a patient having the genetic panel of Protocol 1i will require denervation regimen a or b below. Preferably, a patient having a genetic panel of Protocol 1ii will require denervation regimen a, b or c below. Preferably, a patient having a genetic panel of Protocol 2 or 3 will require denervation regimen a, b, c or d below. A patient having a genetic panel of Protocols 4, 5 and 6 may undergo surgical denervation, however, the rate of success will be low, relative to the other protocols and the surgical denervations needed will fall into regimen c or d below. Often but not always, a patient having a genetic panel of Protocols 4, 5 and 6 will not successfully achieve control of hypertension by treatment with denervation therapy alone. Protocols 7-9 indicate that surgical denervation will not be successful for the hypertensive patient. Additionally, if the genetic panel of a patient presents sequences other than those of Protocols 1-3 and the genetic panel does not come within any of Protocols 4-9, surgical denervation will not be successful for this hypertensive patient.

The successfully treated patient will receive at least a partial surgical denervation of the sympathetic nerves lining the nephritic arteries of one or both of the qualified patient's kidneys. The patient may be a person having hypertension who does not want to be treated by pharmacotherapy which typically is long term and usually lifetime administration of anti-hypertensive pharmaceuticals. The patient may also be a person having resistant hypertension which means the patient's blood pressure cannot be controlled by administration of anti-hypertensive pharmaceuticals.

The denervation treatments can be accomplished by a variety of techniques including but not limited to chemical technique, ultrasound technique, electric technique and heat technique. Each of these techniques involves contacting the appropriate nerve site with an agent that will disrupt nerve impulse transmission through the selected nerve. The chemical technique involves application of an appropriate amount of a chemical agent that will short circuit the nerve such as by interrupting the mylan sheath of the nerve. The ultrasound technique involves application of an appropriate decibel level of ultrasound that will short circuit the nerve such as by interrupting the mylan sheath of the nerve. The electric and heat techniques also involve application of an appropriate frequency of electric current (eg, radiofrequency) or appropriate degree of heat to short circuit the nerve. The chemical, ultrasound, electric and heat treatments may be administered once or several times in succession to accomplish denervation. While a single application of the technique at a high concentration, power, voltage or temperature is possible, multiple successive applications at the lowest concentration, power, voltage or temperature possible will avoid untoward ancillary damage to nephritic tissue. Hence, these techniques may be applied once or multiple times to the nerve site. The choice and operation will depend upon the wisdom, skill, experience and practice of the surgeon conducting the operation.

The denervation can be accomplished in an ascending degree of treatments according to the following regimen. The ascending severity of treatment results in an escalating degree of denervation from almost minor to moderate to major to essentially complete or significant denervation.

a) the surgical denervation is conducted as one to twelve, preferably one to eight, more preferably four to eight treatments along one or both nephritic arteries at the arterial distal or proximal, preferably the distal region relative to the kidney;
b) the surgical denervation is conducted as one to twelve, preferably four to twelve, more preferably eight to twelve treatments along one or both nephritic arteries at the arterial distal region relative to the kidney;
c) the surgical denervation is conducted as one to twelve, preferably two to twelve, more preferably six to twelve treatments along one of both of the nephritic arteries at the arterial proximal region relative to the kidney;
d) the surgical denervation is conducted as four to twelve, preferably eight to twelve treatments along one or both of the nephritic arteries at the arterial proximal region relative to the kidney.

Following denervation, the qualified patient optionally can be administered a lowered or minimized dose of a sympatholytic drug, β blocker drug, an Angiotensin II receptor blocker drug, or an ACE II inhibitor drug or according to the following program:

i) if the treated qualified patient's genetic panel falls into Category A, administer the sympatholytic drug;
ii) if the treated qualified patient's genetic panel falls into Category B, administer the β blocker drug;
iii) if the treated qualified patient's genetic panel falls into Category C, administer the Angiotensin II receptor blocker drug;
iv) if the treated qualified patient's genetic panel falls into Category D. administer the ACE inhibitor drug.

It is found that the successfully treated patient will also be appropriately sensitive to at least one of the anti-hypertensive drugs. However, administration of the anti-hypertensive drug is an option and not a provision for successful treatment of the patient's hypertension. The nephritic denervation of the patient alone will provide successful treatment of the patient.

DETAILED DESCRIPTION OF THE INVENTION

Figure 1:
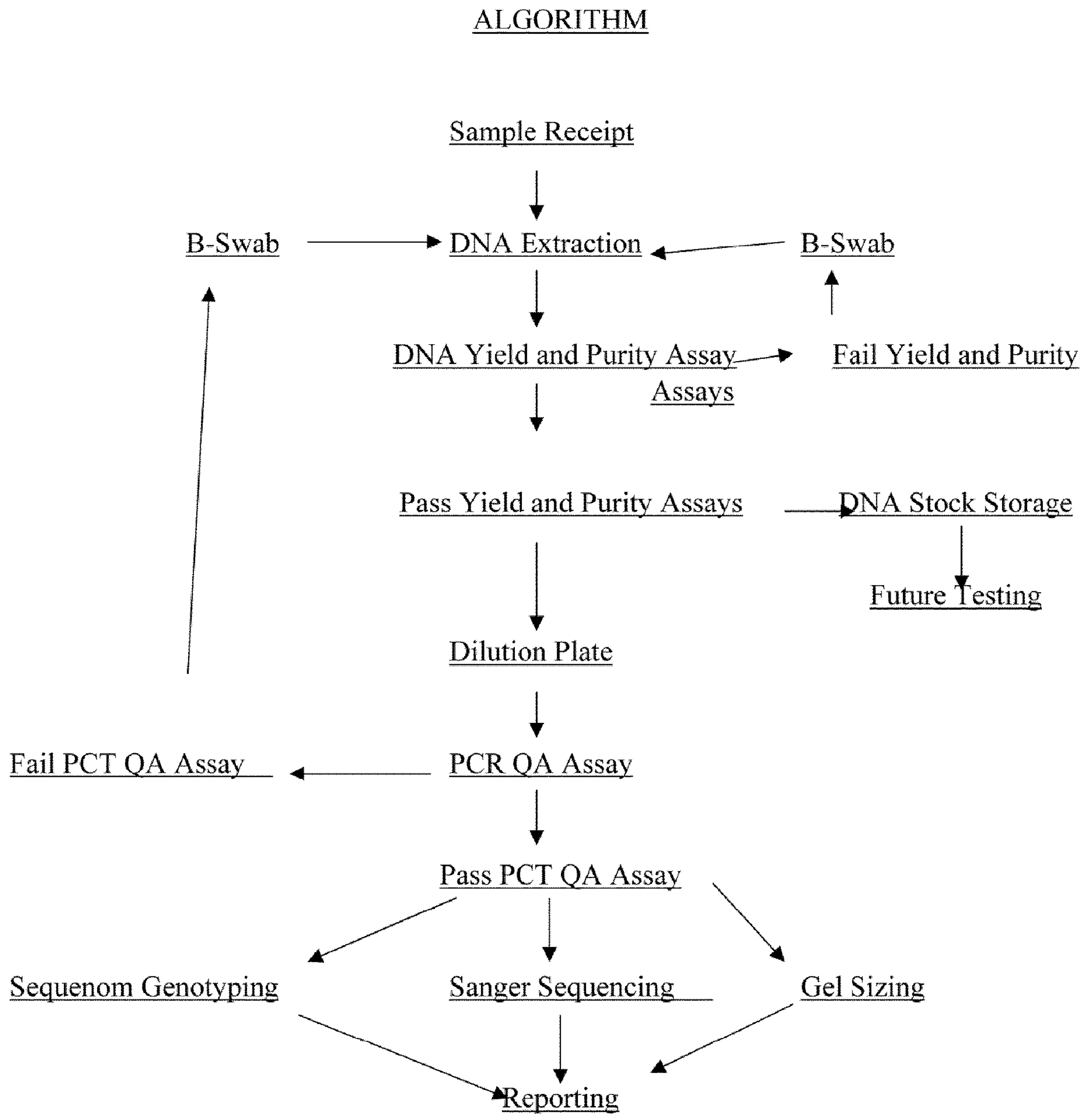
FIG. 1 is an algorithm of the process for determining the genetic panel of a patient.

Methods, devices, and kits are described herein for determining who will most likely, and least likely, respond to renal denervation/denervation surgery. The methods, devices, and kits include assays for identifying genetic variants in individual subjects that make the individual more or less responsive to this surgical intervention. Genetic variants present in genes including those in the sympathetic nervous system (SNS), heart (ADRB1 and ADRB2), those important in the renin-angiotensin aldosterone system (renin, angiotensinogen, angiotensin converting enzyme (ACE), and angiotensin receptor), and those involved in renal $Na^+$ regulation including the epithelial $Na^+$ channels (such as SCNN1A), adducin, sodium ($Na^+$) chloride ($Cl^-$) co-transporters (such as SLC12A3), and/or WNK1 genes. Investigations in humans and animals have demonstrated variable blood pressures according to these genetic variants at rest, with stress, and in response to pharmacologic interventions.

The Discovery

The development of high blood pressure in humans is the result of one or more of three physiologic mechanisms: 1) elevated cardiac output (liters of blood ejected from the heart per minute) which increases the amount of blood pressing against the vessels, 2) relatively narrow blood vessels (for a given cardiac output or plasma volume) which results in increased pressure towards the lumen of the blood vessel, or 3) increased sodium ($Na^+$) absorption in the kidney which results in increased blood volume and subsequently increased outward pressure against the tubes (vessels). Blood pressure therapy following diagnosis is traditionally based on an algorithm as suggested by the joint national committee of the American Heart Association and the American College of Cardiology(2). Typically, a patient who has been diagnosed with high blood pressure starts on a diuretic (to reduce renal $Na^+$ reabsorption), if that does not work within a period of time, then the clinician next assesses the effectiveness of a vasodilator, and if this is not effective then a clinician will lastly assess the effectiveness of a beta-blocker. Despite a strong history of research in each of these drug classes, there is significant variability in the drug response to therapy, which can become frustrating for the patient.

Drug resistant hypertension is defined as hypertension (typically >140/>90 mmHg) despite treatment with three different anti-hypertensive classes, including a diuretic (3). For true resistant hypertension it must be determined that the hypertension is not the result of white coat syndrome (high blood pressure in response to a visit to the clinic), poor blood pressure measurement, incorrect treatment decisions, or poor medication adherence (5). Drug resistant hypertension occurs in up to 20% of hypertensive individuals. Resistant hypertension results in dramatic increases in death from all cause, cardiovascular disease, and stroke (3, 9).

Renal denervation (or denervation) has been used in animal models and in humans for more than 60 years to reduce blood pressure in patients with resistant hypertension. Renal denervation reduces the signaling (and/or activity) of the sympathetic nerves of the kidney. This is typically a catheter-based radiofrequency or ultrasound denervation procedure through the renal artery and results in both efferent and afferent sympathetic signaling (10). For this denervation procedure, a catheter with a denervation tool is introduced through the femoral artery. The renal arteries are then treated through the walls of the renal artery with energy applied to the arterial walls. Multiple denervations are performed with renal denervation typically using several different locations in order to ensure maximal denervation. More recent techniques include use of ultrasound or chemical treatment to denervate the sympathetic nerves. Regardless of the denervation technique, this procedure reduces norepinephrine (NE) content within the kidney as well as norepinephrine spillover (10, 11). Previous studies have demonstrated that the more sites that are treated, and the closer to the denervation sites are to the renal pelvis, the greater the drop in NE (10). Early work demonstrated dramatic differences in survival in patients receiving renal denervation-like surgery, vs. those who did not, in a population of resistant hypertensives (4). Resistant hypertensive patients who underwent thoracolumbar splanchnicectomy had a 54% reduction in mortality over five years, when compared to patients who did not receive the procedure. This difference in mortality was present regardless of changes in blood pressure.

More recently, modern surgical devices have been developed to partially ablate the renal nerve in an attempt to control resistant hypertension. The first modern trial on one of these devices, Symplicity HTN-1, was performed on 150 individuals and resulted in substantial reductions in blood pressure for up to three years following the procedure. The average drop in systolic and diastolic blood pressures following renal denervation in Symplicity HTN-1 were 32 mmHg and 12 mmHg, respectively (compared to no relative change in blood pressure in a control group). Following this initial study, a second trial (Symplicity HTN-2) was performed in which the patients who initially did not receive the renal denervation surgery were allowed to opt-in to the procedure at the 6-month time point for long-term comparison (n=~90 total). In both groups (those who had the procedure performed initially and those who had the procedure performed after six months) blood pressure dropped dramatically (~30 mmHg for systolic blood pressure and ~10 mmHg for diastolic blood pressure) (7). These patients also had a reduction in use of renin inhibitors, ACE-inhibitors, and beta-blockers following renal denervation surgery (7). These changes (drops) in blood pressure persisted to three years post intervention where the average change from baseline was −32.7 mmHg and −13.6 mmHg for systolic and diastolic blood pressures, respectively.

However, in a controlled, well-regulated trial, Symplicity HTN-3, using a surgical control group that received sham surgery, the investigators demonstrated no difference in blood pressure between those patients who had the sham surgery and those who received renal denervation surgery (2). This finding has been attributed to number of users (more surgeons in the larger final trial) and to the sham control.

According to the invention, it has now been discovered that the differences among the various patients of Symplicity's HTN-1-3 clinical trials are attributable to genetic variation of genes encoding for the heart, renin-angiotensin aldosterone system, and for renal $Na^+$ handling of the patients treated.

TABLE 1

Renal Denervation Compared to Pharmacologic Intervention

| RDx | B-Blockade | Renin Supression | ACE-Inhibition | References |
|---|---|---|---|---|
| Improves Cardiac Fx: Decreases LVH and improved LV fx {EF, end systolic vs end-diastolic volumes, Ca+ signalling) | x | x | x | Watanabe 2016 Hyperten Res.; Pinkham 2017; Klaber Br. H. J. 1992; Lee, 1983, J Hypertens. |
| Increases (restores) B1AR and B2AR expression levels | x | | | Watanabe 2016 Hyperten Res.; Zhang 2015 Sci. Report.; Li 2015, phys res.; Karliner 1989; |
| Supress renin, ACE, and ANG-II mRNA in HF and fibrosis models | x (renin) | x | ↑renin, unless B-blocker used, ↓ANG-II | Watanabe 2016 Hyperten Res.; Zhang 2015 Sci. Report.; Li, Ox. Med. Cell, 2016; Meier, J. Mol Med, 1981 |
| Decreases catecholamine levels, SNS, MSNA | x | | | Zhang 2015 Sci. Report |

Renal denervation acts most like a sympatholytic, β-blocker, ACE-inhibitor, angiotensin-II receptor blocker and then a diuretic. Renal denervation decreases catecholamine levels within the kidney as well as catecholamine spillover and increases the expression of $\beta_1$ and $\beta_2$-adrenergic receptors in the heart (which is a similar response to β-blockade and demonstrates the importance of these receptors in renal denervation/denervation procedures). In heart failure models, renal denervation improves cardiac function, decreases left-ventricular hypertrophy, and improves left-ventricular function (similar to β-blockade response). Renal denervation also decreases the expression (mRNA) of renin, ACE and Angiotensin-II receptors (demonstrating the importance of the renin-angiotensin aldosterone system on renal denervation/denervation). According to the invention, these factors indicate that genetics provides a means for determining and categorizing very high responders, moderately high responders, moderate responders, minimal responders and non-responders to renal denervation surgery.

Scientific literature has focused on genes that encode for proteins that alter the blood pressure response to therapy based on their known protein function in the heart, blood vessels, and kidneys. Until the present invention, however, there has not been any correlation between such genes, the proteins they encode and degrees of success or failure of kidney nerve denervations. According to the present invention, certain blood pressure genetic panels encompass genes that encode for proteins affecting hypertension and can be correlated with a differential response to renal denervation surgery. This correlation is coupled with the identification of genes that have a greater or lesser response to pharmacotherapy, within the cardiac, vascular, and renal systems in humans. According to the invention, the correlation and coupling translate to a graded response to renal denervation therapy.

Response According to Genetic Variants of the Renin-Angiotensin Aldosterone System, the Cardiac System, and the Renal System Although it is not a limitation or guideline of the invention, the functional organ systems having some relation to the renal denervation/denervation procedures are: a) first, sympathetic nervous system, b) second, the cardiac system, c) third, the renin-angiotensin aldosterone system, and, d) finally, the renal system. The genes associated with the SNS, cardiac, renin-angiotensin aldosterone system, and renal system affect the results of renal denervation in a graded, categorized manner. According to the invention, a patient who likely will most respond to renal denervation surgery is one who has certain genetic functionalities in the SNS, the cardiac, renin-angiotensin aldosterone system, AND the renal system (table 3). According to the invention, the patient who will likely have a high to moderate response is one that has certain functionalities in the SNS, cardiac, and renin-angiotensin aldosterone system. According to the invention, the patient who likely will moderately respond is one who has certain functionalities of genes encoding for the cardiac AND renin-angiotensin aldosterone system, even in the absence of functionality in the renal system. According to the invention, a patient with certain genetic functionalities in the renin-angiotensin aldosterone system but not the SNS, cardiac or renal systems will have a small response to renal denervation/denervation surgery. According to the invention, a patient with no certain functionalities of the genes in any of these organ systems that are indicative of a positive response are not likely to respond to renal denervation surgery. In this context, the graded response is likely rather than guaranteed because of the idiosyncrasies of individual patients and the variation of surgical techniques practiced by nephritic surgeons.

These response levels and the certain genetic functionalities are summarized above in the Summary of the Invention section. Further details of these aspects of the invention and its embodiments are described in the following sections.

The SNS, cardiac system, renin-angiotensin aldosterone (vascular) system, and the renal system are associated with certain functional genes of the human genome. These genes are designated by acronyms known in the field. These acronyms stand for these functional genes comprising nucleic acids, i.e., nucleotide polymers of deoxyribose, phosphate and a base including adenine (A), thymine (T), guanine (G) and cytosine (C). The acronyms include:

1) ADRA2A nucleic acid associated with the amount of neurotransmitter released within the sympathetic nervous system
2) ADRA2C nucleic acid associated with the amount of neurotransmitter released within the sympathetic nervous system
3) ADRB1 nucleic acid associated with the adrenergic receptors influencing cardiac rate and contractility;
4) ADRB2 nucleic acid associated with the adrenergic receptors influencing cardiac rate and contractility;
5) AGT nucleic acid associated with angiotensinogen influencing vascular dilation and constriction;
6) Renin nucleic acid associated with renin which influences vascular constriction;
7) ACE nucleic acid associated with angiotensin converting enzyme and angiotensin-II receptors influencing vascular dilation and constriction;
8) AGT1R (AII) nucleic acid associated with angiotensin II receptors influencing vascular dilation and constriction;
9) WNK1 nucleic acid associated with blood pressure response to drugs;
10) ADD1 nucleic acid associated with alpha adducin influencing salt sensitivity (renal);
11) SLC12A3 nucleic acid associated with the sodium chloride co-transporter (renal) influencing salt retention and excretion;
12) SCNN1A nucleic acid associated with the epithelial sodium channel influencing sodium transport by the kidney (renal).

A patient's DNA is isolated and sequenced as described below to provide genetic panel of at least the foregoing nucleic acid sequences of these functional genes. These nucleic acids (functional genes) have within their full sequences reference sequences (rs's) which contain the single nucleotide polymorphisms (SNP's). The genetic panel is determined irrespective of whether or not a particular polymorphic variation of the functional gene is present.

Nevertheless, the polymorphic variations are included in the genetic panel analysis. The polymorphic variations are typical, common, ordinary single nucleic acid variations that are found in the wild type genetic sequences of humans. In relation to the denervation/denervation treatment, the SNP's within the rs's constitute the sequence variations of these functional genes that increase or decrease the responsiveness to nephritic nerve denervation. The functional genes (as described above), associated rs's, SNP's and citations providing the actual sequences and polymorphisms are as follows. The functional genes described above by known, publicly recognized acronyms are all known, publicly available sequences accessible at the US National Center for Biotechnology Information (NCBI) which is part of the United Stated National Library of Medicine (NLM), a branch of the United State National Institutes of Health (NIH).

ADRA1A-rs2484516—ncbi.nlm.nih.gov/projects/SNP/snp_ref.cgi?rs=2484516

ADRA1A-rs553668—ncbi.nlm.nih.gov/projects/SNP/snp_ref.cgi?rs=553668

ADRA2C-rs13118711—ncbi.nlm.nih.gov/projects/SNP/snp_ref.cgi?rs=13118711

ADRB1-rs1801252—ncbi.nlm.nih.gov/projects/SNP/snp_ref.cgi?rs=1801252

ADRB1-rs1801253—ncbi.nlm.nih.gov/projects/SNP/snp_ref.cgi?rs=1801253

ADRB2-rs1042713—ncbi.nlm.nih.gov/projects/SNP/snp_ref.cgi?rs=1042713

ADRB2-rs1042714—ncbi.nlm.nih.gov/projects/SNP/snp_ref.cgi?rs=1042714

WNK1-rs1159744—ncbi.nlm.nih.gov/projects/SNP/snp_ref.cgi?rs=1159744

WNK1-rs2106714—ncbi.nlm.nih.gov/projects/SNP/snp_ref.cgi?rs=2107614

WNK1-2277869—ncbi.nlm.nih.gov/projects/SNP/snp_ref.cgi?rs=2277869

Alpha adducin-rs4961—ncbi.nlm.nih.gov/projects/SNP/snp_ref.cgi?rs=4961

AGT-rs699—ncbi.nlm.nih.gov/projects/SNP/snp_ref.cgi?rs=699

AGT-rs7079—ncbi.nlm.nih.gov/projects/SNP/snp_ref.cgi?rs=7079

ACE-rs1799752—ncbi.nlm.nih.gov/projects/SNP/snp_ref.cgi?rs=1799752

AII (AGT1R)-rs5186—ncbi.nlm.nih.gov/projects/SNP/snp_ref.cgi?rs=5186

AGT-rs5051—ncbi.nlm.nih.gov/projects/SNP/snp_ref.cgi?rs=5051

SLC12A3-rs1529927—ncbi.nlm.nih.gov/projects/SNP/snp_ref.cgi?rs=1529927

SCNN1A-rs2228576—www.ncbi.nlm.nih.gov/projects/SNP/snp_ref.cgi?rs=2228576

Renin-rs12750834—ncbi.nlm.nih.gov/projects/SNP/snp_ref.cgi?rs=12750834

Table 3 presents a summary of these function genes, the rs numbers, the SNP variants and the functions. These functional genes are described and sequences as SEQ ID NO's are given at the end of this specification.

and 95% of the sino-atrial (SA) node (which controls heart rate). Although heart rate and cardiac contractility are primarily regulated by the $\beta_1$AR, the beta-2 adrenergic receptors ($\beta_2$AR) also play a role, primarily in cardiac contractility. Stimulation of either the $\beta_1$AR or the $\beta_2$AR influences heart rate and cardiac contractility through increases in intracellular c-AMP and protein kinase A (PKA) which alter $Ca^+$-channel sensitivity and decreases the threshold needed for an action potential. Therefore, cardiac output (and, in response, blood pressure) is increased through active $\beta_1$AR or $\beta_2$ARs (therefore, if a gene that encodes the $\beta_1$AR or $\beta_2$AR results in a more functional receptor, cardiac output is increased) responding to SNS stimulation.

The evidence for the importance of the $\beta_1$AR and $\beta_2$AR is demonstrated through the use of selective (i.e. atenolol and metoprolol) and non-selective (i.e. propranolol and carvedilol) beta-blockers (selective meaning they are selective for inhibiting the BAR and non-selective meaning they inhibit both $\beta_1$AR and $\beta_2$AR) which decrease blood pressure through a decrease in heart rate and cardiac contractility. Patients with hypertension often have an augmented sympathetic drive (which is why renal denervation will be of benefit to these patients, according to this invention) and β-blockade can help to attenuate this elevation in sympathetic nervous system activity. Work in animal models has demonstrated that renal denervation reduces the amount of catecholamines circulating in the blood and restores the functionality of the $\beta_1$ and $\beta_2$-adrenergic receptors. This is

TABLE 3

Functional Importance of Genes Used to Indicate Positive Response to Renal Denervation Surgery Function

| Organ System | Gene/Variant | rs# | Function |
|---|---|---|---|
| Sympathetic | ADRA2A | 2484516 | NE release |
| Tone | ADRA2A | 553668 | NE release SNS response to stress |
| | ADRA2C Del | 13118711 | NE release SNS response to stress |
| Heart (Cardiac | ADRB2_16 | 1042713 | Receptor density on vasculature and heart, differences in agonist-mediated desensitization |
| Output) | ADRB2_27 | 1042714 | Receptor density on vasculature and heart, differences in agonist-mediated desensitization |
| | ADRB1_49 | 1801252 | Cardiac output and HR response to stimulation, response to B-blockade |
| | ADRB1_389 | 1801253 | Cardiac output and HR response to stimulation, response to B-blockade |
| Kidney (Na+ regulation: | Alpha Adducin | 4961 | Alpha subunit of adducin: Adducin regulates $Ca^{++}$/calmodulin protein enzymes and is associated with hypertension, diuretic respons |
| plasma volume) | SCNN1A | 2228576 | Alpha subunit of the Epithelial $Na^+$ Channel: regulates $Na^+$ reabsorption in the kidney, hypertension |
| | SLC12A3 (2) | 1529927 | $Na^+/Cl^-$ Cotransporter: important in $Na^+/Cl^-$ reabsorption in the kidney |
| | WNK1(a) | 1159744 | Serine/Threonine-protein kinase: regulates $Na^+$ co-transporters (i.e. SLC12A3) and, therefore, $Na^+$ reabsorption, response to diuretic |
| | WNK1(b) | 2107614 | Serine/Threonine-protein kinase: regulates $Na^+$ co-transporters (i.e. SLC12A3) and, therefore, $Na^+$ reabsorption, response to diuretic |
| | WNK1(c) | 2277869 | Serine/Threonine-protein kinase: regulates $Na^+$ co-transporters (i.e. SLC12A3) and, therefore, $Na^+$ reabsorption, response to diuretic |
| Vessels (vascular | Renin | 12750834 | Renin: converts angiotensinogen to angiotensin-I, differentially influences renin levels and hypertension |
| dilation/ | Angiotensin | 5051 | Angiotensin-I: pre-curser to angiotensin-II, differential response to ACE-inhibition, ARB |
| constriction) | Angiotensin | 699 | Angiotensin-I: pre-curser to angiotensin-II, differential response to ACE-inhibition, ARB |
| | Angiotensin | 7079 | Angiotensin-I: pre-curser to angiotensin-II, predicts response to ACE inhibition |
| | ACE | 1799752 | Angiotensin Convertin Enzyme: Important in the conversion of angiotensin-I to angiotensin-II and, therefore, vascular function |
| | All Receptor | 5186 | Angiotensin-Receptor: binds to angiotensin-II and causes vasoconstriction and $Na^+$ reabsorption |

Cardiac Output

Proteins Important in Cardiac Function

Cardiac output is the amount of blood that is pumped out of the heart per minute and is the product of heart rate (the number of times the heart beats per minute) and stroke volume (SV, the amount of blood ejected from the heart per beat). There are two primary receptors within the heart that influence both rate (chronotropic effect) and contractility (inotropic effect) in response to elevations in sympathetic nervous tone. The heart is primary comprised of beta-1 adrenergic receptors ($\beta_1$AR) which are located on 80% of the ventricular wall surface, 70% of the atrial wall surface, the same effect that a patient with elevated adrenergic drive who is on a β-blocker would experience. Thus, both the $\beta_1$AR and the $\beta_2$AR are important in the regulation of cardiac output, and the response to sympathetic nervous system modulation (i.e. renal denervation) with the end result of stimulation of these receptors (or more functional receptors due to genetic variation) being elevations in cardiac output (which increases blood pressure). Despite the blood pressure reducing effects of both selective and non-selective beta-adrenergic blockade, not all individuals respond similarly to beta-blockade, despite similar clinical and environmental conditions. This difference in pharmacodynamic reaction to beta blockade indicates a genetic relation to effectiveness of this class of drugs. According to the invention, this relation can be mirrored with renal denervation responses.

Functional Effects of Genes that Encode Proteins that Influence Sympathetic Nervous System Activity and Cardiac Function There are common and functional alleles of both the alpha-2A and alpha-2C adrenergic receptors that have demonstrated differences in catecholamine and sympathetic response to stimulation. Specifically, the DD variant of the ADRA2C (rs13118711) demonstrates a greater increase in HR, when compared to the II, and ID variants (47, 48). Further, the D variant demonstrates a greater reduction in norepinephrine levels with 3-months of treatment with Bucindolol, when compared to the I variant (49). A functional variant of the ADRA2A (rs553668) has demonstrated differential BP responses to dexmedetomidine (50) and a functional variant of this gene at a different site (rs2484516) is associated with differential levels of fasting insulin and the insulin response to dexmedetomidine (which can be reflective of SNS activity) (51).

The genes that encode both the BAR (the gene that encodes this receptor is the ADRB1) and $\beta_2$AR (the gene that encodes this receptor is the ADRB2) have several functional polymorphisms. These common functional variants alter the protein function, as well as the response to therapy in cell models, animal models, and in human models. Specifically, genetic variation of the ADRB1 at positions 49 (arginine to glycine substitution, rs1801252) and 389 (serine to glycine substitution, rs1801253) influence protein function and response to beta-blockade in humans (see table 4 below). Individuals with the Arg389 polymorphism of ADRB1 have higher resting blood pressure values, greater left-ventricular mass (which is an adaptation to prolonged elevations in blood pressure) and have a greater response to beta-blockade. Individuals with the Ser49 polymorphism of the have higher resting heart rate and blood pressure values and are, therefore, more responsive to a beta-blocker.

Within the gene that encodes the ADRB2, amino acids 16 and 27 have common functional variants with the glycine polymorphism at position 16 being more prevalent in hypertensives and people with this variant demonstrating higher resting stroke volume and cardiac output. In addition, the arginine variant at position 16 of the ADRB2 has higher levels of mortality following beta-blockade after acute coronary syndrome. The glutamine variant at amino acid 27 of the ADRB2 (Glu27) is more prevalent in patients with hypertension.

To summarize: according to this invention, the functional consequences of genetic variation of ADRB1, and ADRB2 in part will determine the response effectiveness of renal denervation in patients with hypertension, especially when considered in conjunction with the functional variants of the renin-angiotensin aldosterone system.

TABLE 4

Genetic Variants of the SNS, ADRB1, and ADRB2 and Predictive Response to Renal Denervation

| Organ System | Gene/Variant | rs# | Importance in Renal Denervation |
|---|---|---|---|
| Sympathetic Tone | ADRA2A | 2484516 | High |
| | ADRA2A | 553668 | Very High |
| | ADRA2C Del | 13118711 | Extremely High |
| Heart (Cardiac Output) | ADRB2_16 | 1042713 | High |
| | ADRB2_27 | 1042714 | High |
| | ADRB1_49 | 1801252 | Extremely High |
| | ADRB1_389 | 1801253 | Extremely High |

Renin-Angiotensin Aldosterone System

Dilation of blood vessels results in decreases in blood pressure, whereas constriction of blood vessels results in increases in blood pressure. The blood vessels are controlled through local neural signaling (parasympathetic control) as well as circulating hormones (sympathetic control) and other circulating proteins. According to the present invention, blood pressure increases with elevations in sympathetic drive, which can be attenuated with renal denervation/denervation. The angiotensin receptors are stimulated by angiotensin II which is converted from angiotensin I through the angiotensin converting enzyme (ACE). Angiotensin II is a potent vasoconstrictor and actively acts to inhibit bradykinin which is a potent vasodilator, having a dual role in vasoconstriction. Therefore, a common target of blood pressure therapy through promotion of vasodilation is through the inhibition of the activity of ACE (i.e. ACE inhibitors), which reduces the bioavailability of angiotensin-II. Similarly, angiotensin-II receptor antagonists work through the competitive inhibition of the angiotensin-II receptors which decreases the number of receptors that are available to bind to angiotensin-II.

Functional Effects of Genes that Encode Proteins that Influence Vascular Function Several common and functional polymorphisms of the genes that encode for ACE and A-II receptors have been described. These genetic alter protein function, as well as the response to drug therapies in cell models, animal models, and human models (table 5). Within the gene that encodes ACE, there is one known common and functional polymorphism (rs1799752), an insertion or deletion polymorphism of a 287 base pair fragment. The deletion polymorphism of ACE results in higher plasma levels of ACE and a greater drop in ejection fraction in patients following MI. In addition, patients with the deletion polymorphism have left-ventricular hypertrophy at higher rates when compared to patients with the insertion polymorphism (left-ventricular hypertrophy results secondary to prolonged exposure to high blood pressure). Therefore, according to the invention, the deletion polymorphism would provide a response to renal denervation.

At least three functional variants of angiotensin have been found to be common in humans (rs5051, rs699, and rs7079). Functional polymorphisms of angiotensin results in higher angiotensin levels and higher resting blood pressure values. Therefore, according to the invention, patients with these genetic variants will benefit more from renal denervation due to a greater effect on the blunting of ACE and the angiotensin-II receptor.

A common functional polymorphism of an angiotensin receptor (type-I) has been described (rs5186) and influences resting blood pressure values and demonstrates which patients will benefit more from renal denervation due to attenuation of angiotensin-II expression. Specifically, patients with the C variant of the angiotensin receptor type I have higher resting blood pressure values, more detrimental cardiovascular events, and have a greater chance of developing high blood pressure during pregnancy, when compared to the A variant. Collectively, according to the invention, the C variant will be more responsive to renal denervation.

In addition to angiotensin, angiotensin II receptors and ACE, renin has been shown to be a potent vasoconstrictor that can result in high blood pressure. Renin converts angiotensinogen to angiotensin I which results in vasoconstriction due to the down-stream effects (angiotensin-I conversion to angiotensin II through ACE). There is one functional and common polymorphism of renin that demonstrates an altered blood pressure response to vasodilator therapy, a cytosine to threonine substitution at nucleotide 5312 (rs12750834). Within this polymorphism of renin, the thymine substitution and the heterozygous condition demonstrate higher renin levels as well as a greater reduction in blood pressure in response to valsartan (which is an angiotensin II receptor blocker). Given that renal denervation surgery results in attenuation of ACE and the angiotensin-II receptor, according to this invention, this same variant (thymine) of renin will be one that responds better to renal denervation therapy.

To summarize: according to the invention, the renin-angiotensin aldosterone system is the most important system to predict the response to renal denervation surgery. The three most important genes are likely renin+ACE+angiotensin-II receptor. Additional guidance will come from functional variants of angiotensin.

TABLE 5

Genetic Variation of the Renin-Angiotensin Aldosterone System and Predictive Response to Renal Denervation

| Organ System | Gene/Variant | rs# | Importance in Renal Denervation |
|---|---|---|---|
| Vessels (vascular dilation/ constriction) | Renin | 12750834 | Extremely High |
| | Angiotensin | 5051 | High |
| | Angiotensin | 699 | High |
| | Angiotensin | 7079 | High |
| | ACE | 1799752 | Extremely High |
| | All Receptor | 5186 | Extremely High |

Sodium ($Na^+$) Reabsorption in the Kidney

Proteins Important in Renal $Na^+$ Reabsorption

Many consider the kidneys to be the center of long-term blood pressure regulation. Alterations in $Na^+$ reabsorption in the kidneys result in alterations in fluid retention, which leads to increases or decreases in blood plasma volume and changes the pressure against the vessels. According to the present invention, there are several proteins that are important in renal $Na^+$ handling and the response to diuretic therapy including the epithelial $Na^+$ channels (SCNN1A, rs2228576), alpha-adducin (rs4961), the $Na^+Cl^-$ co-transporter (rs159927), and lysine deficient protein kinase-1 (WNK, rs1159744, rs2106714, and rs2277869). The epithelial sodium ($Na^+$) channel is responsible for $Na^+$ reabsorption on the apical portion of epithelial cells in the kidneys. The $Na^+$ channel is made up of three different subunits; the alpha, beta, and gamma. The alpha subunit of the epithelial $Na^+$ channel is highly functional and removal of this subunit abolishes channel activity in cell and animal models. The gamma subunit is also extremely important in channel function and functional genetic variants of this channel result in pseudohypoaldosteronism type-I and Liddle's syndrome, two severe genetic diseases resulting in salt wasting and high salt conservation (salt sensitivity), respectively. Adducin is made up of an alpha, beta, and gamma subunit. The alpha subunit of adducin increases sodium ($Na^+$) reabsorption in the kidneys through activity of $Na^+K^+$ ATPase (which moves $Na^+$ and potassium into out of cells). The sodium ($Na^+$) chloride ($Cl^-$) co-transporter is important in regulating $Na^+$ and $Cl^-$ movement between the kidney and the rest of the body. Active $Na^+$—$Cl^-$ transport results in $Na^+$ reabsorption and, therefore, results in higher blood pressure. The WNK1 protein is a key regulator of long-term $Na^+$ and chloride $Cl^-$ reabsorption in the kidneys. WNK1 regulates the activity of $Na^+$—$Cl^-$ co-transporters. If a patient has a more active WNK1 genotype, they have greater $Na^+$ and $Cl^-$ reabsorption in the kidneys which increases blood volume and, therefore, the pressure on the vessels.

Increases in the activity of the proteins important in renal $Na^+$ and $Cl^-$ regulation according to this invention result in increases in $Na^+$ retention and elevations in blood pressure. According to the invention, these genetic variations also enable a greater response renal denervation, when considered in the presence of functional variants of the renin-angiotensin aldosterone system and the cardiac system.

Functional Effects of Genes that Encode Proteins that Influence Renal $Na^+$ Reabsorption A functional and common polymorphism of the gene that encodes the epithelial $Na^+$ channel (SCNN1A) has been identified (alanine to threonine substitution at position 663) (table 6). Patients with the threonine substitution of SCNN1A have more functional $Na^+$ channels (higher activity and higher voltage currents across the cells) and are more susceptible to hypertension. Common and functional genetic variation of alpha adducin has also been identified (glycine to tryptophan substitution at amino acid 460). Within alpha adducin, individuals with the tryptophan variant are more likely to be salt sensitive, have higher rates of hypertension and have demonstrated a greater response to a diuretic. Genetic variation of the sodium ($Na^+$) chloride ($Cl^-$) co-transporter (SLC12A3) also demonstrates functional consequences. Within the SLC12A3, patients with the alanine variant have a better response to loop diuretics and demonstrate more excretion of $Cl^-$ and $K^+$ in response to diuretic therapy. Patients with the cytosine variant of WNK at genes rs1159744 and rs2107614 have greater blood pressure reductions in response to diuretic therapy when compared to patients with the glycine or threonine variants at these two sites, respectively.

To Summarize: According to the invention, hypertensive patients with a functional polymorphism of the SCNN1A (threonine 663) variant), ADD1 (tryptophan 460 variant), SLC12A3 (alanine 264 variant), and WNK (cytosine for rs1159744, rs227869, and rs2107614) will be most responsive to renal denervation surgery, particularly when all are functional and when the renal system is considered along with the renin-angiotensin aldosterone and cardiac systems.

TABLE 6

Genetic Variants Proteins Important in Renal Na+ Handling and Predictive Response to Renal Denervation

| Organ System | Gene/Variant | rs# | Importance in Renal Denervation |
|---|---|---|---|
| Kidney (Na+ regulation: plasma volume) | Alpha Adducin | 4961 | Average |
| | SCNN1A | 2228576 | Average |
| | SLC12A3 (2) | 1529927 | Average |
| | WNK1(a) | 1159744 | High |
| | WNK1(b) | 2107614 | High |
| | WNK1(c) | 2277869 | Average |

Summary of Blood Pressure Panel Strategy

The embodiments of the invention include creation of the blood pressure panel to comprehensively assess common genetic variants in the SNS, cardiac, renin-angiotensin aldosterone, and renal systems. The categorization of the panel provides a hierarchy of genetic variations that determine patients who will very highly, highly, moderately highly, moderately, minimally or will not respond to renal denervation. According to the invention, the categorization and hierarchy are based on the consideration of groups of these various genotypes. The categorization and hierarchy are presented in Table 7.

TABLE 7

Rank Order for Gene Combinations to Determine Response to Renal Denervation Surgery
Predictive Response

| | Genetic Combinations | SNS Fx? | RAAS All FX? | Cardiac All Fx? | Rank (higher # More Responsive) |
|---|---|---|---|---|---|
| Most Likely to Respond | Fx SNS reg Genes+ RAAS Genes+ all Cardiac Genes+ all Renal Genes | Y | Y | Y | 10 |
| | Fx A2AC reg Genes+ RAAS Genes+ all Cardiac Genes+ all Renal Genes | Y | Y | Y | 9 |
| | Fx all RAAS Genes+ all Cardiac Genes+ all Renal Genes | | Y | Y | 8 |
| | Fx all RAAS Genes+ all Cardiac Genes+ (some) Renal Genes | | Y | Y | 7 |
| | Fx all RAAS Genes+ (most) Cardiac Genes+ (some) Renal Genes | | Y | | 6 |
| | Fx all RAAS Genes+ (most) Cardiac Genes+ (no) Renal Genes | | Y | | 5 |
| | Fx all RAAS Genes+ (some) Cardiac Genes+ (no) Renal Genes | | Y | | 4 |
| | Fx all RAAS Genes+ (no) Cardiac Genes+ (no) Renal Genes | | Y | | 3 |
| | Fx (some) RAAS Genes+ (no) Cardiac Genes+ (no) Renal Genes | | | | 2 |
| Least Likely to Respond | Fx (no) RAAS Genes+ (no) Cardiac Genes+ (no) Renal Genes | | | | 1 |

Summary of Renal Denervation Panel Strategy

The blood pressure panel created according to the present invention has been created to comprehensively assess common genetic variants in the SNS, cardiac, vascular, and renal systems that predict who will respond to renal denervation treatment. Based on this information, a clinician can employ this method to determine the appropriate patient for this surgery.

Sample Processing

Each patient will be given a collection kit consisting of two buccal swabs and two uniquely barcoded tubes (termed A and B swabs) containing a proprietary lysis buffer consisting of 50 mM Tris pH 8.0, 50 mM EDTA, 25 mM Sucrose, 100 mM NaCl, and 1% SDS. The patient will use the swab to collect buccal cells by scraping the inside of their cheek and place the swab in the provided barcoded tube, one swab for each cheek. Once the swab has been placed into the lysis buffer the cells are no longer viable and therefore samples are now considered to be nucleic acids and safe to be shipped via standard mail. Upon receipt at the testing facility each sample will be run through the sample processing workflow algorithm depicted as FIG. 1.

Initially all samples will be checked-in; their barcodes scanned and their arrival in the laboratory confirmed. They will be grouped into sets of 91 and assigned positions in 96 sample grids (12×8 grid layout) for DNA extraction. The remaining five positions in each grid will be extraction controls (four negative controls [H2O] and one non-human positive). The five controls will be assigned random positions in each grid, giving each grid/plate a unique "plate fingerprint". The randomly assigned controls prevent possible plate swaps or 180° rotations as every plate is now identifiable simply by control positions. All samples are then normalized to a volume of 650 ul with the further necessary amount of above mentioned lysis buffer. Additionally, 25 ul of ProK is added to each sample and incubated in a 55C oven for a minimum of 4 hours. Following incubation, samples are extracted using a BioSprint96 (KingFisher96) Robotic workstation with magnetic-particle DNA purification chemistry to isolate genomic DNA (GenomicDNA) from tissue samples. This protocol utilizes the chemistry from the eVoMagDNA Extraction KF96 Kit (Verde Labs, Marietta, GA) and is run to specifications provided by the manufacturer. Following DNA extraction and subsequent dessication, the DNA will be resuspended in HPLC water. 5 ul of each sample will then be transferred to assay plates for the first pair of QA assays, both a PicoGreen fluorometric quantification and spectrophotometric purity estimation. The fluorescence and absorbance data will be analyzed for all samples in the 96 well plate, including the five controls. The positions of the negative controls will be confirmed and accessed for possible plate contamination. The results of the positive control as well as the samples on the plate will be analyzed for quality metrics using a systems analysis approach, simply put we will be able to statistically assess outliers. After the quantification and purity QA assays, robotic systems will be used to transfer the samples into racks of 96 sample septa sealed plates (to ensure there is no evaporative loss) and a fractional volume of each sample will be used to create a daughter plate of the samples at a normalized concentration of 5 ng/μl for the PCR QA assays and subsequent genotyping. The creation of the normalized daughter plate serves two purposes; first it allows the immediate storage of the primary stock of each sample at −80° C. avoiding the need for unnecessary freeze-thaw of samples and the potential contamination risks associated with repeated accessing of the stock, and second it avoids unnecessary waste of the DNA associated with the use of full concentration stock for the PCR applications (this −80 stock DNA can be used at any time or saved for future testing). Any samples that fail any of the QA assays will re-enter the pipeline and be sorted and re-processed from the B-swab, this is the second tube/swab in the kit sent to the customer mentioned above. By always having a backup sample we ensure that we will never have to go back to the customer to ask for a re-swab. If the quantity and purity are still insufficient then whole genome amplification or organic re-extraction will be employed respectively. Following the passage of the QA thresholds normalized fractions of the samples will be transferred to PCR plates for genotyping. Each sample will be analyzed using 2 different methodolo gies, the Sequenom MassArray genotyping platform and classical PCR and gel sizing to determine insertion/deletion status. The Sequenom MassArray genotyping platform will be used to analyze the following sites-rs1042713, rs1042714, rs1801252, rs1801253, rs4961, rs2228576, rs1529927, rs1159744, rs2107614, rs2277869, rs12750834, rs5051, rs699, rs7079 and rs5186. While classical gel sizing will be used to determine the insertion/deletion status of rs1799752.

Sequenom MassArray Assay Design and Processing

The Sequenom platform is able to perform genotyping as a 12plex assay (testing 12 variable sites in one reaction) in a 96 well format using one aliquot of DNA. The AssayDesign software from Sequenom is used to generate both PCR and single base extension primers using the individual rs #of each variable site to create the final assay design below as Table 10A (Multiplex PCT Reaction and Table 10B (Extension Reaction):

TABLE 10A

Multiplex Reaction

| SNP_ID | 2nd-PCRP | 1st-PCRP | AMP_LEN | UP_CONF | MP_CONF | Tm (NN) |
|---|---|---|---|---|---|---|
| rs2484516 | ACGTTGGATGTTCATGCGGCCCCCACACT (SEQ ID NO: 54) | ACGTTGGATGGAGACTTCCAAAGTTGTGCG (SEQ ID NO: 55) | 120 | 86.9 | 86 | 62.8 |
| rs553668 | ACGTTGGATGCCCCATGTGTGCTATCAAAA (SEQ ID NO: 56) | ACGTTGGATGATTCCCCTTCCATTCCCAAC (SEQ ID NO: 57) | 138 | 90.7 | 86 | 45.8 |
| rs13118711 | ACGTTGGATGTACTCAGTAGTATTGCTACC (SEQ ID NO: 58) | ACGTTGGATGCTTATATTGATAGGCAATGAG (SEQ ID NO: 59) | 141 | 73.9 | 86 | 45 |
| rs3892097 | ACGTTGGATGGTGGGTGATGGGCAGAAG (SEQ ID NO: 60) | ACGTTGGATGCTGCAgAGACtccTCGGTCT (SEQ ID NO: 61) | 150 | 96.3 | 69 | 53.5 |
| rs4961 | ACGTTGGATGCACCTTAGTCTTCGACTTGG (SEQ ID NO: 62) | ACGTTGGATGACAAGATGGCTGAACTCTGG (SEQ ID NO: 63) | 104 | 99.9 | 75 | 50.1 |
| rs1042713 | ACGTTGGATGCGAACTTGGCAATGGCTGTG (SEQ ID NO: 64) | ACGTTGGATGAGCGCCTTCTTGCTGGCAC (SEQ ID NO: 65) | 134 | 86.5 | 75 | 57.1 |
| rs2277869 | ACGTTGGATGTGAGTTGTTCAGCCTTAGCAGCA (SEQ ID NO: 66) | ACGTTGGATGCCTAGGTTACAATTTCAGGAAG (SEQ ID NO: 67) | | | | |
| rs1801252 | ACGTTGGATGCCTCGTTGCTGCCTCCCG (SEQ ID NO: 68) | ACGTTGGATGATGAGCGCCATCAGCAGAC (SEQ ID NO: 69) | 105 | 70.1 | 75 | 63.5 |
| rs1529927 | ACGTTGGATGTTGGACTCCCACTCCATGC (SEQ ID NO: 70) | ACGTTGGATGCCCATCGTGGACCCCATTAA (SEQ ID NO: 71) | 118 | 91 | 75 | 55.3 |
| rs7079 | ACGTTGGATGAGGCTTATTGTGGCAAGAC (SEQ ID NO: 72) | ACGTTGGATGGTGAAAGATGCAAGCACCTG (SEQ ID NO: 73) | 118 | 98.7 | 75 | 46.6 |
| rs1801253 | ACGTTGGATGTCAACCCCATCATCTACTGC (SEQ ID NO: 74) | ACGTTGGATGGGTCTCCGTGGGTCGCGTG (SEQ ID NO: 75) | 128 | 71.2 | 75 | 55.7 |
| rs699 | ACGTTGGATGGATTGACAGGTTCATGCAGG (SEQ ID NO: 76) | ACGTTGGATGTGGACGTAGGTGTTGAAAGC (SEQ ID NO: 77) | 119 | 98.6 | 75 | 56.9 |
| rs2107614 | ACGTTGGATGGCAACCATCACAGTACTAAG (SEQ ID NO: 78) | ACGTTGGATGCACAACTGGAAGAGTTGAGG (SEQ ID NO: 79) | 111 | 98.1 | 75 | 45.8 |
| rs2228576 | ACGTTGGATGTCCCTCTCCAGCCTTGACAG (SEQ ID NO: 80) | ACGTTGGATGAACCTCTCCTTCCCTCTCAG (SEQ ID NO: 81) | 151 | 83.8 | 75 | 60.5 |
| rs12750834 | ACGTTGGATGACAGGCTACCTGGCTTTAAC (SEQ ID NO: 82) | ACGTTGGATGGGAATCCAGGAGAATAGGTC (SEQ ID NO: 83) | | | | |
| rs5186 | ACGTTGGATGAGAAGCCTGCACCATGTTTTG (SEQ ID NO: 84) | ACGTTGGATGCAGTCCACATAATGCATTTTC (SEQ ID NO: 85) | 170 | | | |
| rs1042714 | ACGTTGGATGATGAGAGACATGACGATGCC (SEQ ID NO: 86) | ACGTTGGATGAGCGCCTTCTTGCTGGCAC (SEQ ID NO: 87) | 127 | 88 | 98 | 54.7 |
| rs1159744 | ACGTTGGATGGTTTTTCAGTTCCTGAATTTG (SEQ ID NO: 88) | ACGTTGGATGGAAACAGTGACAGCCAAATG (SEQ ID NO: 89) | 133 | 79 | 75 | 46.1 |
| rs5051 | ACGTTGGATGTGTAGTACCCAGAACAACGG (SEQ ID NO: 90) | ACGTTGGATGAGCCTGGGAACAGCTCCATC (SEQ ID NO: 91) | 113 | 93.7 | 98 | 55.3 |
| ACE_INDEL | ACGTTGGACTGGAGACCACTCCCATCCTTT (SEQ ID NO: 92) | ACGTTGATGTGGCCATCACATTCGTCAGAT (SEQ ID NO: 93) | 103 | 98.5 | 61 | 45.1 |
| ACE_INDEL (2) | | ACGTTGATTGAGACCATCCCGGCTAAAACG (SEQ ID NO: 94) | | | | |

TABLE 10B

| Extension Reaction | | | | | | | | |
|---|---|---|---|---|---|---|---|---|
| SNP ID | UEPM | UEP SEQ | EXT1 | EXT1M | EXT1 SEQ | EXT | EXT2M | EXT2 SEQ |
| rs2484516 | 4450.9 | CGCCGCCGCCGTCCC (SEQ ID NO: 95) | C | 4698.1 | CGCCGCCGCCGTCCCC (SEQ ID NO: 96) | G | 4738.1 | CGCCGCCGCCGTCCCG (SEQ ID NO: 97) |
| rs553668 | 5406.5 | GCCCTTAGCATTTTTCTT (SEQ ID NO: 98) | G | 5653.7 | GCCCTTAGCATTTTTCTTC (SEQ ID NO: 99) | A | 5733.6 | GCCCTTAGCATTTTTCTTT (SEQ ID NO: 100) |
| rs13118711 | 6650.3 | CTTTACCTATGATTCAGTCTTA (SEQ ID NO: 101) | G | 6897.5 | CTTTACCTATGATTCAGTCTTAC (SEQ ID NO: 102) | C | 6937.6 | CTTTACCTATGATTCAGTCTTAG (SEQ ID NO: 103) |
| rs3892097 | 4996.3 | CGCATCTCCCACCCCCA (SEQ ID NO: 104) | T | 5267.5 | CGCATCTCCCACCCCCAA (SEQ ID NO: 105) | C | 5283.5 | CGCATCTCCCACCCCCAG (SEQ ID NO: 106) |
| rs4961 | 5072.3 | ACTGCTTCCATTCTGCC (SEQ ID NO: 107) | G | 5319.5 | ACTGCTTCCATTCTGCCC (SEQ ID NO: 108) | T | 5343.5 | ACTGCTTCCATTCTGCCA (SEQ ID NO: 109) |
| rs1042713 | 5178.4 | GTCCGGCGCATGGCTTC (SEQ ID NO: 110) | G | 5425.5 | GTCCGGCGCATGGCTTCC (SEQ ID NO: 111) | A | 5505.5 | GTCCGGCGCATGGCTTCT (SEQ ID NO: 112) |
| rs2277869 | 5360.5 | aTTCCCAGTTCATCCTCT (SEQ ID NO: 113) | C | 5607.7 | aTTCCCAGTTCATCCTCTC (SEQ ID NO: 114) | T | 5687.6 | aTTCCCAGTTCATCCTCTT (SEQ ID NO: 115) |
| rs1801252 | 5734.7 | GCTGCCTCCCGCCAGCGAA (SEQ ID NO: 116) | A | 6005.9 | GCTGCCTCCCGCCAGCGAAA (SEQ ID NO: 117) | G | 6021.9 | GCTGCCTCCCGCCAGCGAAG (SEQ ID NO: 118) |
| rs1529927 | 5791.8 | CACAGTGACCGAGACCACG (SEQ ID NO: 119) | G | 6039 | CACAGTGACCGAGACCACGC (SEQ ID NO: 120) | C | 6079 | CACAGTGACCGAGACCACGG (SEQ ID NO: 121) |
| rs7079 | 5869.9 | GGGAGAAATAACCAGCTAT (SEQ ID NO: 122) | G | 6157.1 | GGGAGAAATAACCAGCTATG (SEQ ID NO: 123) | T | 6196.9 | GGGAGAAATAACCAGCTATT (SEQ ID NO: 124) |
| rs1801253 | 6062 | aaTTCCGCAAGGCCTTCCAG (SEQ ID NO: 125) | C | 6309.1 | aaTTCCGCAAGGCCTTCCAGC (SEQ ID NO: 126) | G | 6349.2 | aaTTCCGCAAGGCCTTCCAGG (SEQ ID NO: 127) |
| rs699 | 6118 | GAAGACTGGCTGCTCCCTGA (SEQ ID NO: 128) | C | 6365.2 | GAAGACTGGCTGCTCCCTGAC (SEQ ID NO: 129) | T | 6445.1 | GAAGACTGGCTGCTCCCTGAT (SEQ ID NO: 130) |
| rs2107614 | 6393.2 | TCCTCCAAAAAAAAAGAAAAC (SEQ ID NO: 131) | C | 6640.4 | TCCTCCAAAAAAAAAGAAAACC (SEQ ID NO: 132) | T | 6720.3 | TCCTCCAAAAAAAAAGAAAACT (SEQ ID NO: 133) |
| rs2228576 | 6399.1 | gCTGCAGGGGCCAGTTCCTCC (SEQ ID NO: 134) | T | 6670.4 | gCTGCAGGGGCCAGTTCCTCCA (SEQ ID NO: 135) | C | 6686.4 | gCTGCAGGGGCCAGTTCCTCCG (SEQ ID NO: 136) |
| rs12750834 | 6479.2 | ggaCAAAGCAGGCTTAATCTG (SEQ ID NO: 137) | A | 6750.4 | ggaCAAAGCAGGCTTAATCTGA (SEQ ID NO: 138) | G | 6766.4 | ggaCAAAGCAGGCTTAATCTGG (SEQ ID NO: 139) |
| rs5186 | 6608.3 | CACTTCCCACTACCAAATGAGC (SEQ ID NO: 140) | C | 6855.5 | CACTTCCCACTACCAAATGAGCC (SEQ ID NO: 141) | A | 6879.51 | CACTTCCCACTACCAAATGAGCA (SEQ ID NO: 142) |
| rs1042714 | 6815.4 | tACCACCCACACCTCGTCCCTTT (SEQ ID NO: 143) | G | 7062.6 | tACCACCCACACCTCGTCCCTTTC (SEQ ID NO: 144) | C | 7102.59 | tACCACCCACACCTCGTCCCTTTG (SEQ ID NO: 145) |
| rs1159744 | 7034.6 | ACTGATATTCTCTATTTGTTGAG (SEQ ID NO: 146) | G | 7281.8 | ACTGATATTCTCTATTTGTTGAGC (SEQ ID NO: 147) | C | 7321.8 | ACTGATATTCTCTATTTGTTGAGG (SEQ ID NO: 148) |
| rs5051 | 7218.7 | ccGAACAACGGCAGCTTCTTCCCC (SEQ ID NO: 149) | C | 7465.9 | ccGAACAACGGCAGCTTCTTCCCCC (SEQ ID NO: 150) | T | 7545.77 | ccGAACAACGGCAGCTTCTTCCCCT (SEQ ID NO: 151) |
| ACE_INDEL | 7872.1 | GACCTGCTGCCTATACAGTCACTTTT (SEQ ID NO: 152) | WT | 8143.3 | GACCTGCTGCCTATACAGTCACTTTTA (SEQ ID NO: 153) | INS | 8199.2 | GACCTGCTGCCTATACAGTCACTTTTT (SEQ ID NO: 154) |

DNA samples at a concentration of 5 ng/ul undergo a PCR using the above designed PCR primers and the Sequnom iPLEX Gold Reagent kit under the following conditions:

| Reagent | Final Conc | Vol/rxn (uL) |
|---|---|---|
| Water, HPLC | N/A | 1.8 |
| 10x PCR Buffer with 20 mM MgCl2 | 2 mM MgCl2 | 0.5 |
| 25 mM MgCl2 | 2 mM | 0.4 |
| 25 mM dNTP Mix | 500 uM | 0.1 |
| 0.5 mM Primer Mix | 0.1 uM | 1 |
| 5 U/uL PCR Enzyme | 1 unit | 0.2 |
| Volume | | 4 |
| 10 ng/uL DNA | 10 ng/rxn | 1 |
| Total Volume | | 5 |

Cycling conditions:

Cycler Program iPlex-PCR

| Temp (° C.) | Time (min) | |
|---|---|---|
| 95 | 2:00 | |
| 95 | 0:30 | Repeat |
| 56 | 0:30 | 45 |
| 72 | 1:00 | Cycles |
| 72 | 5:00 | |
| 4 | ∞ | |

Directly following PCR amplification excess primers and dntp's are removed via a SAP (shrimp alkaline phosphatase) reaction under the following conditions:

| Reagent | Final Conc | Vol/rxn (uL) |
|---|---|---|
| Water, HPLC | N/A | 1.53 |
| SAP Buffer (10x) | 0.24x | 0.17 |
| 5 U/uL PCR Enzyme | 1 unit | 0.2 |
| Volume | | 2 |
| PCR product | | 5 |
| Total Volume | | 7 |

Cycling conditions:
Cycler Program
iPlex-SAP

| Temp (° C.) | Time (min) |
|---|---|
| 37 | 40:00 |
| 85 | 5:00 |
| 4 | ∞ |

After the SAP reaction is completed the samples undergo the SBE (single base extension) reaction using the following conditions:

| Reagents | Final Conc | Vol/rxn (uL) |
|---|---|---|
| Water, HPLC | N/A | 0.619 |
| iPlex Gold Buffer | 0.222x | 0.200 |
| iPlex Termination Mix | 1x | 0.200 |
| iPlex Extend Primer Mix | varies | 0.940 |
| iPlex Enzyme | 1x | 0.041 |
| Volume | | 2.000 |
| PCR product | | 7 |
| Total Volume | | 9 |

Cycling conditions:

| Temp (∞C.) | Time (min) | | |
|---|---|---|---|
| 94 | 0:30 | | |
| 94 | 0:05 | | 40 cycles ↓ |
| 52 | 0:05 | 5 cycles ↓ | |
| 80 | 0:05 | | |
| 72 | 3:00 | | |
| 4 | forever | | |

After completion of all above reactions samples are run through resin based clean-up to remove excess salts according to standard Sequenom protocols. Samples are then spotted onto the Sequenom provided SpectroChip using the Sequenom Nanodispenser according to manufacturer protocols and subsequently processed on the Sequenom MALDI-TOF platform.

Gel Sizing Primer Design and Workflow

To accurately call the insertion/deletion status for site rs #1799752 a PCR followed by gel electrophoresis is performed. The PCR primers for this site can also be designed and optimized using Primer3 and the above-mentioned buffer and temperature gradient. The following primer sequences and PCR conditions are ultimately chosen:

| Primer Name | Sequence | Purpose |
|---|---|---|
| rs1799752_F-2 | CCCATTTCTCTAGACCTGCT (SEQ ID NO: 155) | INDEL |
| rs1799752_R-2 | GGGATGGTGTCTCGTACATA (SEQ ID NO: 156) | INDEL |

Cycling Conditions:

| | | | |
|---|---|---|---|
| Master Mix | | 44 | |
| H20 | 7.7 | | 372.68 |
| Buffer C 10x | 1 | | 48.4 |
| dNPTs (2.5 mM) | 0.8 | | 38.72 |
| Forward (20 ng/ul) | 0.2 | | 9.68 |
| Reverse (20 ng/ul) | 0.2 | | 9.68 |
| Taq polymerase | 0.1 | | 4.84 |
| DNA | 0 | | 0 |

| | | | |
|---|---|---|---|
| Denature | 94 | 3 min | |
| Denature | 94 | 30 sec | X35 |
| Anneal | 60 | 30 sec | |
| Extend | 72 | 120 sec | |
| Final Extend | 72 | 3 min | |

Figure 2:
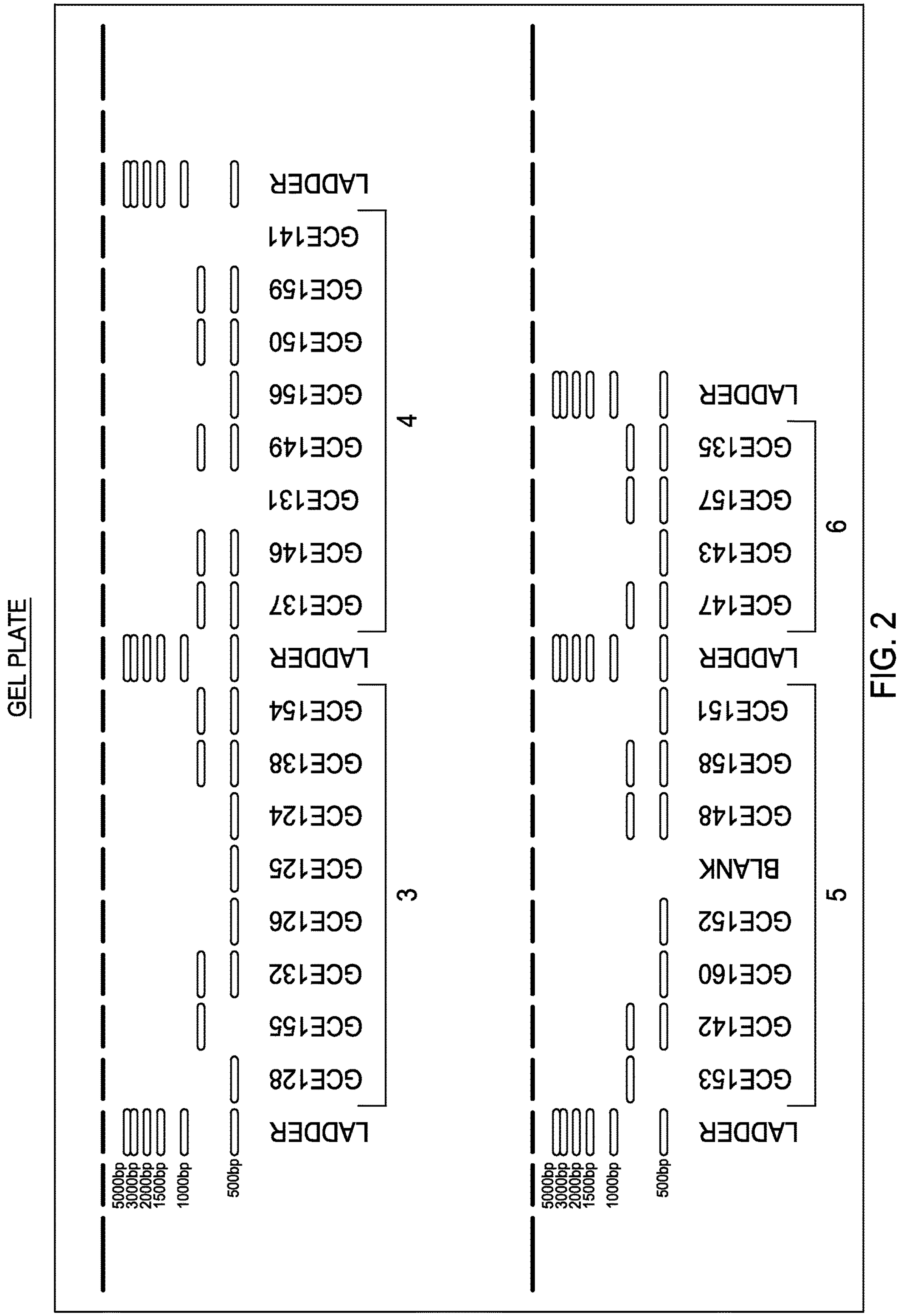
FIG. 2 is a Gel Plate of the result of a chromatographic examination of a sample genetic panel of a patient.

Following PCR each sample is loaded into its own well of a 2% agarose gel and run at 150 mV for approximately 45 min and stained in a bath of GelRed for 2 hours prior to imaging with UV light. The resulting image is used to score the presence or absence of a 288 bp ALU visually examining the gel for either the higher molecular weight band (indicating the presence of the 288 bp ALU), the lower molecular weight band (indicating the absence of the 288 bp ALU) or both (indicating a heterozygous state). A sample image of the gel is shown on FIG. 2.

Once all tests are performed a report is generated containing all results for each tested patient and delivered for interpretation.

Renal Denervation Procedure

The procedure for partial renal denervation can be performed according to the protocols set forth in the Symplicity studies or in *Lancet,* 2009, 373, 1275-81, Krum et al. Briefly, the procedure involves introduction of a Symplicity renal denervation catheter (manufactured by Medtronic, Santa Rosa CA) into one or both renal arteries through the corresponding femoral arteries. Multiple radiofrequency denervations of low wattage such as 6 to 8 W or less for up to two minutes for each denervation were applied. The catheter can be drawn back by at least about 5 mm and circumferentially rotated to ensure disruption of the sympathetic plexus surrounding the renal artery. If multiple denervations at variable arterial locations are to be made, the procedure should begin at the denervation location nearest to the arterial junction with the kidney. Blood pressure should be periodically measured before, during and after the procedure to manage untoward bp effects.

Description of Gene Sequences

Descriptions and Sequences for the functional genes and/or their reference sequences for ADRB1 (SEQ ID NO:1), ADRB2 (SEQ ID NO:5), AGT (angiotensin) (SEQ ID NO:13), AGT1R (SEQ ID NO:17), Angiotensin II (SEQ ID NO:18), SCNN1A (version 1) (SEQ ID NO: 21), SCNN1A (version 2) (SEQ ID NO:24), ADD1 (SEQ ID NO:26), SLC12A3 (SEQ ID NO: 29), ADRA2A (SEQ ID NO:50), ADRA2C (SEQ ID NO:51), renin (SEQ ID NO:52) and WNK (SEQ ID NO:53) are provided.

A full length human ADRB1 cDNA nucleotide sequence is available from the database maintained by the National Center for Biotechnology Information (see website at ncbi.nlm.nih.gov), which has accession number NM_00064 (GI: 110349783), and is shown below as SEQ ID NO:1.

```
   1 GCACCACGCC GCCCGGGCTT CTGGGGTGTT CCCCAACCAC
  41 GGCCCAGCCC TGCCACACCC CCCGCCCCCG GCCTCCGCAG
  81 CTCGGCATGG GCGCGGGGGT GCTCGTCCTG GGCGCCTCCG
 121 AGCCCGGTAA CCTGTCGTCG GCCGCACCGC TCCCCGACGG
 161 CGCGGCCACC GCGGCGCGGC TGCTGGTGCC CGCGTCGCCG
 201 CCCGCCTCGT TGCTGCCTCC CGCCAGCGAA AGCCCCGAGC
 241 CGCTGTCTCA GCAGTGGACA GCGGGCATGG GTCTGCTGAT
 281 GGCGCTCATC GTGCTGCTCA TCGTGGCGGG CAATGTGCTG
 321 GTGATCGTGG CCATCGCCAA GACGCCGCGG CTGCAGACGC
 361 TCACCAACCT CTTCATCATG TCCCTGGCCA GCGCCGACCT
 401 GGTCATGGGG CTGCTGGTGG TGCCGTTCGG GGCCACCATC
 441 GTGGTGTGGG GCCGCTGGGA GTACGGCTCC TTCTTCTGCG
```

-continued

```
 481 AGCTGTGGAC CTCAGTGGAC GTGCTGTGCG TGACGGCCAG
 521 CATCGAGACC CTGTGTGTCA TTGCCCTGGA CCGCTACCTC
 561 GCCATCACCT CGCCCTTCCG CTACCAGAGC CTGCTGACGC
 601 GCGCGCGGGC GCGGGGCCTC GTGTGCACCG TGTGGGCCAT
 641 CTCGGCCCTG GTGTCCTTCC TGCCCATCCT CATGCACTGG
 681 TGGCGGGCGG AGAGCGACGA GGCGCGCCGC TGCTACAACG
 721 ACCCCAAGTG CTGCGACTTC GTCACCAACC GGGCCTACGC
 761 CATCGCCTCG TCCGTAGTCT CCTTCTACGT GCCCCTGTGC
 801 ATCATGGCCT TCGTGTACCT GCGGGTGTTC CGCGAGGCCC
 841 AGAAGCAGGT GAAGAAGATC GACAGCTGCG AGCGCCGTTT
 881 CCTCGGCGGC CCAGCGCGGC CGCCCTCGCC CTCGCCCTCG
 921 CCCGTCCCCG CGCCCGCGCC GCCGCCCGGA CCCCCGCGCC
 961 CCGCCGCCGC CGCCGCCACC GCCCCGCTGG CCAACGGGCG
1001 TGCGGGTAAG CGGCGGCCCT CGCGCCTCGT GGCCCTGCGC
1041 GAGCAGAAGG CGCTCAAGAC GCTGGGCATC ATCATGGGCG
1081 TCTTCACGCT CTGCTGGCTG CCCTTCTTCC TGGCCAACGT
1121 GGTGAAGGCC TTCCACCGCG AGCTGGTGCC CGACCGCCTC
1161 TTCGTCTTCT TCAACTGGCT GGGCTACGCC AACTCGGCCT
1201 TCAACCCCAT CATCTACTGC CGCAGCCCCG ACTTCCGCAA
1241 GGCCTTCCAG GGACTGCTCT GCTGCGCGCG CAGGGCTGCC
1281 CGCCGGCGCC ACGCGACCCA CGGAGACCGG CCGCGCGCCT
1321 CGGGCTGTCT GGCCCGGCCC GGACCCCCGC CATCGCCCGG
1361 GGCCGCCTCG GACGACGACG ACGACGATGT CGTCGGGGCC
1401 ACGCCGCCCG CGCGCCTGCT GGAGCCCTGG GCCGGCTGCA
1441 ACGGCGGGGC GGCGGCGGAC AGCGACTCGA GCCTGGACGA
1481 GCCGTGCCGC CCCGGCTTCG CCTCGGAATC CAAGGTGTAG
1521 GGCCCGGCGC GGGGCGCGGA CTCCGGGCAC GGCTTCCCAG
1561 GGGAACGAGG AGATCTGTGT TTACTTAAGA CCGATAGCAG
1601 GTGAACTCGA AGCCCACAAT CCTCGTCTGA ATCATCCGAG
1641 GCAAAGAGAA AAGCCACGGA CCGTTGCACA AAAAGGAAAG
1681 TTTGGGAAGG GATGGGAGAG TGGCTTGCTG ATGTTCCTTG
1721 TTGTTTTTTT TTTCTTTTCT TTTCTTTCTT CTTCTTTTTT
1741 TTTTTTTTTT TTTTTTCTGT TTGTGGTCCG GCCTTCTTTT
1801 GTGTGTGCGT GTGATGCATC TTTAGATTTT TTTCCCCCAC
1841 CAGGTGGTTT TTGACACTCT CTGAGAGGAC CGGAGTGGAA
1881 GATGGGTGGG TTAGGGGAAG GGAGAAGCAT TAGGAGGGGA
1921 TTAAAATCGA TCATCGTGGC TCCCATCCCT TTCCCGGGAA
1961 CAGGAACACA CTACCAGCCA GAGAGAGGAG AATGACAGTT
2001 TGTCAAGACA TATTTCCTTT TGCTTTCCAG AGAAATTTCA
2041 TTTTAATTTC TAAGTAATGA TTTCTGCTGT TATGAAAGCA
```

-continued

```
2081 AAGAGAAAGG ATGGAGGCAA AATAAAAAAA AATCACGTTT

2121 CAAGAAATGT TAAGCTCTTC TTGGAACAAG CCCCACCTTG

2161 CTTTCCTTGT GTAGGGCAAA CCCGCTGTCC CCCGCGCGCC

2201 TGGGTGGTCA GGCTGAGGGA TTTCTACCTC ACACTGTGCA

2241 TTTGCACAGC AGATAGAAAG ACTTGTTTAT ATTAAACAGC

2281 TTATTTATGT ATCAATATTA GTTGGAAGGA CCAGGCGCAG

2321 AGCCTCTCTC TGTGACATGT GACTCTGTCA ATTGAAGACA

2361 GGACATTAAA AGAGAGCGAG AGAGAGAAAC AGTTCAGATT

2401 ACTGCACATG TGGATAAAAA CAAAAACAAA AAAAAGGAGT

2441 GGTTCAAAAT GCCATTTTTG CACAGTGTTA GGAATTACAA

2481 AATCCACAGA AGATGTTACT TGCACAAAAA GAAATTAAAT

2521 ATTTTTTAAA GGGAGAGGGG CTGGGCAGAT CTTAAATAAA

2561 ATTCAAACTC TACTTCTGTT GTCTAGTATG TTATTGAGCT

2601 AATGATTCAT TGGGAAAATA CCTTTTTATA CTCCTTTATC

2641 ATGGTACTGT AACTGTATCC ATATTATAAA TATAATTATC

2681 TTAAGGATTT TTTATTTTTT TTTATGTCCA AGTGCCCACG

2721 TGAATTTGCT GGTGAAAGTT AGCACTTGTG TGTAAATTCT

2761 ACTTCCTCTT GTGTGTTTTA CCAAGTATTT ATACTCTGGT

2801 GCAACTAACT ACTGTGTGAG GAATTGGTCC ATGTGCAATA

2841 AATACCAATG AAGCACAATC AA
```

The rs1801252 single nucleotide polymorphism (SNP) is present in the ADRB1 gene, where the variable nucleotide at about position 231 (underlined) can be adenine in some individuals and guanine in others. The rs1801252 sequence (SEQ ID NO:2) is shown below, where the underlined A/G is the SNP.

```
CTCGTTGCTGCCTCCCGCCAGCGAA[A/G]GCCCCGAGCCGCTGTCTCA
GCAGTG.
```

The rs1801253 single nucleotide polymorphism (SNP) is also present in the ADRB1 gene, where the variable nucleotide at about position 1251 (underlined) can be guanine in some individuals and cytosine in others. The rs1801253 sequence (SEQ ID NO:3) is shown below, where the underlined C/G is the SNP.

```
CCCCGACTTCCGCAAGGCCTTCCAG[C/G]GACTGCTCTGCTGCGCGCG
CAGGGC.
```

A full length human ADRB2 cDNA nucleotide sequence is available from the database maintained by the National Center for Biotechnology Information (see website at ncbi.nlm.nih.gov), which has accession number NM_000024 (GI: 283483994) and is shown below as SEQ ID NO:5.

```
   1 GCACATAACG GGCAGAACGC ACTGCGAAGC GGCTTCTTCA

  41 GAGCACGGGC TGGAACTGGC AGGCACCGCG AGCCCCTAGC

  81 ACCCGACAAG CTGAGTGTGC AGGACGAGTC CCCACCACAC
```

-continued

```
 121 CCACACCACA GCCGCTGAAT GAGGCTTCCA GGCGTCCGCT

 161 CGCGGCCCGC AGAGCCCCGC CGTGGGTCCG CCCGCTGAGG

 201 CGCCCCCAGC CAGTGCGCTC ACCTGCCAGA CTGCGCGCCA

 241 TGGGGCAACC CGGGAACGGC AGCGCCTTCT TGCTGGCACC

 281 CAATAGAAGC CATGCGCCGG ACCACGACGT CACGCAGCAA

 321 AGGGACGAGG TGTGGGTGGT GGGCATGGGC ATCGTCATGT

 361 CTCTCATCGT CCTGGCCATC GTGTTTGGCA ATGTGCTGGT

 401 CATCACAGCC ATTGCCAAGT TCGAGCGTCT GCAGACGGTC

 441 ACCAACTACT TCATCACTTC ACTGGCCTGT GCTGATCTGG

 481 TCATGGGCCT GGCAGTGGTG CCCTTTGGGG CCGCCCATAT

 521 TCTTATGAAA ATGTGGACTT TTGGCAACTT CTGGTGCGAG

 561 TTTTGGACTT CCATTGATGT GCTGTGCGTC ACGGCCAGCA

 601 TTGAGACCCT GTGCGTGATC GCAGTGGATC GCTACTTTGC

 641 CATTACTTCA CCTTTCAAGT ACCAGAGCCT GCTGACCAAG

 681 AATAAGGCCC GGGTGATCAT TCTGATGGTG TGGATTGTGT

 721 CAGGCCTTAC CTCCTTCTTG CCCATTCAGA TGCACTGGTA

 761 CCGGGCCACC CACCAGGAAG CCATCAACTG CTATGCCAAT

 801 GAGACCTGCT GTGACTTCTT CACGAACCAA GCCTATGCCA

 841 TTGCCTCTTC CATCGTGTCC TTCTACGTTC CCCTGGTGAT

 881 CATGGTCTTC GTCTACTCCA GGGTCTTTCA GGAGGCCAAA

 921 AGGCAGCTCC AGAAGATTGA CAAATCTGAG GGCCGCTTCC

 961 ATGTCCAGAA CCTTAGCCAG GTGGAGCAGG ATGGGCGGAC

1001 GGGGCATGGA CTCCGCAGAT CTTCCAAGTT CTGCTTGAAG

1041 GAGCACAAAG CCCTCAAGAC GTTAGGCATC ATCATGGGCA

1081 CTTTCACCCT CTGCTGGCTG CCCTTCTTCA TCGTTAACAT

1121 TGTGCATGTG ATCCAGGATA ACCTCATCCG TAAGGAAGTT

1161 TACATCCTCC TAAATTGGAT AGGCTATGTC AATTCTGGTT

1201 TCAATCCCCT TATCTACTGC CGGAGCCCAG ATTTCAGGAT

1241 TGCCTTCCAG GAGCTTCTGT GCCTGCGCAG GTCTTCTTTG

1281 AAGGCCTATG GGAATGGCTA CTCCAGCAAC GGCAACACAG

1321 GGGAGCAGAG TGGATATCAC GTGGAACAGG AGAAAGAAAA

1361 TAAACTGCTG TGTGAAGACC TCCCAGGCAC GGAAGACTTT

1401 GTGGGCCATC AAGGTACTGT GCCTAGCGAT AACATTGATT

1441 CACAAGGGAG GAATTGTAGT ACAAATGACT CACTGCTGTA

1481 AAGCAGTTTT TCTACTTTTA AAGACCCCCC CCCCCAACAG

1521 AACACTAAAC AGACTATTTA ACTTGAGGGT AATAAACTTA

1561 GAATAAAATT GTAAAATTGT ATAGAGATAT GCAGAAGGAA

1601 GGGCATCCTT CTGCCTTTTT TATTTTTTTA AGCTGTAAAA

1641 AGAGAGAAAA CTTATTTGAG TGATTATTTG TTATTTGTAC

1681 AGTTCAGTTC CTCTTTGCAT GGAATTTGTA AGTTTATGTC
```

-continued

```
1721 TAAAGAGCTT TAGTCCTAGA GGACCTGAGT CTGCTATATT

1761 TTCATGACTT TTCCATGTAT CTACCTCACT ATTCAAGTAT

1801 TAGGGGTAAT ATATTGCTGC TGGTAATTTG TATCTGAAGG

1841 AGATTTTCCT TCCTACACCC TTGGACTTGA GGATTTTGAG

1881 TATCTCGGAC CTTTCAGCTG TGAACATGGA CTCTTCCCCC

1921 ACTCCTCTTA TTTGCTCACA CGGGGTATTT TAGGCAGGGA

1961 TTTGAGGAGC AGCTTCAGTT GTTTTCCCGA GCAAAGTCTA

2001 AAGTTTACAG TAAATAAATT GTTTGACCAT GCCTTCATTG

2041 CAAAAAAAAA AAAAAAA
```

The rs1042713 single nucleotide polymorphism (SNP) is present in the ADRB2 gene, where the variable nucleotide at about position 285 (underlined) can be in adenine some individuals and guanine in others. The rs1042713 sequence (SEQ ID NO:6) is shown below, where the underlined A/G is the SNP.

CAGCGCCTTCTTGCTGGCACCCAAT[A/G]GAAGCCATGCGCCGGACCA
CGACGT.

The rs1042714 single nucleotide polymorphism (SNP) is also present in the ADRB2 gene, where the variable nucleotide at about position 318 (underlined) can be cytosine in some individuals and guanine in others. The rs1042714 sequence (SEQ ID NO:7) is shown below, where the underlined C/G is the SNP.

TGCGCCGGACCACGACGTCACGCAG[C/G]AAAGGGACGAGGTGTGGGT
GGTGGG.

Human angiotensinogen is expressed from the AGT gene. A cDNA nucleotide sequence for human angiotensinogen is provided below as SEQ ID NO:13 (accession number NM_000029.3 GI: 188595658, from the NCBI database).

```
   1 ATCCCATGAG CGGGCAGCAG GGTCAGAAGT GGCCCCCGTG

  41 TTGCCTAAGC AAGACTCTCC CCTGCCCTCT GCCCTCTGCA

  81 CCTCCGGCCT GCATGTCCCT GTGGCCTCTT GGGGGTACAT

 121 CTCCCGGGGC TGGGTCAGAA GGCCTGGGTG GTTGGCCTCA

 161 GGCTGTCACA CACCTAGGGA GATGCTCCCG TTTCTGGGAA

 201 CCTTGGCCCC GACTCCTGCA AACTTCGGTA AATGTGTAAC

 241 TCGACCCTGC ACCGGCTCAC TCTGTTCAGC AGTGAAACTC

 281 TGCATCGATC ACTAAGACTT CCTGGAAGAG GTCCCAGCGT

 321 GAGTGTCGCT TCTGGCATCT GTCCTTCTGG CCAGCCTGTG

 361 GTCTGGCCAA GTGATGTAAC CCTCCTCTCC AGCCTGTGCA

 401 CAGGCAGCCT GGGAACAGCT CCATCCCCAC CCCTCAGCTA

 441 TAAATAGGGC ATCGTGACCC GGCCGGGGGA AGAAGCTGCC

 481 GTTGTTCTGG GTACTACAGC AGAAGGGTAT GCGGAAGCGA

 521 GCACCCCAGT CTGAGATGGC TCCTGCCGGT GTGAGCCTGA

 561 GGGCCACCAT CCTCTGCCTC CTGGCCTGGG CTGGCCTGGC
```

-continued

```
 601 TGCAGGTGAC CGGGTGTACA TACACCCCTT CCACCTCGTC

 641 ATCCACAATG AGAGTACCTG TGAGCAGCTG GCAAAGGCCA

 681 ATGCCGGGAA GCCCAAAGAC CCCACCTTCA TACCTGCTCC

 721 AATTCAGGCC AAGACATCCC CTGTGGATGA AAAGGCCCTA

 761 CAGGACCAGC TGGTGCTAGT CGCTGCAAAA CTTGACACCG

 801 AAGACAAGTT GAGGGCCGCA ATGGTCGGGA TGCTGGCCAA

 841 CTTCTTGGGC TTCCGTATAT ATGGCATGCA CAGTGAGCTA

 881 TGGGGCGTGG TCCATGGGGC CACCGTCCTC TCCCCAACGG

 921 CTGTCTTTGG CACCCTGGCC TCTCTCTATC TGGGAGCCTT

 961 GGACCACACA GCTGACAGGC TACAGGCAAT CCTGGGTGTT

1001 CCTTGGAAGG ACAAGAACTG CACCTCCCGG CTGGATGCGC

1041 ACAAGGTCCT GTCTGCCCTG CAGGCTGTAC AGGGCCTGCT

1081 AGTGGCCCAG GGCAGGGCTG ATAGCCAGGC CCAGCTGCTG

1121 CTGTCCACGG TGGTGGGCGT GTTCACAGCC CCAGGCCTGC

1161 ACCTGAAGCA GCCGTTTGTG CAGGGCCTGG CTCTCTATAC

1201 CCCTGTGGTC CTCCCACGCT CTCTGGACTT CACAGAACTG

1241 GATGTTGCTG CTGAGAAGAT TGACAGGTTC ATGCAGGCTG

1281 TGACAGGATG GAAGACTGGC TGCTCCCTGA TGGGAGCCAG

1321 TGTGGACAGC ACCCTGGCTT TCAACACCTA CGTCCACTTC

1361 CAAGGGAAGA TGAAGGGCTT CTCCCTGCTG GCCGAGCCCC

1401 AGGAGTTCTG GGTGGACAAC AGCACCTCAG TGTCTGTTCC

1441 CATGCTCTCT GGCATGGGCA CCTTCCAGCA CTGGAGTGAC

1481 ATCCAGGACA ACTTCTCGGT GACTCAAGTG CCCTTCACTG

1521 AGAGCGCCTG CCTGCTGCTG ATCCAGCCTC ACTATGCCTC

1561 TGACCTGGAC AAGGTGGAGG GTCTCACTTT CCAGCAAAAC

1601 TCCCTCAACT GGATGAAGAA ACTATCTCCC CGGACCATCC

1641 ACCTGACCAT GCCCCAACTG GTGCTGCAAG GATCTTATGA

1681 CCTGCAGGAC CTGCTCGCCC AGGCTGAGCT GCCCGCCATT

1721 CTGCACACCG AGCTGAACCT GCAAAAATTG AGCAATGACC

1761 GCATCAGGGT GGGGGAGGTG CTGAACAGCA TTTTTTTTGA

1801 GCTTGAAGCG GATGAGAGAG AGCCCACAGA GTCTACCCAA

1841 CAGCTTAACA AGCCTGAGGT CTTGGAGGTG ACCCTGAACC

1881 GCCCATTCCT GTTTGCTGTG TATGATCAAA GCGCCACTGC

1921 CCTGCACTTC CTGGGCCGCG TGGCCAACCC GCTGAGCACA

1961 GCATGAGGCC AGGGCCCCAG AACACAGTGC CTGGCAAGGC

2001 CTCTGCCCCT GGCCTTTGAG GCAAAGGCCA GCAGCAGATA

2041 ACAACCCCGG ACAAATCAGC GATGTGTCAC CCCCAGTCTC

2081 CCACCTTTTC TTCTAATGAG TCGACTTTGA GCTGGAAAGC

2121 AGCCGTTTCT CCTTGGTCTA AGTGTGCTGC ATGGAGTGAG

2161 CAGTAGAAGC CTGCAGCGGC ACAAATGCAC CTCCCAGTTT

2201 GCTGGGTTTA TTTTAGAGAA TGGGGGTGGG GAGGCAAGAA
```

-continued

2241 CCAGTGTTTA GCGCGGGACT ACTGTTCCAA AAAGAATTCC

2281 AACCGACCAG CTTGTTTGTG AAACAAAAAA GTGTTCCCTT

2321 TTCAAGTTGA GAACAAAAAT TGGGTTTTAA AATTAAAGTA

2361 TACATTTTTG CATTGCCTTC GGTTTGTATT TAGTGTCTTG

2401 AATGTAAGAA CATGACCTCC GTGTAGTGTC TGTAATACCT

2441 TAGTTTTTTC CACAGATGCT TGTGATTTTT GAACAATACG

2481 TGAAAGATGC AAGCACCTGA ATTTCTGTTT GAATGCGGAA

2521 CCATAGCTGG TTATTTCTCC CTTGTGTTAG TAATAAACGT

2561 CTTGCCACAA TAAGCCTCCA

2581 AAAAAAA

The rs699 single nucleotide polymorphism (SNP) is present in the AGT gene, where the variable nucleotide is at about position 1311 in SEQ ID NO:13 (underlined), which can be in thymine some individuals and cytosine in others. The rs699 sequence (SEQ ID NO:14) is shown below, where the underlined C/T is the SNP.

GGATGGAAGACTGGCTGCTCCCTGA[C/T]GGGAGCCAGTGTGGACAGC ACCCTG.

A portion of a 3' untranslated region of the AGT1R gene with NCBI accession number NG_008468.1 (GI: 198041751) is shown below (SEQ IDNO: 17) that contains the rs5186 SNP with the variant nucleotide (adenine) identified below in bold and with underlining.

48961 ATTCAACTAG GCATCATACG TGACTGTAGA ATTGCAGATA

49001 TTGTGGACAC GGCCATGCCT ATCACCATTT GTATAGCTTA

49041 TTTTAACAAT TGCCTGAATC CTCTTTTTTA TGGCTTTCTG

49081 GGGAAAAAAT TTAAAAGATA TTTTCTCCAG CTTCTAAAAT

49121 ATATTCCCCC AAAAGCCAAA TCCCACTCAA ACCTTTCAAC

49181 AAAAATGAGC ACGCTTTCCT ACCGCCCCTC AGATAATGTA

49201 AGCTCATCCA CCAAGAAGCC TGCACCATGT TTTGAGGTTG

49241 AGTGACATGT TCGAAACCTG TCCATAAAGT AATTTTGTGA

49301 AAGAAGGAGC AAGAGAACAT TCCTCTGCAG CACTTCACTA

49321 CCAAATGAGC ATTAGCTACT TTTCAGAATT GAAGGAGAAA

49361 ATGCATTATG TGGACTGAAC CGACTTTTCT AAAGCTCTGA

49401 ACAAAAGCTT TTCTTTCCTT TTGCAACAAG ACAAAGCAAA

49441 GCCACATTTT GCATTAGACA GATGACGGCT GCTCGAAGAA

49481 CAATGTCAGA AACTCGATGA ATGTGTTGAT TTGAGAAATT

49521 TTACTGACAG AAATGCAATC TCCCTAGCCT GCTTTTGTCC

49561 TGTTATTTTT TATTTCCACA TAAAGGTATT TAGAATATAT

49601 TAAATCGTTA GAGGAGCAAC AGGAGATGAG AGTTCCAGAT

49641 TGTTCTGTCC AGTTTCCAAA GGGCAGTAAA GTTTTCGTGC

A cDNA sequence for human angiotensin II receptor is provided in the NCBI database as accession number X65699.1 (GI: 510983), which has the following sequence (SEQ ID NO:18).

1 GGCAGCAGCG AGTGACAGGA CGTCTGGACC GGCGCGCCGC

41 TAGCAGCTCT GCCGGGCCGC GGCGGTGATC GATGGGAGCG

81 GCTGGAGCGG ACCCAGCGAG TGAGGGCGCA CAGCCGGACG

121 CCGAGGCGGC GGGCGGGAGA CCGCACCGCG ACGCCGGCCC

161 TCGGCGGACG AGTCGAGCGC CCGGGCGCGG GTGTATTTGA

201 TATAGTGTTT GCAACAAATT CGACCCAGGT GATCAAAATG

241 ATTCTCAACT CTTCTACTGA AGATGGTATT AAAAGAATCC

281 AAGATGATTG TCCCAAAGCT GGAAGGCATA ATTACATATT

321 TGTCATGATT CCTACTTTAT ACAGTATCAT CTTTGTGGTG

361 GGAATATTTG GAAACAGCTT GGTGGTGATA GTCATTTACT

401 TTTATATGAA GCTGAAGACT GTGGCCAGTG TTTTTCTTTT

441 GAATTTAGCA CTGGCTGACT TATGCTTTTT ACTGACTTTG

481 CCACTATGGG CTGTCTACAC AGCTATGGAA TACCGCTGGC

521 CCTTTGGCAA TTACCTATGT AAGATTGCTT CAGCCAGCGT

561 CAGTTTCAAC CTGTACGCTA GTGTGTTTCT ACTCACGTGT

601 CTCAGCATTG ATCGATACCT GGCTATTGTT CACCCAATGA

641 AGTCCCGCCT TCGACGCACA ATGCTTGTAG CCAAAGTCAC

681 CTGCATCATC ATTTGGCTGC TGGCAGGCTT GGCCAGTTTG

721 CCAGCTATAA TCCATCGAAA TGTATTTTTC ATTGAGAACA

761 CCAATATTAC AGTTTGTGCT TTCCATTATG AGTCCCAAAA

801 TTCAACCCTC CCGATAGGGC TGGGCCTGAC CAAAAATATA

841 CTGGGTTTCC TGTTTCCTTT TCTGATCATT CTTACAAGTT

881 ATACTCTTAT TTGGAAGGCC CTAAAGAAGG CTTATGAAAT

921 TCAGAAGAAC AAACCAAGAA ATGATGATAT TTTTAAGATA

961 ATTATGGCAA TTGTGCTTTT CTTTTTCTTT TCCTGGATTC

1001 CCCACCAAAT ATTCACTTTT CTGGATGTAT TGATTCAACT

1041 AGGCATCATA CGTGACTGTA GAATTGCAGA TATTGTGGAC

1081 ACGGCCATGC CTATCACCAT TTGTATAGCT TATTTTAACA

1121 ATTGCCTGAA TCCTCTTTTT TATGGCTTTC TGGGGAAAAA

1161 ATTTAAAAGA TATTTTCTCC AGCTTCTAAA ATATATTCCC

1201 CCAAAAGCCA AATCCCACTC AAACCTTTCA ACAAAAATGA

1241 GCACGCTTTC CTACCGCCCC TCAGATAATG TAAGCTCATC

1281 CACCAAGAAG CCTGCACCAT GTTTTGAGGT TGAGTGACAT

1321 GTTCGAAACC TGTCCATAAA GTAATTTTGT GAAAGAAGGA

1361 GCAAGAGAAC ATTCCTCTGC AGCACTTCAC TACCAAATGA

1401 GCATTAGCTA CTTTTCAGAA TTGAAGGAGA AAATGCATTA

1441 TGTGGACTGA ACCGACTTTT CTAAAGCTCT GAACAAAAGC

1481 TTTTCTTTCC TTTTGCAACA AGACAAAGCA AAGCCACATT

1521 TTGCATTAGA CAGATGACGG CTGCTCGAAG AACAATGTCA

1561 GAAACTCGAT GAATGTGTTG ATTTGAGAAA TTTTACTGAC

1601 AGAAATGCAA TCTCCCTAGC CTGCTTTTGT CCTGTTATTT

-continued

```
1641 TTTATTTCCA CATAAAGGTA TTTAGAATAT ATTAACTCGT
1681 TAGAGGAGCA ACAGGAGATG AGAGTTCCAG ATTGTTCTGT
1721 CCAGTTTCCA AAGGGCAGTA AAGTTTTCGT GCCTGTTTTC
1761 AGCTATTAGC AACTGTGCCT ACACTTGCAC CTGGTCTGCA
1801 CATTTTGTAC AAAGATATGC TTAAGCAGTA GTCGTCAAGT
1841 TGCAGATCTT TGTTGTGAAA TTCAACCTGT GTCTTATAGG
1881 TTTACACTGC CAAAACAATG CCCGTAAGAT GGCTTATTTG
1921 TATAATGGTG TTACCTAAAG TCACATATAA AAGTTAAACT
1961 ACTTGTAAAG GTGCTGCACT GGTCCCAAGT AGTAGTGTCT
2001 TCCTAGTATA TTAGTTTGAT TTAATATCTG AGAAGTGTAT
2041 ATAGTTTGTG GTAAAAAGAT TATATATCAT AAAGTATGCC
2081 TTCCTGTTTA AAAAAAGTAT ATATTCTACA CATATATGTA
2121 TATGTATATC TATATCTCTA AACTGCTGTT AATTGATTAA
2161 AATCTGGCAA AGTTATATTT ACCCC
```

The nucleotide sequence surrounding the renin rs12750834 single nucleotide polymorphism is shown below, where the underlined A/G in the sequence (SEQ ID NO:19) is the SNP.

AGAACACCAAAGCAGGCTTAATCTG[A/G]GGGCACTTACAGAGACTGC
TTTAAA.

The complementary sequence of SEQ ID NO:19 is the following sequence (SEQ ID NO:20).

TTTAAAGCAGTCTCTGTAAGTGCCC[C/T]CAGATTAAGCCTGCTTTGG
TGTTCT

A cDNA sequence for the human SCNN1A gene is available from the NCBI database as accession number NM_001159576.1 (GI: 227430288). This sequence is provided below as SEQ ID NO: 21.

```
   1 AAACAGAAGG CAGATAGAGA GGGAGTGAGA GGCAGGAGCT
  41 GAGACACAGA TCCTGGAGGA AGAAGACCAA AGGAAGGGGG
  81 CAGAGACAGA AAGGGAGGTG CTAGGACAAA ACTCGAAAGG
 121 TGGCCCTATC AGGGAAGCAG AGGAGAGGCC GTTCTAGGGA
 161 AGCCCAGCTC CGGCACTTTT GGCCCCAACT CCCGCAGGTC
 201 TGCTGGCTCC AGGAAAGGTG GAGGAGGGAG GGAGGAGTGG
 241 GAGAATGTGG GCGCAGGGTG GGACATGGGC ATGGCCAGGG
 281 GCAGCCTCAC TCGGGTTCCA GGGGTGATGG GAGAGGGCAC
 321 TCAGGGCCCA GAGCTCAGCC TTGACCCTGA CCCTTGCTCT
 361 CCCCAATCCA CTCCGGGGCT CATGAAGGGG AACAAGCTGG
 401 AGGAGCAGGA CCCTAGACCT CTGCAGCCCA TACCAGGTCT
 441 CATGGAGGGG AACAAGCTGG AGGAGCAGGA CTCTAGCCCT
 481 CCACAGTCCA CTCCAGGGCT CATGAAGGGG AACAAGCGTG
 521 AGGAGCAGGG GCTGGGCCCC GAACCTGCGG CGCCCCAGCA
```

-continued

```
 561 GCCCACGGCG GAGGAGGAGG CCCTGATCGA GTTCCACCGC
 601 TCCTACCGAG AGCTCTTCGA GTTCTTCTGC AACAACACCA
 641 CCATCCACGG CGCCATCCGC CTGGTGTGCT CCCAGCACAA
 681 CCGCATGAAG ACGGCCTTCT GGGCAGTGCT GTGGCTCTGC
 721 ACCTTTGGCA TGATGTACTG GCAATTCGGC CTGCTTTTCG
 761 GAGAGTACTT CAGCTACCCC GTCAGCCTCA ACATCAACCT
 801 CAACTCGGAC AAGCTCGTCT TCCCCGCAGT GACCATCTGC
 841 ACCCTCAATC CCTACAGGTA CCCGGAAATT AAAGAGGAGC
 881 TGGAGGAGCT GGACCGCATC ACAGAGCAGA CGCTCTTTGA
 921 CCTGTACAAA TACAGCTCCT TCACCACTCT CGTGGCCGGC
 961 TCCCGCAGCC GTCGCGACCT GCGGGGGACT CTGCCGCACC
1001 CCTTGCAGCG CCTGAGGGTC CCGCCCCCGC CTCACGGGGC
1041 CCGTCGAGCC CGTAGCGTGG CCTCCAGCTT GCGGGACAAC
1081 AACCCCCAGG TGGACTGGAA GGACTGGAAG ATCGGCTTCC
1121 AGCTGTGCAA CCAGAACAAA TCGGACTGCT TCTACCAGAC
1161 ATACTCATCA GGGGTGGATG CGGTGAGGGA GTGGTACCGC
1201 TTCCACTACA TCAACATCCT GTCGAGGCTG CCAGAGACTC
1241 TGCCATCCCT GGAGGAGGAC ACGCTGGGCA ACTTCATCTT
1281 CGCCTGCCGC TTCAACCAGG TCTCCTGCAA CCAGGCGAAT
1321 TACTCTCACT TCCACCACCC GATGTATGGA AACTGCTATA
1361 CTTTCAATGA CAAGAACAAC TCCAACCTCT GGATGTCTTC
1401 CATGCCTGGA ATCAACAACG GTCTGTCCCT GATGCTGCGC
1441 GCAGAGCAGA ATGACTTCAT TCCCCTGCTG TCCACAGTGA
1481 CTGGGGCCCG GGTAATGGTG CACGGGCAGG ATGAACCTGC
1521 CTTTATGGAT GATGGTGGCT TTAACTTGCG GCCTGGCGTG
1561 GAGACCTCCA TCAGCATGAG GAAGGAAACC CTGGACAGAC
1601 TTGGGGGCGA TTATGGCGAC TGCACCAAGA ATGGCAGTGA
1641 TGTTCCTGTT GAGAACCTTT ACCCTTCAAA GTACACACAG
1681 CAGGTGTGTA TTCACTCCTG CTTCCAGGAG AGCATGATCA
1721 AGGAGTGTGG CTGTGCCTAC ATCTTCTATC CGCGGCCCCA
1761 GAACGTGGAG TACTGTGACT ACAGAAAGCA CAGTTCCTGG
1801 GGGTACTGCT ACTATAAGCT CCAGGTTGAC TTCTCCTCAG
1841 ACCACCTGGG CTGTTTCACC AAGTGCCGGA AGCCATGCAG
1881 CGTGACCAGC TACCAGCTCT CTGCTGGTTA CTCACGATGG
1921 CCCTCGGTGA CATCCCAGGA ATGGGTCTTC CAGATGCTAT
1961 CGCGACAGAA CAATTACACC GTCAACAACA AGAGAAATGG
2001 AGTGGCCAAA GTCAACATCT TCTTCAAGGA GCTGAACTAC
2041 AAAACCAATT CTGAGTCTCC CTCTGTCACG ATGGTCACCC
2081 TCCTGTCCAA CCTGGGCAGC CAGTGGAGCC TGTGGTTCGG
2121 CTCCTCGGTG TTGTCTGTGG TGGAGATGGC TGAGCTCGTC
```

-continued

```
2161 TTTGACCTGC TGGTCATCAT GTTCCTCATG CTGCTCCGAA
2201 GGTTCCGAAG CCGATACTGG TCTCCAGGCC GAGGGGGCAG
2241 GGGTGCTCAG GAGGTAGCCT CCACCCTGGC ATCCTCCCCT
2281 CCTTCCCACT TCTGCCCCCA CCCCATGTCT CTGTCCTTGT
2321 CCCAGCCAGG CCCTGCTCCC TCTCCAGCCT TGACAGCCCC
2361 TCCCCCTGCC TATGCCACCC TGGGCCCCCG CCCATCTCCA
2401 GGGGGCTCTG CAGGGGCCAG TTCCTCCACC TGTCCTCTGG
2441 GGGGGCCCTG AGAGGGAAGG AGAGGTTTCT CACACCAAGG
2481 CAGATGCTCC TCTGGTGGGA GGGTGCTGGC CCTGGCAAGA
2521 TTGAAGGATG TGCAGGGCTT CCTCTCAGAG CCGCCCAAAC
2561 TGCCGTTGAT GTGTGGAGGG GAAGCAAGAT GGGTAAGGGC
2601 TCAGGAAGTT GCTCCAAGAA CAGTAGCTGA TGAAGCTGCC
2641 CAGAAGTGCC TTGGCTCCAG CCCTGTACCC CTTGGTACTG
2681 CCTCTGAACA CTCTGGTTTC CCCACCCAAC TGCGGCTAAG
2721 TCTCTTTTTC CCTTGGATCA GCCAAGCGAA ACTTGGAGCT
2761 TTGACAAGGA ACTTTCCTAA GAAACCGCTG ATAACCAGGA
2801 CAAAACACAA CCAAGGGTAC ACGCAGGCAT GCACGGGTTT
2841 CCTGCCCAGC GACGGCTTAA GCCAGCCCCC GACTGGCCTG
2881 GCCACACTGC TCTCCAGTAG CACAGATGTC TGCTCCTCCT
2921 CTTGAACTTG GGTGGGAAAC CCCACCCAAA AGCCCCCTTT
2961 GTTACTTAGG CAATTCCCCT TCCCTGACTC CCGAGGGCTA
3001 GGGCTAGAGC AGACCCGGGT AAGTAAAGGC AGACCCAGGG
3041 CTCCTCTAGC CTCATACCCG TGCCCTCACA GAGCCATGCC
3081 CCGGCACCTC TGCCCTGTGT CTTTCATACC TCTACATGTC
3121 TGCTTGAGAT ATTTCCTCAG CCTGAAAGTT TCCCCAACCA
3161 TCTGCCAGAG AACTCCTATG CATCCCTTAG AACCCTGCTC
3201 AGACACCATT ACTTTTGTGA ACGCTTCTGC CACATCTTGT
3241 CTTCCCCAAA ATTGATCACT CCGCCTTCTC CTGGGCTCCC
3281 GTAGCACACT ATAACATCTG CTGGAGTGTT GCTGTTGCAC
3321 CATACTTTCT TGTACATTTG TGTCTCCCTT CCCAACTAGA
3361 CTGTAAGTGC CTTGCGGTCA GGGACTGAAT CTTGCCCGTT
3401 TATGTATGCT CCATGTCTAG CCCATCATCC TGCTTGGAGC
3441 AAGTAGGCAG GAGCTCAATA AATGTTTGTT GCATGAAGGA
3481 AAAAAAAAAA AAAAAAA
```

The rs2228576 single nucleotide polymorphism (SNP) is present in the SCNN1A gene, where the variable nucleotide is at about position 2428 in SEQ ID NO:21 (underlined), which can be adenine in some individuals and guanine in others. The rs2228576 sequence (SEQ ID NO:22) is shown below, where the underlined A/G is the SNP.

```
GGGCTCTGCAGGGGCCAGTTCCTCC[A/G]CCTGTCCTCTGGGGGGGCCC
TGAGA
```

Another cDNA sequence for the human SCNN1A gene with the same SNP is available from the NCBI database as accession number NM_001038.5 (GI: 227430285). This sequence is provided below as SEQ ID NO:24.

```
   1 CTTGCCTGTC TGCGTCTAAA GCCCCTGCCC AGAGTCCGCC
  41 TTCTCAGGTC CAGTACTCCC AGTTCACCTG CCCTCGGGAG
  81 CCCTCCTTCC TTCGGAAAAC TCCCGGCTCT GACTCCTCCT
 121 CAGCCCCTCC CCCCGCCCTG CTCACCTTTA ATTGAGATGC
 161 TAATGAGATT CCTGTCGCTT CCATCCCTGG CCGGCCAGCG
 201 GGCGGGCTCC CCAGCCAGGC CGCTGCACCT GTCAGGGGAA
 241 CAAGCTGGAG GAGCAGGACC CTAGACCTCT GCAGCCCATA
 281 CCAGGTCTCA TGGAGGGGAA CAAGCTGGAG GAGCAGGACT
 321 CTAGCCCTCC ACAGTCCACT CCAGGGCTCA TGAAGGGGAA
 361 CAAGCGTGAG GAGCAGGGGC TGGGCCCCGA ACCTGCGGCG
 401 CCCCAGCAGC CCACGGCGGA GGAGGAGGCC CTGATCGAGT
 441 TCCACCGCTC CTACCGAGAG CTCTTCGAGT TCTTCTGCAA
 481 CAACACCACC ATCCACGGCG CCATCCGCCT GGTGTGCTCC
 521 CAGCACAACC GCATGAAGAC GGCCTTCTGG GCAGTGCTGT
 561 GGCTCTGCAC CTTTGGCATG ATGTACTGGC AATTCGGCCT
 601 GCTTTTCGGA GAGTACTTCA GCTACCCCGT CAGCCTCAAC
 641 ATCAACCTCA ACTCGGACAA GCTCGTCTTC CCCGCAGTGA
 681 CCATCTGCAC CCTCAATCCC TACAGGTACC CGGAAATTAA
 721 AGAGGAGCTG GAGGAGCTGG ACCGCATCAC AGAGCAGACG
 761 CTCTTTGACC TGTACAAATA CAGCTCCTTC ACCACTCTCG
 801 TGGCCGGCTC CCGCAGCCGT CGCGACCTGC GGGGGACTCT
 841 GCCGCACCCC TTGCAGCGCC TGAGGGTCCC GCCCCCGCCT
 881 CACGGGGCCC GTCGAGCCCG TAGCGTGGCC TCCAGCTTGC
 921 GGGACAACAA CCCCCAGGTG GACTGGAAGG ACTGGAAGAT
 961 CGGCTTCCAG CTGTGCAACC AGAACAAATC GGACTGCTTC
1001 TACCAGACAT ACTCATCAGG GGTGGATGCG GTGAGGGAGT
1041 GGTACCGCTT CCACTACATC AACATCCTGT CGAGGCTGCC
1081 AGAGACTCTG CCATCCCTGG AGGAGGACAC GCTGGGCAAC
1121 TTCATCTTCG CCTGCCGCTT CAACCAGGTC TCCTGCAACC
1161 AGGCGAATTA CTCTCACTTC CACCACCCGA TGTATGGAAA
1201 CTGCTATACT TTCAATGACA AGAACAACTC CAACCTCTGG
1241 ATGTCTTCCA TGCCTGGAAT CAACAACGGT CTGTCCCTGA
1281 TGCTGCGCGC AGAGCAGAAT GACTTCATTC CCCTGCTGTC
1321 CACAGTGACT GGGGCCCGGG TAATGGTGCA CGGGCAGGAT
1361 GAACCTGCCT TTATGGATGA TGGTGGCTTT AACTTGCGGC
1401 CTGGCGTGGA GACCTCCATC AGCATGAGGA AGGAAACCCT
1441 GGACAGACTT GGGGGCGATT ATGGCGACTG CACCAAGAAT
1481 GGCAGTGATG TTCCTGTTGA GAACCTTTAC CCTTCAAAGT
```

-continued

```
1521 ACACACAGCA GGTGTGTATT CACTCCTGCT TCCAGGAGAG
1561 CATGATCAAG GAGTGTGGCT GTGCCTACAT CTTCTATCCG
1601 CGGCCCCAGA ACGTGGAGTA CTGTGACTAC AGAAAGCACA
1641 GTTCCTGGGG GTACTGCTAC TATAAGCTCC AGGTTGACTT
1681 CTCCTCAGAC CACCTGGGCT GTTTCACCAA GTGCCGGAAG
1721 CCATGCAGCG TGACCAGCTA CCAGCTCTCT GCTGGTTACT
1761 CACGATGGCC CTCGGTGACA TCCCAGGAAT GGGTCTTCCA
1801 GATGCTATCG CGACAGAACA ATTACACCGT CAACAACAAG
1841 AGAAATGGAG TGGCCAAAGT CAACATCTTC TTCAAGGAGC
1881 TGAACTACAA AACCAATTCT GAGTCTCCCT CTGTCACGAT
1921 GGTCACCCTC CTGTCCAACC TGGGCAGCCA GTGGAGCCTG
1961 TGGTTCGGCT CCTCGGTGTT GTCTGTGGTG GAGATGGCTG
2001 AGCTCGTCTT TGACCTGCTG GTCATCATGT TCCTCATGCT
2041 GCTCCGAAGG TTCCGAAGCC GATACTGGTC TCCAGGCCGA
2081 GGGGGCAGGG GTGCTCAGGA GGTAGCCTCC ACCCTGGCAT
2121 CCTCCCCTCC TTCCCACTTC TGCCCCCACC CCATGTCTCT
2161 GTCCTTGTCC CAGCCAGGCC CTGCTCCCTC TCCAGCCTTG
2201 ACAGCCCCTC CCCCTGCCTA TGCCACCCTG GGCCCCCGCC
2241 CATCTCCAGG GGGCTCTGCA GGGGCCAGTT CCTCCACCTG
2281 TCCTCTGGGG GGGCCCTGAG AGGGAAGGAG AGGTTTCTCA
2321 CACCAAGGCA GATGCTCCTC TGGTGGGAGG GTGCTGGCCC
2361 TGGCAAGATT GAAGGATGTG CAGGGCTTCC TCTCAGAGCC
2401 GCCCAAACTG CCGTTGATGT GTGGAGGGGA AGCAAGATGG
2441 GTAAGGGCTC AGGAAGTTGC TCCAAGAACA GTAGCTGATG
2481 AAGCTGCCCA GAAGTGCCTT GGCTCCAGCC CTGTACCCCT
2521 TGGTACTGCC TCTGAACACT CTGGTTTCCC CACCCAACTG
2561 CGGCTAAGTC TCTTTTTCCC TTGGATCAGC CAAGCGAAAC
2601 TTGGAGCTTT GACAAGGAAC TTTCCTAAGA AACCGCTGAT
2641 AACCAGGACA AAACACAACC AAGGGTACAC GCAGGCATGC
2681 ACGGGTTTCC TGCCCAGCGA CGGCTTAAGC CAGCCCCCGA
2721 CTGGCCTGGC CACACTGCTC TCCAGTAGCA CAGATGTCTG
2761 CTCCTCCTCT TGAACTTGGG TGGGAAACCC CACCCAAAAG
2801 CCCCCTTTGT TACTTAGGCA ATTCCCCTTC CCTGACTCCC
2841 GAGGGCTAGG GCTAGAGCAG ACCCGGGTAA GTAAAGGCAG
2881 ACCCAGGGCT CCTCTAGCCT CATACCCGTG CCCTCACAGA
2921 GCCATGCCCC GGCACCTCTG CCCTGTGTCT TTCATACCTC
2961 TACATGTCTG CTTGAGATAT TTCCTCAGCC TGAAAGTTTC
3001 CCCAACCATC TGCCAGAGAA CTCCTATGCA TCCCTTAGAA
3041 CCCTGCTCAG ACACCATTAC TTTTGTGAAC GCTTCTGCCA
3081 CATCTTGTCT TCCCCAAAAT TGATCACTCC GCCTTCTCCT
```

-continued

```
3121 GGGCTCCCGT AGCACACTAT AACATCTGCT GGAGTGTTGC
3161 TGTTGCACCA TACTTTCTTG TACATTTGTG TCTCCCTTCC
3201 CAACTAGACT GTAAGTGCCT TGCGGTCAGG GACTGAATCT
3241 TGCCCGTTTA TGTATGCTCC ATGTCTAGCC CATCATCCTG
3281 CTTGGAGCAA GTAGGCAGGA GCTCAATAAA TGTTTGTTGC
3321 ATGAAGGAAA AAAAAAAAAA AAAAA
```

A cDNA sequence for the human alpha adducin gene (ADD1) is available from the NCBI database as accession number NM_001119.4 (GI: 346644753). This ADD1 sequence is provided below as SEQ ID NO:26.

```
   1 GCACCCAGGT CGGGCGGTGG GGGCGAGCGG AGGGGCTGAG
  41 GGGCGGAGAG GCCTGGCGGG CCGCTGCTGC GGGCCAGGGG
  81 ACGGGGGCGG AGCCGGAGCC GGAGCCGACG GGCGGTGGCC
 121 GCACTGGGAC CCCGGAATCC CGCGCGCTGC CCACGATTCG
 161 CTTCTGAGGA ACCTAGAAAG ATTGTACAAT GAATGGTGAT
 201 TCTCGTGCTG CGGTGGTGAC CTCACCACCC CCGACCACAG
 241 CCCCTCACAA GGAGAGGTAC TTCGACCGAG TAGATGAGAA
 281 CAACCCAGAG TACTTGAGGG AGAGGAACAT GGCACCAGAC
 321 CTTCGCCAGG ACTTCAACAT GATGGAGCAA AAGAAGAGGG
 361 TGTCCATGAT TCTGCAAAGC CCTGCTTTCT GTGAAGAATT
 401 GGAATCAATG ATACAGGAGC AATTTAAGAA GGGGAAGAAC
 441 CCCACAGGCC TATTGGCATT ACAGCAGATT GCAGATTTTA
 481 TGACCACGAA TGTACCAAAT GTCTACCCAG CAGCTCCGCA
 521 AGGAGGGATG GCTGCCTTAA ACATGAGTCT TGGTATGGTG
 561 ACTCCTGTGA ACGATCTTAG AGGATCTGAT TCTATTGCGT
 601 ATGACAAAGG AGAGAAGTTA TTACGGTGTA AATTGGCAGC
 641 GTTTTATAGA CTAGCAGATC TCTTTGGGTG GTCTCAGCTT
 681 ATCTACAATC ATATCACAAC CAGAGTGAAC TCCGAGCAGG
 721 AACACTTCCT CATTGTCCCT TTTGGGCTTC TTTACAGTGA
 761 AGTGACTGCA TCCAGTTTGG TTAAGATCAA TCTACAAGGA
 801 GATATAGTAG ATCGTGGAAG CACTAATCTG GGAGTGAATC
 841 AGGCCGGCTT CACCTTACAC TCTGCAATTT ATGCTGCACG
 881 CCCGGACGTG AAGTGCGTCG TGCACATTCA CACCCCAGCA
 921 GGGGCTGCGG TCTCTGCAAT GAAATGTGGC CTCTTGCCAA
 961 TCTCCCCGGA GGCGCTTTCC CTTGGAGAAG TGGCTTATCA
1001 TGACTACCAT GGCATTCTGG TTGATGAAGA GGAAAAAGTT
1041 TTGATTCAGA AAAATCTGGG GCCTAAAAGC AAGGTTCTTA
1081 TTCTCCGGAA CCATGGGCTC GTGTCAGTTG GAGAGAGCGT
1121 TGAGGAGGCC TTCTATTACA TCCATAACCT TGTGGTTGCC
1161 TGTGAGATCC AGGTTCGAAC TCTGGCCAGT GCAGGAGGAC
1201 CAGACAACTT AGTCCTGCTG AATCCTGAGA AGTACAAAGC
```

-continued

```
1241 CAAGTCCCGT TCCCCAGGGT CTCCGGTAGG GGAAGGCACT
1281 GGATCGCCTC CCAAGTGGCA GATTGGTGAG CAGGAATTTG
1321 AAGCCCTCAT GCGGATGCTC GATAATCTGG GCTACAGAAC
1361 TGGCTACCCT TATCGATACC CTGCTCTGAG AGAGAAGTCT
1401 AAAAAATACA GCGATGTGGA GGTTCCTGCT AGTGTCACAG
1441 GTTACTCCTT TGCTAGTGAC GGTGATTCGG GCACTTGCTC
1481 CCCACTCAGA CACAGTTTTC AGAAGCAGCA GCGGGAGAAG
1521 ACAAGATGGC TGAACTCTGG CCGGGGCGAC GAAGCTTCCG
1561 AGGAAGGGCA GAATGGAAGC AGTCCCAAGT CGAAGACTAA
1601 GTGGACTAAA GAGGATGGAC ATAGAACTTC CACCTCTGCT
1641 GTCCCTAACC TGTTTGTTCC ATTGAACACT AACCCAAAAG
1681 AGGTCCAGGA GATGAGGAAC AAGATCCGAG AGCAGAATTT
1721 ACAGGACATT AAGACGGCTG GCCCTCAGTC CCAGGTTTTG
1761 TGTGGTGTAG TGATGGACAG GAGCCTCGTC CAGGGAGAGC
1801 TGGTGACGGC CTCCAAGGCC ATCATTGAAA AGGAGTACCA
1841 GCCCCACGTC ATTGTGAGCA CCACGGGCCC CAACCCCTTC
1881 ACCACACTCA CAGACCGTGA GCTGGAGGAG TACCGCAGGG
1921 AGGTGGAGAG GAAGCAGAAG GGCTCTGAAG AGAATCTGGA
1961 CGAGGCTAGA GAACAGAAAG AAAAGAGTCC TCCAGACCAG
2001 CCTGCGGTCC CCCACCCGCC TCCCAGCACT CCCATCAAGC
2041 TGGAGGAAGA CCTTGTGCCG GAGCCGACTA CTGGAGATGA
2081 CAGTGATGCT GCCACCTTTA AGCCAACTCT CCCCGATCTG
2121 TCCCCTGATG AACCTTCAGA AGCACTCGGC TTCCCAATGT
2161 TAGAGAAGGA GGAGGAAGCC CATAGACCCC CAAGCCCCAC
2201 TGAGGCCCCT ACTGAGGCCA GCCCCGAGCC AGCCCCAGAC
2241 CCAGCCCCGG TGGCTGAAGA GGCTGCCCCC TCAGCTGTCG
2281 AGGAGGGGGC CGCCGCGGAC CCTGGCAGCG ATGGGTCTCC
2321 AGGCAAGTCC CCGTCCAAAA AGAAGAAGAA GTTCCGTACC
2361 CCGTCCTTTC TGAAGAAGAG CAAGAAGAAG AGTGACTCCT
2401 GAAAGCCCTG CGCTAACACT GTCCTGTCCG GAGCGACCCT
2441 GGCTCTGCCA GCGTCCCCGG CCACGTCTGT GCTCTGTCCT
2481 TGTGTAATGG AATGCAAAAA AGCCAAGCCC TCCGCCTAGA
2521 GGTCCCCTCA CGTGACCAGC CCCGTGTAGC CCCGGGCTGA
2561 CCCAGTGTGT GCTCAGCAGC CCCACCCCAC CCTGCCCCTT
2601 GTCCTCTCAG AGCCTCAGCT TCTGGGGGAG ACATGCTCTC
2641 CCCACAGGGG GGAGGCACTA AGTCATGGTC CTGGCTGGAA
2681 GGTACTGAAG GCTTCTGCAG CTTTGGCTGC ACGTCACCCT
2721 CCTGAGCCTC ACCTTTCCTG CCGTCCCTCC TGTTGTGAAA
2761 TCACCACATT CTGTCTCTGC TTGGCTTCCC CTCCACCCTA
2801 AAGTCTCAGG TGACGGACTC AGACTCCTGG CTTCATGTGG
2841 CATTCTCTCT GCTCAGTGAT CTCACTTAAA TCTATATACA
```

-continued

```
2881 AAGCCTTGGT CCCGTGAAAA CACTCGTGTG CCCACCAGCG
2921 GCCTTGAAGA GGCAGGTCTG GGCCAGATGC TGGGCAGGAA
2961 ACCCCAGCGG CAGATGGGCC TGTGTGCACC CAACGTGATG
3001 CTATGCATGT CTGACCGACG ATCCCTCGAC CAGAATCAGA
3041 TTCAGGAGCT CAGTTTCTTT TTCACTTGGG TCTCTGGATT
3081 CCTGTCATAG GGAAGGTATA TCAGGAGGGG AAGAGGCCTT
3121 TCTAGAATTT TCTTTGAGCA GGTTTACAAT TTAGCTTACA
3161 TTTTTCGACT GTGAACGTGA ATAGGCTGCT TTTTGCTTTC
3201 TTCTTTCCAG ACCCCACAGT AGAGCACTTT TCACTTATTT
3241 GGGGGAGGCT TCAGGGGACT GTTCTCACCT TAACTCAGCC
3281 AGAAAGATGC CCTAGTTGTG ATCAAAGGTA ACTCGAGGTG
3321 GAGGGTAGCC CTGGGGCCCC TCGACATCAC CGTCATTGAT
3361 GGAGCCTGAA CCGTGTGCTC CTCGGCAGAT GCTGTTGTTG
3401 TTACTTCCCT CCAAGAGGCT GGAAAAGGGC TCAGAGCTGC
3441 TGAGCAGGAA CCGGAGGGTG ACCCATTTCA GGAGGTGCCG
3481 GTACCAGCCT GACTAGGTAC AGGCAAGCTT GTGTGGGCCC
3521 AACAGGCCCT TGGTAGAGCT GGTGCCAGAT GTGGGCTCAG
3561 ATCCTGGGCA TGATGGGCCG AGCCACCTCG GATCCCACTG
3601 ATTGGCCAGC CGAGCGAGAA CCAGGCTGCT GCATGGCACT
3641 GACCGCCGCT TCCAGCTTCC TCTGAGCCGC AGGGCCTGCT
3681 ACGCGGGCAA GCGTGCTGCC TCTCTTCTGT GTCGTTTTGT
3721 TGCCAAGGCA GAATGAAAAG TCCTTAACCG TGGACTCTTC
3761 CTTTATCCCC TCCTTTACCC CACATATGCA ATGACTTTTA
3801 ATTTTCACTT TTGTAGTTTA ATCCTTTGTA TTACAACATG
3841 AAATATAGTT GCATATATGG ACACCGACTT GGGAGGACAG
3881 GTCCTGAATG TCCTTTCTCC AGTGTAACAT GTTTTACTCA
3921 CAAATAAAAT TCTTTCAGCA AGTTCCTTGT CTAAAAAAAA
3961 AAAAAAAAAA
```

The rs4961 single nucleotide polymorphism (SNP) is present in the ADD1 gene, where the variable nucleotide is at about position 1566 in SEQ ID NO:26 (underlined), which can be guanine in some individuals and thymine in others. The rs4961 sequence (SEQ ID NO:27) is shown below, where the underlined G/T is the SNP.

```
CCGGGGCGACGAAGCTTCCGAGGAA[G/T]GGCAGAATGGAAGCAGTCCC
AAGTC
```

A cDNA sequence for the sodium ($Na^+$) chloride ($Cl^-$) co-transporter (SLC12A3) is available from the NCBI database as accession number NM_000339.2 (GI: 186910314). This SLC12A3 cDNA sequence is provided below as SEQ ID NO:29.

```
1 CTGGCCCCTC CCTGGACACC CAGGCGACAA TGGCAGAACT
41 GCCCACAACA GAGACGCCTG GGGACGCCAC TTTGTGCAGC
```

-continued

```
  81 GGGCGCTTCA CCATCAGCAC ACTGCTGAGC AGTGATGAGC
 121 CCTCTCCACC AGCTGCCTAT GACAGCAGCC ACCCCAGCCA
 161 CCTGACCCAC AGCAGCACCT TCTGCATGCG CACCTTTGGC
 201 TACAACACGA TCGATGTGGT GCCCACATAT GAGCACTATG
 241 CCAACAGCAC CCAGCCTGGT GAGCCCCGGA AGGTCCGGCC
 281 CACACTGGCT GACCTGCACT CCTTCCTCAA GCAGGAAGGC
 321 AGACACCTGC ATGCCCTGGC CTTTGACAGC CGGCCCAGCC
 361 ACGAGATGAC TGATGGGCTG GTGGAGGGCG AGGCAGGCAC
 401 CAGCAGCGAG AAGAACCCCG AGGAGCCAGT GCGCTTCGGC
 441 TGGGTCAAGG GGGTGATGAT TCGTTGCATG CTCAACATTT
 481 GGGGCGTGAT CCTCTACCTG CGGCTGCCCT GGATTACGGC
 521 CCAGGCAGGC ATCGTCCTGA CCTGGATCAT CATCCTGCTG
 561 TCGGTCACGG TGACCTCCAT CACAGGCCTC TCCATCTCAG
 601 CCATCTCCAC CAATGGCAAG GTCAAGTCAG GTGGCACCTA
 641 CTTCCTCATC TCCCGGAGTC TGGGCCCAGA GCTTGGGGGC
 681 TCCATCGGCC TCATTTTCGC TTTCGCCAAT GCCGTGGGTG
 721 TGGCCATGCA CACGGTGGGC TTTGCAGAGA CCGTGCGGGA
 761 CCTGCTCCAG GAGTATGGGG CACCCATCGT GGACCCCATT
 801 AACGACATCC GCATCATTGG CGTGGTCTCG GTCACTGTGC
 841 TGCTGGCCAT CTCCCTGGCT GGCATGGAGT GGGAGTCCAA
 881 GGCCCAGGTG CTGTTCTTCC TTGTCATCAT GGTCTCCTTT
 921 GCCAACTATT TAGTGGGGAC GCTGATCCCC CCATCTGAGG
 961 ACAAGGCCTC CAAAGGCTTC TTCAGCTACC GGGCGGACAT
1001 TTTTGTCCAG AACTTGGTGC CTGACTGGCG GGGTCCAGAT
1041 GGCACCTTCT TCGGAATGTT CTCCATCTTC TTCCCCTCGG
1081 CCACAGGCAT CCTGGCAGGG GCCAACATAT CTGGTGACCT
1121 CAAGGACCCT GCTATAGCCA TCCCCAAGGG GACCCTCATG
1161 GCCATTTTCT GGACGACCAT TTCCTACCTG GCCATCTCAG
1201 CCACCATTGG CTCCTGCGTG GTGCGTGATG CCTCTGGGGT
1241 CCTGAATGAC ACAGTGACCC CTGGCTGGGG TGCCTGCGAG
1281 GGGCTGGCCT GCAGCTATGG CTGGAACTTC ACCGAGTGCA
1321 CCCAGCAGCA CAGCTGCCAC TACGGCCTCA TCAACTATTA
1361 CCAGACCATG AGCATGGTGT CAGGCTTCGC GCCCCTGATC
1401 ACGGCTGGCA TCTTCGGGGC CACCCTCTCC TCTGCCCTGG
1441 CCTGCCTTGT CTCTGCTGCC AAAGTCTTCC AGTGCCTTTG
1481 CGAGGACCAG CTGTACCCAC TGATCGGCTT CTTCGGCAAA
1521 GGCTATGGCA AGAACAAGGA GCCCGTGCGT GGCTACCTGC
1561 TGGCCTACGC CATCGCTGTG GCCTTCATCA TCATCGCTGA
1601 GCTCAACACC ATAGCCCCCA TCATTTCCAA CTTCTTCCTC
1641 TGCTCCTATG CCCTCATCAA CTTCAGCTGC TTCCACGCCT
1681 CCATCACCAA CTCGCCTGGG TGGAGACCTT CATTCCAATA
1721 CTACAACAAG TGGGCGGCGC TGTTTGGGGC TATCATCTCC
1761 GTGGTCATCA TGTTCCTCCT CACCTGGTGG GCGGCCCTCA
1801 TCGCCATTGG CGTGGTGCTC TTCCTCCTGC TCTATGTCAT
1841 CTACAAGAAG CCAGAGGTAA ATTGGGGCTC CTCGGTACAG
1881 GCTGGCTCCT ACAACCTGGC CCTCAGCTAC TCGGTGGGCC
1921 TCAATGAGGT GGAAGACCAC ATCAAGAACT ACCGCCCCCA
1961 GTGCCTGGTG CTCACGGGGC CCCCCAACTT CCGCCCGGCC
2001 CTGGTGGACT TTGTGGGCAC CTTCACCCGG AACCTCAGCC
2041 TGATGATCTG TGGCCACGTG CTCATCGGAC CCCACAAGCA
2081 GAGGATGCCT GAGCTCCAGC TCATCGCCAA CGGGCACACC
2121 AAGTGGCTGA ACAAGAGGAA GATCAAGGCC TTCTACTCGG
2161 ATGTCATTGC CGAGGACCTC CGCAGAGGCG TCCAGATCCT
2201 CATGCAGGCC GCAGGTCTCG GGAGAATGAA GCCCAACATT
2241 CTGGTGGTTG GGTTCAAGAA GAACTGGCAG TCGGCTCACC
2281 CGGCCACAGT GGAAGACTAC ATTGGCATCC TCCATGATGC
2321 CTTTGATTTC AACTATGGCG TGTGTGTCAT GAGGATGCGG
2361 GAGGGACTCA ACGTGTCCAA GATGATGCAG GCGCACATTA
2401 ACCCCGTGTT TGACCCAGCG GAGGACGGGA AGGAAGCCAG
2441 CGCCAGAGGT GCCAGGCCAT CAGTCTCTGG CGCTTTGGAC
2481 CCCAAGGCCC TGGTGAAGGA GGAGCAGGCC ACCACCATCT
2521 TCCAGTCGGA GCAGGGCAAG AAGACCATAG ACATCTACTG
2561 GCTCTTTGAC GATGGAGGCC TCACCCTCCT CATTCCCTAT
2601 CTCCTTGGCC GCAAGAGGAG GTGGAGCAAA TGCAAGATCC
2641 GTGTGTTCGT AGGCGGCCAG ATTAACAGGA TGGACCAGGA
2681 GAGAAAGGCG ATCATTTCTC TGCTGAGCAA GTTCCGACTG
2721 GGATTCCATG AAGTCCACAT CCTCCCTGAC ATCAACCAGA
2761 ACCCTCGGGC TGAGCACACC AAGAGGTTTG AGGACATGAT
2801 TGCACCCTTC CGTCTGAATG ATGGCTTCAA GGATGAGGCC
2841 ACTGTCAACG AGATGCGGCG GGACTGCCCC TGGAAGATCT
2881 CAGATGAGGA GATTACGAAG AACAGAGTCA AGTCCCTTCG
2921 GCAGGTGAGG CTGAATGAGA TTGTGCTGGA TTACTCCCGA
2961 GACGCTGCTC TCATCGTCAT CACTTTGCCC ATAGGGAGGA
3001 AGGGGAAGTG CCCCAGCTCG CTGTACATGG CCTGGCTGGA
3041 GACCCTGTCC CAGGACCTCA GACCTCCAGT CATCCTGATC
3081 CGAGGAAACC AGGAAAACGT GCTCACCTTT TACTGCCAGT
3121 AACTCCAGGC TTTGACATCC CTGTCCACAG CTCTGAGTGT
3161 GTGGGATAAG TTGGAACTTG ATTGCCTCTA GTCCACAGGG
3201 ATGAGACTCA TGTTCTGTTG CACTTTAAGT GGCAGCATCT
3241 GATGATCTCA CCGAAAAAGA TGGTAGATTT CCAAATCTGG
3281 CTGGACTCCA CTTCCATGGG ACACATTCCC TGGGTCTTGT
```

-continued

```
3321 GTTTATAGGC TAGAGAAATA GCAGATGGAG CTGCAAGGAA
3361 AACTCTCTAA AGCATCCTAT TCCTTTTAAA GGATTTCTTT
3401 TGATTTTGAT GACCATTAAT TAAGAGTTCA GTCTTTGATT
3441 TGTATGCAAA TTGGAGTCCC AATGCTGGGC GTGAATCTTG
3481 ACAGTTTCTA CAGACCTTCC TGGGTGAAAG TTCCTAAATC
3521 ATGCCCTGCT TCCTCCAATA GGAGAATGGG AGCCTCACCT
3561 GTAGGACCTA CAGGCTCTCT AAGGAATGCA GGTCTCTCTC
3601 TGAGCCTCCA CAGCCAGGCA AATACATATA TATATATTTT
3641 TTTTTTAGAT GAAGTTTTTT CTCTTGTTGC CCAGGCTAGG
3681 GTGTAATGGC ATGATCTCAG GTCACTGCAA CCTCCTCCCG
3721 GGTTCAAGCA TTTCTTCTGT CTCAGCCTCC CGAATAGCTG
3761 GGATTACAGG CACCTGCCAT CACACGAGCT AATTTTTGTA
3801 TTTTTAGTAG AGATGGGGTT TCACCATGTT GACCAGGCTG
3841 GTGTTGAGCT CCTGACCTCA GGTGATCCAC CCACCTCGGT
3881 CTCCCAAAGT GCTGGGGTTA CAGGCCTGAG CCACTGCGCC
3921 CGGCCCAGGC AAATTTCTTG AACCACTTCT CACTCCCGTC
3961 ACTTTCAATA AGGGGTCTTT GATGTCTTCA CTGGTTCTTT
4001 GGACGAGGGA CTTTTCGAAC TTTTTTGGTT GCAACACACA
4041 GTAAGAAATA TACTTCACAC TGAGACTTGC AGCGCACACA
4081 CACGGAAACG ACCAAAACAA AAATGTCACA AAACAATACT
4121 TACCCTTCCC TGGGGGACGT CCTCCAGTAT GTTCTGTTCT
4161 GTTTATTTTT CACTGTTGGT TGCAATCCAA TAAAATGACT
4201 TTGGGATCCA CTCATGGGTG GGGACCCACA CATTTGAAAG
4241 GCATGGCCAC CTTTCTGTTG TGCCTTGCAT TTGTCCACAC
4281 ACAGGGAGTC TGGCTGAGCT GGGGAAAGGC CACGGCTGGG
4321 TGTCATTGCC ATTTTCCCAG CTCATCTCAC CGGGAAGAAA
4361 AGCAGATTGA CAGAACACGT GAGGAGGGGT ATTGATGGCA
4001 GGAGAGTCAA AAAAGAGTTT TAAAGAAGGG GCAAGGTTGA
4441 AGGAGTCTAG TGGCAAGGGT AAGATTTCAG GCATGGTTAA
4481 GAACAGACGA CAAGGATGTC AGGAATGAAG ATGTGGAGAG
4521 GGGTGTAGAG ATGGCAAGGT TGGCAAGGAA CAGATAGGCA
4561 GGAGCAGGTC CAAGCCAAGC CTAGCCCAAG ACCAGGTGAA
4601 AGGAGAGGGG AGGAGGAGCC ACCTGCAAGA GATGGAAAGA
4641 GCAGGCGGCA GAGGGGGCTG GCAGGGAGGG GCTGTTAAGA
4681 GTGGGGTTGG AGGTGGGAGA GAAGCTAGGA CAAGGGAGAT
4721 GGAGAAAGGA CCTATACCTG GCTCACGGAA GGCCTTCAGG
4761 TCACTACACG TTGAACATCC CCAGTGTTTG AGCCCCCAAA
4801 GCTAGGGTGC AAGAGCACTG CCATCGAATG CCAGTGGGTG
4841 AGGCCAAGTG AGGGTATTTG CAGCTCTAGA CATAACCAAG
4881 AAGCGTAAAG GTGAGTTGTT TGGTGGTACG ACTGCCTGTG
```

-continued

```
4921 CCTTCTTCCG ATGGCACTGG GGTGGCTGAA GGAACAGACA
4961 TCTTTGGGTT TCATCAGCCT CCTCCAAGAC TGCTGCAGTG
5001 CCTACACTTT AGACTTCAGA AGGAGACTAA AGACTTCTAG
5041 AATTTAGAAG GAGATCTGAA GTCTCCTTTC TGGAGTTACA
5081 ACCCAAAGGA TGTTAGCATT TCTCAGGTCA TCCCACTGCA
5121 AAGCCCAGAA GGCTTGGGGC TCCCAGGCTG CTCTGAAGCC
5161 CCACTGTCTG ACCGCCTCAG GGCTTGCTAC GAGGGACTGG
5201 GGCACGGCCA AGCTGACTAG GAACAGCTCT CGTGCTCCTG
5241 AGGGACCTGG AGGATGGGCC TGCCTCCCAG CCATTGAGCT
5281 GGATTCTGGG ATAATTCTTA ACTCGAAATA AGGGGAAGCA
5321 TCCATCAGGG AATGCTGGCC TTTCTAGAGC CACGTAGAAA
5361 ACAATTTTCT GGTTCTTCAA ACCTCAAAGA GTCCTTGGTC
5401 CAAAAAACAG AATGTTTTGG CTTCGGGTGT CAAAAAAAAA
5441 ATTTTCACGA TGTCAGAAAT AGTATGTTTT TAACAATAGT
5481 AATAGCTTTG TAAAAAAATA AAAAGCTTTA ACAGCGAGGC
5521 CATAAACAAT GAAATGAATA AAAACGGTGG TCATTCAGTC
5561 AACGGAAAAA AAAAAAAAAA AA
```

The rs1529927 single nucleotide polymorphism (SNP) is present in the SLC12A3 gene, where the variable nucleotide is at about position 820 in SEQ ID NO:29 (underlined), which can be guanine in some individuals and cytosine in others. The rs1529927 sequence (SEQ ID NO:30) is shown below, where the underlined C/G is the SNP.

CCCATTAACGACATCCGCATCATTG[<u>C/G</u>]CGTGGTCTCGGTCACTGTGC
TGCTG.

The rs2107614 single nucleotide polymorphism (SNP) is present in an intron of the WNK1 gene, where the variable nucleotide can be thymine in some individuals and cytosine in others. The rs2107614 sequence (SEQ ID NO:33) is shown below, where the underlined C/T is the SNP.

CACTTCCTCCAAAAAAAAAGAAAAC[<u>C/T</u>]CCATTTCCCCTCAACTCTTC
CAGTT.

Another SNP, rs1159744, is present an intron of the WNK1 gene, where the variable nucleotide can be guanine in some individuals and cytosine in others. The rs1159744 sequence (SEQ ID NO: 34) is shown below, where the underlined C/G is the SNP.

AATGTTAACAGTATAGAAAATTTTA[<u>C/G</u>]CTCAACAAATAGAGAATATC
AGTAA.

A full length human adrenoceptor alpha 2A (ADRA2A) cDNA nucleotide sequence is available from the database maintained by the National Center for Biotechnology Information (see website at ncbi.nlm.nih.gov), which has accession number NM_000681.3 and which is shown below as SEQ ID NO:50.

-continued

```
1 CAGCAGCAGC TCCAGCTCGG TGCAGAAGCC CAGCAGCCGG
41 CGTGCCGCCG CCCGGCCACT CCAGCGCCTT CTTCCCCGCC
81 TTGCGCTCCT GCCCCAACTC GCGCTGTCGT CGGACCCCGG
121 CCCATCCAGC AGCGCTCGGC GCCCACCAGG CGGACGCCCA
161 GGAGAACCCC TGCCTCCGTC GCGGCTCCTG GAGAGCTGAT
201 CGTTCACCTG CCCCGGCCCG CCTGAGGACG GGGGTGCCTT
241 CATGCGGCCC CCACACTCCT CACCCCGCCG CCGCCGCCGT
281 CCCGGAGCTC CGCACAGTGT GCCCCAGCCC CAGCAGGGCG
321 CACAACTTTG GAAGTCTCGC GGCGCTCCGA GAGGCGGCAG
361 AGTCCGCGCC CCAGCCCCGG GCCGGGCCGG GCCAGAACCG
401 CAGCGTCTGG GGGAAGCCAG AGAGTCGGTA ATCGCTTCGG
441 GGATGTAAGG CGACAGACAT AGGACCCCCG AGCTCGCATC
481 AGCACCCTTC GGCTGCCTCC CGGGGTGGGG GCGGGCCCCG
521 CACACGGTAA GACCTCTTGC TTTCGCTCAG GCTCAAGATT
561 CAAGATACAG ATATTGATAT GTATATATAT ATTTAATTTC
601 CTGTCATCCT TCCAAGTTAT CAGGCCACCG ATGATTTTTG
641 TTCTCCCTTC TTGAAGAATA AATCTCTCTT TACCCATCGG
681 CTCTCCCTAC TCTCTCCCGC CGCTTAGAAA TAAAACTTGG
721 CTGTATTAGG AGCTCGGAGC AAGAAGGCGC CCACCGAGAG
761 CGTCTGAAGC GCGAGCCAGG CGCAGTTCGC GGGACCCGGG
801 CCATGGGCCG CTAGCGGTCC TCCAGTTCGG GCCCGGCCTC
841 CCTGCGGCCC CCTCCCTATG TGAGCCGCAG CCAGGCGAGC
881 GGGGCGCCGG AGGAAGAGGA GGACCCACGG GCGCCGGGCC
921 GGAAGGCAGC TGGCAGCAGG CCCAGGCCAG CGGGCGCCCG
961 CGTTCATGTT CCGCCAGGAG CAGCCGTTGG CCGAGGGCAG
1001 CTTTGCGCCC ATGGGCTCCC TGCAGCCGGA CGCGGGCAAC
1041 GCGAGCTGGA ACGGGACCGA GGCGCCGGGG GGCGGCGCCC
1081 GGGCCACCCC TTACTCCCTG CAGGTGACGC TGACGCTGGT
1121 GTGCCTGGCC GGCCTGCTCA TGCTGCTCAC CGTGTTCGGC
1161 AACGTGCTCG TCATCATCGC CGTGTTCACG AGCCGCGCGC
1201 TCAAGGCGCC CCAAAACCTC TTCCTGGTGT CTCTGGCCTC
1241 GGCCGACATC CTGGTGGCCA CGCTCGTCAT CCCTTTCTCG
1281 CTGGCCAACG AGGTCATGGG CTACTGGTAC TTCGGCAAGG
1321 CTTGGTGCGA GATCTACCTG GCGCTCGACG TGCTCTTCTG
1361 CACGTCGTCC ATCGTGCACC TGTGCGCCAT CAGCCTGGAC
1401 CGCTACTGGT CCATCACACA GGCCATCGAG TACAACCTGA
1441 AGCGCACGCC GCGCCGCATC AAGGCCATCA TCATCACCGT
1481 GTGGGTCATC TCGGCCGTCA TCTCCTTCCC GCCGCTCATC
1521 TCCATCGAGA AGAAGGGCGG CGGCGGCGGC CCGCAGCCGG
1561 CCGAGCCGCG CTGCGAGATC AACGACCAGA AGTGGTACGT
1601 CATCTCGTCG TGCATCGGCT CCTTCTTCGC TCCCTGCCTC
1641 ATCATGATCC TGGTCTACGT GCGCATCTAC CAGATCGCCA
1681 AGCGTCGCAC CCGCGTGCCA CCCAGCCGCC GGGGTCCGGA
1721 CGCCGTCGCC GCGCCGCCGG GGGGCACCGA GCGCAGGCCC
1761 AACGGTCTGG GCCCCGAGCG CAGCGCGGGC CCGGGGGGCG
1801 CAGAGGCCGA ACCGCTGCCC ACCCAGCTCA ACGGCGCCCC
1841 TGGCGAGCCC GCGCCGGCCG GGCCGCGCGA CACCGACGCG
1881 CTGGACCTGG AGGAGAGCTC GTCTTCCGAC CACGCCGAGC
1921 GGCCTCCAGG GCCCCGCAGA CCCGAGCGCG GTCCCCGGGG
1961 CAAAGGCAAG GCCCGAGCGA GCCAGGTGAA GCCGGGCGAC
2001 AGCCTGCCGC GGCGCGGGCC GGGGGCGACG GGGATCGGGA
2041 CGCCGGCTGC AGGGCCGGGG GAGGAGCGCG TCGGGGCTGC
2081 CAAGGCGTCG CGCTGGCGCG GGCGGCAGAA CCGCGAGAAG
2121 CGCTTCACGT TCGTGCTGGC CGTGGTCATC GGAGTGTTCG
2161 TGGTGTGCTG GTTCCCCTTC TTCTTCACCT ACACGCTCAC
2201 GGCCGTCGGG TGCTCCGTGC CACGCACGCT CTTCAAATTC
2241 TTCTTCTGGT TCGGCTACTG CAACAGCTCG TTGAACCCGG
2281 TCATCTACAC CATCTTCAAC CACGATTTCC GCCGCGCCTT
2321 CAAGAAGATC CTCTGTCGGG GGACAGGAAA GCGGATCGTG
2361 TGAGGTTTCC GCTGGCGCCC GCGTAGACTC ACGCTGACTG
2401 CAGGCAGCGG GGGGCATCGA GGGGTGCTTA GCCCCAGGGC
2441 ACTCAGAAAC CCGGGCGCTG CCTGCTCTGC GTTTCCTCGT
2481 CTGGGGTGGC TCTGCAGCCT CCTGCGGGCG GGCGTCTGCT
2521 GCTCCTACAA GGGAAGCTTC TTGCTGCCAG GCCCACACAT
2561 CCCCAGTTGT TGGTTTGGCC ACTCTTGACC TGGAGCCATC
2601 TTCCTAGTGG GCCACCCCTA ATCACTATTG CTTCCTAAAG
2641 GTATTTTCAC CCTCTTCGCC TGGTACAGCC CTCACAGCTC
2681 TTCAGAGCAA GCACTGGACT ACAAGGGCAT GGCTCACAAA
2721 AGGTTAATGG ATGGGGGTTA CCTAGCCCTG GCTAATTCCC
2761 CTTCCATTCC CAACTCTCTC TCTCTTTTTA AAGAAAAATG
2801 CTAAGGGCAG CCCTGCCTGC CCTCCCCATC CCCCGCTGTA
2841 AATATACACT ATTTTTGATA GCACACATGG GGCCCCCATA
2881 TCTCTTGGCC TTGGTTTTGA TGTTGAAATC CTGGCCTTGG
2921 GAGAGATGCC TTCCAGGCAG ACACAGCTGT CTGGTTCAGG
2961 CCAAGCCCCT TTGCAATGCA AGCCCTTTCT GGTGTTATGA
3001 AGTCCCTCTA TGTCGTCGTT TTCACCAGCA ACTGGTGACT
3041 GTCCCTTCGA CACGGACCTG CTTTGAGATT TCCTGACAGG
3081 GAAAAGATTT CTGTCCATTT TTTTCCTGTG CCTAACAGCA
3121 TAATTGCCTT TTCCTATGTA AATATTATGA TGGTGGATCA
3161 AGACATAAGT AAATGAGCCT TTCTGCCTCA CATCAGCCCT
3201 GTGTATAAAG CCATTATTCT CTGATGCACT GTTTGCCCCA
```

-continued

3241 GTAACTCACT TTAAAACCTC TCTTTCCAGT GTTCCCTCTC

3281 TCCCTCCAGG GCCACTGCTT GAAGAAGAAT ATGTATGTTT

3321 CTATCTTGTA TGTCTGTGTG CCCCTCCTGC CCCGAAAGTG

3361 CTGACTATGG GGAAATCTTT TAGCTGCTGT TTTTAGACTC

3401 CAAGGAGTGG AAATTATGTG GAAGAAGCAA ACCTGATACA

3441 ATTTGCCCAA GGTAAACAGT TTGAAAAGAC AAATGGGCCT

3481 GCCAAACTGT ACAGTTTCTT CCCCAAGAGC TGTTAGGTAT

3521 CAAAATGTTG TCCTTTCCCC CCTCCGTGCT TTTCTGGTTG

3561 AGATCATGTC ATTGATGAAC TGCCAAAGTC AGGGGAGGAG

3601 GGCAGAGACT TTGTGTTTAC ATCTGCATTT CTACATGTTT

3641 TAGACAGAGA CAATTTAAGG CCTGCACTCT TATTTCACTA

3681 AAGAAAAACT AATGTCAGCA CATGTTGCTA ATGACAGTGG

3721 ATTTTTTTTT AAATAAAAAA GTTTACAGAT CAAATGTGAA

3761 ATAAATATGA ATGGAGTGGT CCTCTTGTCT GTTATCTGAG

3801 TTTTCAAAAG CTTTAAGACT CTGGGAACAT CTGATTTTAT

3841 GGATTTTTTA AAAATAAAAA ATGTACATTA TAAAAAAAAA

3881 AAAAAAAAA

A full length human adrenoceptor alpha 2C (ADRA2C) cDNA nucleotide sequence is available from the database maintained by the National Center for Biotechnology Information (see website at ncbi.nlm.nih.gov), which has accession number NM_000683.3 and which is shown below as SEQ ID NO:51.

1 CCGGCTCCAG GAGGGACGGC GTAGCTCGCG GGAGGACCAT

41 GGCGTCCCCG GCGCTGGCGG CGGCGCTGGC GGTGGCGGCA

81 GCGGCGGGCC CCAATGCGAG CGGCGCGGGC GAGAGGGGCA

121 GCGGCGGGGT TGCCAATGCC TCGGGGGCTT CCTGGGGGCC

161 GCCGCGCGGC CAGTACTCGG CGGGCGCGGT GGCAGGGCTG

201 GCTGCCGTGG TGGGCTTCCT CATCGTCTTC ACCGTGGTGG

241 GCAACGTGCT GGTGGTGATC GCCGTGCTGA CCAGCCGGGC

281 GCTGCGCGCG CCACAGAACC TCTTCCTGGT GTCGCTGGCC

321 TCGGCCGACA TCCTGGTGGC CACGCTGGTC ATGCCCTTCT

361 CGTTGGCCAA CGAGCTCATG GCCTACTGGT ACTTCGGGCA

401 GGTGTGGTGC GGCGTGTACC TGGCGCTCGA TGTGCTGTTT

441 TGCACCTCGT CGATCGTGCA TCTGTGTGCC ATCAGCCTGG

481 ACCGCTACTG GTCGGTGACG CAGGCCGTCG AGTACAACCT

521 GAAGCGCACA CCACGCCGCG TCAAGGCCAC CATCGTGGCC

561 GTGTGGCTCA TCTCGGCCGT CATCTCCTTC CCGCCGCTGG

601 TCTCGCTCTA CCGCCAGCCC GACGGCGCCG CCTACCCGCA

641 GTGCGGCCTC AACGACGAGA CCTGGTACAT CCTGTCCTCC

661 TGCATCGGCT CCTTCTTCGC GCCCTGCCTC ATCATGGGCC

721 TGGTCTACGC GCGCATCTAC CGAGTGGCCA AGCTGCGCAC

-continued

761 GCGCACGCTC AGCGAGAAGC GCGCCCCCGT GGGCCCCGAC

801 GGTGCGTCCC CGACTACCGA AAACGGGCTG GGCGCGGCGG

841 CAGGCGCAGG CGAGAACGGG CACTGCGCGC CCCCGCCCGC

881 CGACGTGGAG CCGGACGAGA GCAGCGCAGC GGCCGAGAGG

921 CGGCGGCGCC GGGGCGCGTT GCGGCGGGGC GGGCGGCGGC

961 GAGCGGGCGC GGAGGGGGGC GCGGGCGGTG CGGACGGGCA

1001 GGGGGCGGGG CCGGGGGCGG CTGAGTCGGG GGCGCTGACC

1041 GCCTCCAGGT CCCCGGGGCC CGGTGGCCGC CTGTCGCGCG

1081 CCAGCTCGCG CTCCGTCGAG TTCTTCCTGT CGCGCCGGCG

1121 CCGGGCGCGC AGCAGCGTGT GCCGCCGCAA GGTGGCCCAG

1161 GCGCGCGAGA AGCGCTTCAC CTTTGTGCTG GCTGTGGTCA

1201 TGGGCGTGTT CGTGCTCTGC TGGTTCCCCT TCTTCTTCAG

1241 CTACAGCCTG TACGGCATCT GCCGCGAGGC CTGCCAGGTG

1281 CCCGGCCCGC TCTTCAAGTT CTTCTTCTGG ATCGGCTACT

1321 GCAACAGCTC GCTCAACCCG GTCATCTACA CGGTCTTCAA

1361 CCAGGATTTC CGGCGATCCT TTAAGCACAT CCTCTTCCGA

1401 CGGAGGAGAA GGGGCTTCAG GCAGTGACTC GCACCCGTCT

1441 GGGAATCCTG GACAGCTCCG CGCTCGGGGC TGGGCAGAAG

1481 GGGCGGCCCG GACGGGGGAG CTTTCCCAGA GACCCGGGGA

1521 TGGATTGGCC TCCAGGGCGC AGGGGAGGGT GCGGCAGGGC

1561 AGGAGCTTGG CAGAGAGATA GCCGGGCTCC AGGGAGTGGG

1601 GAGGAGAGAG GGGGAGACCC CTTTGCCTTC CCCCCTCAGC

1641 AAGGGGCTGC TTCTGGGGCT CCCTGCCTGG ATCCAGCTCT

1681 GGGAGCCCTG CCGAGGTGTG GCTGTGAGGT CAGGGTTTTA

1721 GAGAGCAGTG GCAGAGGTAG CCCCCTAAAT GGGCAAGCAA

1761 GGAGCCCCCC AAAGACACTA CCACTCCCCA TCCCCGTCTG

1801 ACCAAGGGCT GACTTCTCCA GGACCTAGTC GGGGGGTGGC

1841 TGCCAGGGGG CAAGGAGAAA GCACCGACAA TCTTTGATTA

1881 CTGAAAGTAT TTAAATGTTT GCCAAAAACA ACAGCCAAAA

1921 CAACCAAACT ATTTTCTAAA TAAACCTTTG TAATCTAA

A full length human renin cDNA nucleotide sequence is available from the database maintained by the National Center for Biotechnology Information (see website at ncbi.nlm.nih.gov), which has accession number NM_000537.4 and which is shown below as SEQ ID NO:52.

1 AGAACCTCAG TGGATCTCAG AGAGAGCCCC AGACTGAGGG

41 AAGCATGGAT GGATGGAGAA GGATGCCTCG CTGGGGACTG

81 CTGCTGCTGC TCTGGGGCTC CTGTACCTTT GGTCTCCCGA

121 CAGACACCAC CACCTTTAAA CGGATCTTCC TCAAGAGAAT

161 GCCCTCAATC CGAGAAAGCC TGAAGGAACG AGGTGTGGAC

-continued

```
 201 ATGGCCAGGC TTGGTCCCGA GTGGAGCCAA CCCATGAAGA
 241 GGCTGACACT TGGCAACACC ACCTCCTCCG TGATCCTCAC
 281 CAACTACATG GACACCCAGT ACTATGGCGA GATTGGCATC
 321 GGCACCCCAC CCCAGACCTT CAAAGTCGTC TTTGACACTG
 361 GTTCGTCCAA TGTTTGGGTG CCCTCCTCCA AGTGCAGCCG
 401 TCTCTACACT GCCTGTGTGT ATCACAAGCT CTTCGATGCT
 441 TCGGATTCCT CCAGCTACAA GCACAATGGA ACAGAACTCA
 481 CCCTCCGCTA TTCAACAGGG ACAGTCAGTG GCTTTCTCAG
 521 CCAGGACATC ATCACCGTGG GTGGAATCAC GGTGACACAG
 561 ATGTTTGGAG AGGTCACGGA GATGCCCGCC TTACCCTTCA
 601 TGCTGGCCGA GTTTGATGGG GTTGTGGGCA TGGGCTTCAT
 641 TGAACAGGCC ATTGGCAGGG TCACCCCTAT CTTCGACAAC
 681 ATCATCTCCC AAGGGGTGCT AAAAGAGGAC GTCTTCTCTT
 721 TCTACTACAA CAGAGATTCC GAGAATTCCC AATCGCTGGG
 761 AGGACAGATT GTGCTGGGAG GCAGCGACCC CCAGCATTAC
 801 GAAGGGAATT TCCACTATAT CAACCTCATC AAGACTGGTG
 841 TCTGGCAGAT TCAAATGAAG GGGGTGTCTG TGGGGTCATC
 881 CACCTTGCTC TGTGAAGACG GCTGCCTGGC ATTGGTAGAC
 921 ACCGGTGCAT CCTACATCTC AGGTTCTACC AGCTCCATAG
 961 AGAAGCTCAT GGAGGCCTTG GGAGCCAAGA AGAGGCTGTT
1001 TGATTATGTC GTGAAGTGTA ACGAGGGCCC TACACTCCCC
1041 GACATCTCTT TCCACCTGGG AGGCAAAGAA TACACGCTCA
1081 CCAGCGCGGA CTATGTATTT CAGGAATCCT ACAGTAGTAA
1121 AAAGCTGTGC ACACTGGCCA TCCACGCCAT GGATATCCCG
1161 CCACCCACTG GACCCACCTG GGCCCTGGGG GCCACCTTCA
1201 TCCGAAAGTT CTACACAGAG TTTGATCGGC GTAACAACCG
1241 CATTGGCTTC GCCTTGGCCC GCTGAGGCCC TCTGCCACCC
1281 AGGCAGGCCC TGCCTTCAGC CCTGGCCCAG AGCTGGAACA
1321 CTCTCTGAGA TGCCCCTCTG CCTGGGCTTA TGCCCTCAGA
1361 TGGAGACATT GGATGTGGAG CTCCTGCTGG ATGCGTGCCC
1401 TGACCCCTGC ACCAGCCCTT CCCTGCTTTG AGGACAAAGA
1441 GAATAAAGAC TTCATGTTCA CA
```

A full length human WNK lysine deficient protein kinase 1 (WNK1; transcript variant 1) cDNA nucleotide sequence is available from the database maintained by the National Center for Biotechnology Information (see website at ncbi.nlm.nih.gov), which has accession number NM_018979.4 and which is shown below as SEQ ID NO:53.

```
   1 AGACTCCCGG CGCCATTTAG CGCGGAGAGT TTCCCGGGTG
  41 GACGCGGCTC CTCTCTCGGC CACTCCGCAC CCCCATCTTC
  81 GGTGACAGAA GGCGCCTGGT GGGGGTGGCT GCTCTTTTCT
```

-continued

```
 121 CTCCCTGTTC CCCCTCACCC AGTCCTCTAG GTCTCCTCTC
 161 CTCTTGCCTC AGAGAAGCAG CGGAGCTCGG GCCCCGCGGT
 201 GAGCGGCCCT CCCCTCCCCG CCGTTCCCTC CTCCGTCAGC
 241 CCCCGGCACC GGCCCGGGAG GAGACGGGTT TGCCAGGCCT
 281 GGGGCGGGCG GGGAGGCCTC GGGGAAGGGG GGGCCCGCTC
 321 CTCAGGCGCC GAGGCTCCGA GGCTCCGGCC CTTCGCCTCT
 361 GGGCGATGGG CGACCTGTGA GGCCGGTCCC CATCGCTGGG
 401 GGCGCGTGTG GGAGGAGGCG GCCGCCCGAG TGACCGGGAG
 441 CCGGGCCGCG GCCTTCCCTC GCCCGCCTCG GCCCCTCCCA
 481 CTCCTCTGCC CCGGGGCCGC CACCGCCCGG GCGTCGGACC
 521 TGGTCCCGTG CTCGCGGTGC CGCCGCCCTC TGGGCCTAGC
 561 CCGCCCAGCT CGGCGAGCGG CGGCAGTGGG AGCCGCGTCC
 601 GCCGCATCCG CCTCGACTCG GTGCCGGCCC CTGGCCCTCC
 641 CCTCATGACT GCGGCGCCTC TGCTGCCACC GCCCGCCCGG
 681 CCGCCGCTCG CCGCAGGATG GATGCGGACC GTGCGGCGCT
 721 AACCCCCGTG GCTCAGCTCC CGAATCGCCC GCCTTCGAGC
 761 CCTCCTCGTG AGCCGCAGCA GCCTCGGTGC CAGCCCCCGC
 801 CGCAGCTGGG CCCAGCGGTC CGCCTGTCCC TCGTTGCGGC
 841 TTGTCGGTGC TGAGTGAGGC GTCGTCCGGG TCGGCGCGAA
 881 CCCGCCCGGC CGCGGTTCCC TGCAGACCTC TGCGCGGGCG
 921 GCTCGGCCCT TCACGCCCTT TTCGTTCACG AATCCGAGCC
 961 CGCTCGCCTC TCTCCAGCGA ACCGACCATG TCTGGCGGCG
1001 CCGCAGAGAA GCAGAGCAGC ACTCCCGGTT CCCTGTTCCT
1041 CTCGCCGCCG GCTCCTGCCC CCAAGAATGG CTCCAGCTCC
1081 GATTCCTCCG TGGGGGAGAA ACTGGGAGCC GCGGCCGCCG
1121 ACGCTGTGAC CGGCAGGACC GAGGAGTACA GGCGCCGCCG
1161 CCACACTATG GACAAGGACA GCCGTGGGGC GGCCGCGACC
1201 ACTACCACCA CTGAGCACCG CTTCTTCCGC CGGAGCGTCA
1241 TCTGTGACTC CAATGCCACT GCACTGGAGC TTCCCGGCCT
1281 TCCTCTTTCC CTGCCCCAGC CCAGCATCCC CGCGGCTGTC
1321 CCGCAGAGTG CTCCACCGGA GCCCCACCGG GAAGAGACCG
1361 TGACCGCCAC CGCCACTTCC CAGGTAGCCC AGCAGCCTCC
1401 AGCCGCTGCC GCCCCTGGGG AACAGGCCGT CGCGGGCCCT
1441 GCCCCCTCGA CTGTCCCCAG CAGTACCAGC AAAGACCGCC
1481 CAGTGTCCCA GCCTAGCCTT GTGGGGAGCA AAGAGGAGCC
1521 GCCGCCGGCG AGAAGTGGCA GCGGCGGCGG CAGCGCCAAG
1561 GAGCCACAGG AGGAACGGAG CCAGCAGCAG GATGATATCG
1601 AAGAGCTGGA GACCAAGGCC GTGGGAATGT CTAACGATGG
1641 CCGCTTTCTC AAGTTTGACA TCGAAATCGG CAGAGGCTCC
1681 TTTAAGACGG TCTACAAAGG TCTGGACACT GAAACCACCG
1721 TGGAAGTCGC CTGGTGTGAA CTGCAGGATC GAAAATTAAC
```

-continued

```
1761 AAAGTCTGAG AGGCAGAGAT TTAAAGAAGA AGCTGAAATG
1801 TTAAAAGGTC TTCAGCATCC CAATATTGTT AGATTTTATG
1841 ATTCCTGGGA ATCCACAGTA AAAGGAAAGA AGTGCATTGT
1881 TTTGGTGACT GAACTTATGA CGTCTGGAAC ACTTAAAACG
1921 TATCTGAAAA GGTTTAAAGT GATGAAGATC AAAGTTCTAA
1961 GAAGCTGGTG CCGTCAGATC CTTAAAGGTC TTCAGTTTCT
2001 TCATACTCGA ACTCCACCTA TCATTCACCG CGATCTTAAA
2041 TGTGACAACA TCTTTATCAC CGGCCCTACT GGCTCAGTCA
2081 AGATTGGAGA CCTCGGTCTG GCAACCCTGA AGCGGGCTTC
2121 TTTTGCCAAG AGTGTGATAG GTACCCCAGA GTTCATGGCC
2161 CCTGAGATGT ATGAGGAGAA ATATGATGAA TCCGTTGACG
2201 TTTATGCTTT TGGGATGTGC ATGCTTGAGA TGGCTACATC
2241 TGAATATCCT TACTCGGAGT GCCAAAATGC TGCACAGATC
2281 TACCGTCGCG TGACCAGTGG GGTGAAGCCA GCCAGTTTTG
2321 ACAAAGTAGC AATTCCTGAA GTGAAGGAAA TTATTGAAGG
2361 ATGCATACGA CAAAACAAAG ATGAAAGATA TTCCATCAAA
2401 GACCTTTTGA ACCATGCCTT CTTCCAAGAG GAAACAGGAG
2441 TACGGGTAGA ATTAGCAGAA GAAGATGATG GAGAAAAAAT
2481 AGCCATAAAA TTATGGCTAC GTATTGAAGA TATTAAGAAA
2521 TTAAAGGGAA AATACAAAGA TAATGAAGCT ATTGAGTTTT
2561 CTTTTGATTT AGAGAGAGAT GTCCCAGAAG ATGTTGCACA
2601 AGAAATGGTA GAGTCTGGGT ATGTCTGTGA AGGTGATCAC
2641 AAGACCATGG CTAAAGCTAT CAAAGACAGA GTATCATTAA
2681 TTAAGAGGAA ACGAGAGCAG CGGCAGTTGG TACGGGAGGA
2721 GCAAGAAAAA AAAAAGCAGG AAGAGAGCAG TCTCAAACAG
2761 CAGGTAGAAC AATCCAGTGC TTCCCAGACA GGAATCAAGC
2801 AGCTCCCTTC TGCTAGCACC GGCATACCTA CTGCTTCTAC
2841 CACTTCAGCT TCAGTTTCTA CACAAGTAGA ACCTGAAGAA
2881 CCTGAGGCAG ATCAACATCA ACAACTACAG TACCAGCAAC
2921 CCAGTATATC TGTGTTATCT GATGGGACGG TTGACAGTGG
2961 TCAGGGATCC TCTGTCTTCA CAGAATCTCG AGTGAGCAGC
3001 CAACAGACAG TTTCATATGG TTCCCAACAT GAACAGGCAC
3041 ATTCTACAGG CACAGTCCCA GGGCATATAC CTTCTACTGT
3081 CCAAGCACAG TCTCAGCCCC ATGGGGTATA TCCACCCTCA
3121 AGTGTGGCAC AGGGGCAGAG CCAGGGTCAG CCATCCTCAA
3161 GTAGCTTAAC AGGGGTTTCA TCTTCCCAAC CCATACAACA
3401 TCCTCAGCAG CAGCAGGGAA TACAGCAGAC AGCCCCTCCT
3241 CAACAGACAG TGCAGTATTC ACTTTCACAG ACATCAACCT
3281 CCAGTGAGGC CACTACTGCA CAGCCAGTGA GTCAGCCTCA
3321 AGCTCCACAA GTCTTGCCTC AAGTATCAGC TGGAAAACAG
```

-continued

```
3361 CTTCCAGTTT CCCAGCCAGT ACCAACTATC CAAGGCGAAC
3401 CTCAGATCCC AGTTGCGACA CAACCCTCGG TTGTTCCAGT
3441 CCACTCTGGT GCTCATTTCC TTCCAGTGGG ACAGCCGCTC
3481 CCTACTCCCT TGCTCCCTCA GTACCCTGTC TCTCAGATTC
3521 CCATATCAAC TCCTCATGTG TCTACGGCTC AGACAGGTTT
3561 CTCATCCCTT CCCATCACAA TGGCAGCTGG CATTACTCAG
3601 CCTCTGCTCA CGTTGGCTTC ATCTGCTACA ACAGCTGCGA
3641 TCCCGGGGGT ATCAACTGTG GTTCCTAGTC AGCTTCCAAC
3681 CCTTCTGCAG CCTGTGACTC AGCTGCCAAG TCAGGTTCAC
3721 CCACAGCTCC TACAACCAGC AGTTCAGTCC ATGGGAATAC
3761 CAGCTAACCT TGGACAAGCT GCTGAGGTTC CACTTTCCTC
3801 TGGAGATGTT CTGTACCAGG GCTTCCCACC TCGACTGCCA
3841 CCACAGTACC CAGGAGATTC AAATATTGCT CCCTCTTCCA
3881 ACGTGGCTTC TGTTTGCATC CATTCTACAG TCCTATCCCC
3921 TCCCATGCCG ACAGAAGTAC TGGCTACACC TGGGTACTTT
3961 CCCACAGTGG TGCAGCCTTA TGTGGAATCA AATCTTTTAG
4001 TTCCTATGGG TGGTGTAGGA GGACAGGTTC AAGTGTCCCA
4041 GCCAGGAGGG AGTTTAGCAC AAGCCCCCAC TACATCCTCC
4081 CAGCAAGCAG TTTTGGAGAG TACTCAGGGA GTCTCTCAGG
4121 TTGCTCCTGC AGAGCCAGTT GCAGTAGCAC AGACCCAAGC
4161 TACCCAGCCG ACCACTTTGG CTTCCTCTGT AGACAGTGCA
4201 CATTCAGATG TTGCTTCAGG TATGAGTGAT GGCAATGAGA
4241 ACGTCCCATC TTCCAGTGGA AGGCATGAAG GAAGAACTAC
4281 AAAACGGCAT TACCGAAAAT CTGTAAGGAG TCGCTCTCGA
4321 CATGAAAAAA CTTCACGCCC AAAATTAAGA ATTTTGAATG
4361 TTTCAAATAA AGGAGACCGA GTAGTAGAAT GTCAATTAGA
4401 GACTCATAAT AGGAAAATGG TTACATTCAA ATTTGACCTA
4441 GATGGTGACA ACCCCGAGGA GATAGCAACA ATTATGGTGA
4481 ACAATGACTT TATTCTAGCA ATAGAGAGAG AGTCGTTTGT
4521 GGATCAAGTG CGAGAAATTA TTGAAAAAGC TGATGAAATG
4561 CTCAGTGAGG ATGTCAGTGT GGAACCAGAG GGTGATCAGG
4601 GATTGGAGAG TCTACAAGGA AAGGATGACT ATGGCTTTTC
4641 AGGTTCTCAG AAATTGGAAG GAGAGTTCAA ACAACCAATT
4681 CCTGCGTCTT CCATGCCACA GCAAATAGGC ATTCCTACCA
4721 GTTCTTTAAC TCAAGTTGTT CATTCTGCGG GAAGGCGGTT
4761 TATAGTGAGT CCTGTGCCAG AAAGCCGATT ACGAGAATCA
4801 AAAGTTTTCC CCAGTGAAAT AACAGATACA GTTGCTGCCT
4841 CTACAGCTCA GAGCCCTGGA ATGAACTTGT CTCACTCTGC
4881 ATCATCCCTT AGTCTACAAC AGGCCTTTTC TGAACTTAGA
4921 CGTGCCCAAA TGACAGAAGG ACCCAACACA GCACCTCCAA
4961 ACTTTAGTCA TACAGGACCA ACATTTCCAG TAGTACCTCC
```

-continued

```
5001 TTTCTTAAGT AGCATTGCTG GAGTCCCAAC CACAGCAGCA
5041 GCCACAGCAC CAGTCCCTGC AACAAGCAGC CCTCCTAATG
5081 ACATTTCCAC ATCAGTAATT CAGTCTGAGG TTACAGTGCC
5121 CACTGAAGAG GGGATTGCTG GAGTTGCCAC CAGCACAGGT
5161 GTGGTAACTT CAGGTGGTCT CCCCATACCA CCTGTGTCTG
5201 AATCACCAGT ACTTTCCAGC GTAGTTTCAA GTATCACAAT
5241 ACCTGCAGTT GTCTCAATAT CTACTACATC CCCGTCACTT
5281 CAAGTCCCCA CATCCACATC TGAGATCGTT GTTTCTAGTA
5321 CAGCACTGTA TCCTTCAGTA ACAGTTTCAG CAACTTCAGC
5361 CTCTGCAGGG GGCAGTACTG CTACCCCAGG TCCTAAGCCT
5401 CCAGCTGTAG TATCTCAGCA GGCAGCAGGC AGCACTACTG
5441 TGGGAGCCAC ATTAACATCA GTTTCTACCA CCACTTCATT
5481 CCCAAGCACA GCTTCACAGC TGTGCATTCA GCTTAGCAGC
5521 AGTACTTCTA CTCCTACTTT AGCTGAAACC GTGGTAGTTA
5561 GCGCACACTC ACTAGATAAG ACATCTCATA GCAGTACAAC
5601 TGGATTGGCT TTCTCCCTCT CTGCACCATC TTCCTCTTCC
5641 TCTCCTGGAG CAGGAGTGTC TAGTTATATT TCTCAGCCTG
5681 GTGGGCTGCA TCCTTTGGTC ATTCCATCAG TGATAGCTTC
5721 TACTCCTATT CTTCCCCAAG CAGCAGGACC TACTTCTACA
5761 CCTTTATTAC CCCAAGTACC TAGTATCCCA CCCTTGGTAC
5801 AGCCTGTTGC CAATGTGCCT GCTGTACAGC AGACACTAAT
5841 TCATAGTCAG CCTCAACCAG CTTTGCTTCC CAACCAGCCC
5881 CATACTCATT GTCCTGAAGT AGATTCTGAT ACACAACCCA
5921 AAGCTCCTGG AATTGATGAC ATAAAGACTC TAGAAGAAAA
5941 GCTGCGGTCT CTGTTCAGTG AACACAGCTC ATCTGGAGCT
6001 CAGCATGCCT CTGTCTCACT GGAGACCTCA CTAGTCATAG
6041 AGAGCACTGT CACACCAGGC ATCCCAACTA CTGCTGTTGC
6081 ACCAAGCAAA CTCCTGACTT CTACCACAAG TACTTGCTTA
6121 CCACCAACCA ATTTACCACT AGGAACAGTT GCTTTGCCAG
6161 TTACACCAGT GGTCACACCT GGGCAAGTTT CTACCCCAGT
6201 CAGCACTACT ACATCAGGAG TGAAACCTGG AACTGCTCCC
6241 TCCAAGCCAC CTCTAACTAA GGCTCCGGTG CTGCCAGTGG
6281 GTACTGAACT TCCAGCAGGT ACTCTACCCA GCGAGCAGCT
6321 GCCACCTTTT CCAGGACCTT CTCTAACCCA GTCCCAGCAA
6361 CCTCTAGAGG ATCTTGATGC TCAATTGAGA AGAACACTTA
6401 GTCCAGAGAT GATCACAGTG ACTTCTGCGG TTGGTCCTGT
6481 GTCCATGGCG GCTCCAACAG CAATCACAGA AGCAGGAACA
6481 CAGCCTCAGA AGGGTGTTTC TCAAGTCAAA GAAGGCCCTG
6521 TCCTAGCAAC TAGTTCAGGA GCTGGTGTTT TTAAGATGGG
6561 ACGATTTCAG GTTTCTGTTG CAGCAGACGG TGCCCAGAAA
```

-continued

```
6601 GAGGGTAAAA ATAAGTCAGA AGATGCAAAG TCTGTTCATT
6641 TTGAATCCAG CACCTCAGAG TCCTCAGTGC TATCAAGTAG
6681 TAGTCCAGAG AGTACCTTGG TGAAACCAGA GCCGAATGGC
6721 ATAACCATCC CTGGTATCTC TTCAGATGTG CCAGAGAGTG
6761 CCCACAAAAC TACTGCCTCA GAGGCAAAGT CAGACACTGG
6801 GCAGCCTACC AAGGTTGGAC GTTTTCAGGT GACAACTACA
6841 GCAAACAAAG TGGGTCGTTT CTCTGTATCA AAAACTGAGG
6881 ACAAGATCAC TGACACAAAG AAAGAAGGAC CAGTGGCATC
6921 TCCTCCTTTT ATGGATTTGG AACAAGCTGT TCTTCCTGCT
6961 GTGATACCAA AGAAAGAGAA GCCTGAACTG TCAGAGCCTT
7001 CACATCTAAA TGGGCCGTCT TCTGACCCGG AGGCCGCTTT
7041 TTTAAGTAGG GATGTGGATG ATGGTTCCGG TAGTCCACAC
7081 TCGCCCCATC AGCTGAGCTC AAAGAGCCTT CCTAGCCAGA
7121 ATCTAAGTCA AAGCCTTAGT AATTCATTTA ACTCCTCTTA
7161 CATGAGTAGC GACAATGAGT CAGATATCGA AGATGAAGAC
7201 TTAAAGTTAG AGCTGCGACG ACTACGAGAT AAACATCTCA
7241 AAGAGATTCA GGACCTGCAG AGTCGCCAGA AGCATGAAAT
7281 TGAATCTTTG TATACCAAAC TGGGCAAGGT GCCCCCTGCT
7321 GTTATTATTC CCCCAGCTGC TCCCCTTTCA GGGAGAAGAC
7361 GACGACCCAC TAAAAGCAAA GGCAGCAAAT CTAGTCGAAG
7401 CAGTTCCTTG GGGAATAAAA GCCCCCAGCT TTCAGGTAAC
7441 CTGTCTGGTC AGAGTGCAGC TTCAGTCTTG CACCCCCAGC
7481 AGACCCTCCA CCCTCCTGGC AACATCCCAG AGTCCGGGCA
7521 GAATCAGCTG TTACAGCCCC TTAAGCCATC TCCCTCCAGT
7561 GACAACCTCT ATTCAGCCTT CACCAGTGAT GGTGCCATTT
7600 CAGTACCAAG CCTTTCTGCT CCAGGTCAAG GAACCAGCAG
7641 CACAAACACT GTTGGGGCAA CAGTGAACAG CCAAGCCGCC
7681 CAAGCTCAGC CTCCTGCCAT GACGTCCAGC AGGAAGGGCA
7721 CATTCACAGA TGACTTGCAC AAGTTGGTAG ACAATTGGGC
7761 CCGAGATGCC ATGAATCTCT CAGGCAGGAG AGGAAGCAAA
7801 GGGCACATGA ATTACGAGGG CCCTGGAATG GCAAGGAAGT
7841 TCTCTGCACC TGGGCAACTG TGCATCTCCA TGACCTCGAA
7881 CCTGGGTGGC TCTGCCCCCA TCTCTGCAGC ATCAGCTACC
7921 TCTCTAGGTC ACTTCACCAA GTCTATGTGC CCCCCACAGC
7961 AGTATGGCTT TCCAGCTACC CCATTTGGCG CTCAATGGAG
8001 TGGGACGGGT GGCCCAGCAC CACAGCCACT TGGCCAGTTC
8041 CAACCTGTGG GAACTGCCTC CTTGCAGAAT TTCAACATCA
8081 GCAATTTGCA GAAATCCATC AGCAACCCCC CAGGCTCCAA
8121 CCTGCGGACC ACTTAGACCT AGAGACATTA ACTGAATAGA
8161 TCTGGGGGCA GGAGATGGAA TGCTGAGGGG GTGGGTGGGG
8201 GTGGGAAGTA GCCTATATAC TAACTACTAG TGCTGCATTT
```

-continued

```
8241 AACTGGTTAT TTCTTGCCAG AGGGGAATGT TTTTAATACT
8281 GCATTGAGCC CTCAGAATGG AGAGTCTCCC CCGCTCCAGT
8321 TATTGGAATG GGAGAGGAAG GAAAGAACAG CTTTTTTGTC
8361 AAGGGGCAGC TTCAGACCAT GCTTTCCTGT TTATCTATAC
8401 TCAGTAATGA GGATGAGGGC TAGGAAAGTC TTGTTCATAA
8441 GGAAGCTGGA GAACTCAATG TAAAATCAAA CCCATCTGTA
8481 ATTTCGAGTG GGTGGAGCTC TTGCTTTTGG TACATGCCCT
8521 GAATCCCTCA CTCCCTCAAG AATCCGAACC ACAGGACAAA
8561 AACCACCTAC TGGGCTCTCT CCTACCCTGC CCTCCTCCCT
8601 TTTTTTTACC CCTCTCTTTT TTATTTTTTC TTTGCTCTTT
8641 AGAACCCAGT GAAAAATACC AGGGTACTGG GGTGCAACTC
8681 TTTCTTATGA TAGGTCATTA GTGCTTTAAG CAAAAGATAT
8721 TAGCAGCTTT GACTGCAGCA TTAGCAATTA GGAAAAAAAA
8761 AAAATTAAGT TCCCTGCGGA CATGTAACTT TGCCATCAGT
8801 TTTGATGTGG AAACACTGTG ATATATAAAA TGTTGTTGGA
8841 CAACAGTAGT TTTAAGAGTA AAATATGAAA CGTTTAAAAA
8881 GTTCCAAAAA AAGCTAGCTC TGTCCTTTAC TTATTGAGAC
8921 ACTTTAACTT TTTCCTTTGT ATTTCCATTG TATTAGATAA
8961 ATAAATGTGA ATGTAAAATT GTATAAATTA CTGTACTTGA
9001 ATACTTCTGT TTCCCAGTGT TGCTTGCTGG ACATTTTAGT
9041 GCCTTGGACT TCTATTGCTT CTGCCATTAG CATCAACTTA
9081 CCAGACCCCA GATCAATAAA GGGCATGTGG AAGGAAATCG
9121 TAGGTCCATG TGACCCCAGC AGTCCAGCAG TGGTTATGCC
9161 AAAGGGAAAT TGAAAAAGTA TTTTTTTAAG TCATTCAACA
9201 ACTTTGTCTA GAGCAGGTGT AAGATGAGTA GGGTGGGAAG
9241 TTAGGTTGGC ATCAGTGGTT AAAAACAGAA AGTTCTGTTT
9281 CGGGAATAGT GAGGAGGGGG TGTTGTAACA AAATTGGACA
9321 ACTTAAAAGA ATGGTGTGTG CTGGGTGAAA GACAAAGACT
9361 AAAGAATGAG GAAACAAACG TGATGCCTGG CCAGTGACTG
9401 TCATATAAAC CTTTCTTATT TGAGCTAGGC TTGAACAGAC
9441 GTGACCTAGA AGAAACTGAA CATAAAGAGA AGGGGGTGGG
9481 GGGCTAGTTT TCAAGTTGGG GAACCTGATA GTGAAAAGTC
9521 ACAGATGGAG AAAATTGCTC TCAGAAAAAC TGTTTGGATT
9561 GCTTTCCTCT TGTTGCACAT GTACCATGCA TTTCTCAGCT
9601 TGGGGTACTA CATTTTGTGG AAAGTTAATC TATCTATCTT
9641 TCCACATCTG AATTAATCAT TCTAGGAAAG AATACTTATT
9681 CCTACTCATT TCCTTTATGA TGTCCAAATG GTTGCAGGAT
9721 CATAATCTAT TGTGCCACCT TTATTTCTAG AAGTACAACT
9761 AATATGTTCA CATTTTCAAA TAAATAATAC TCCCCGTAAG
9801 TAATAACTGC AACCAATCAG TGTTATTCAG TGCTATGCCT
```

-continued

```
9841 CCTTGTAATG GGTAGTTATT AATTATTTTC AGAGCTTTCC
9881 GGAAATACTG TCCTAACTGG CTATGTTTAG GATCTTTGTT
9921 ATCTCTGAAG ACAAAGAAAG AAGCTAGGAC TCTTAATTTT
9961 GGGGTGCTTC TTGACTCTTA GTTGGGAAAC TGAAAATATT
10001 TCCAACCTTT TACCCACGTC AATGGCATAT TCTGGGAATC
10041 ACCACCACCA CCACCACTAC CACAGAAAGA GGCTGGAGGC
10081 TCCTGTACCC TGTTCATTCC TTAAGGGCCC TGCTTCCCTT
10121 AGTAAGTAAG TAAGTTGGTC TACGGCCCTA AATATGCAAA
10161 TGAGAGCTGA AGGTTTTTAA AAGGTAGAAA GGAAAAGGGC
10201 AAGGGCTTCC ACCCCTGCTT TAAAATGATT TATTTATTCT
10241 CTGCTTGTAT TTCTTGTGGA GAGAGTAAGG ATAGAACCAA
10281 CAAGGGGCTG AGTAGCTGAG AAAGGGGCCA CCCAAGAGTG
10321 AAACATACTT TATACCAGAG GAGCAGTGGA GCCTCATGCA
10361 GCACATTATC ATTTGTTATT TGGGTTTAAT AATAATTTTG
10401 ACATCTTTTC ACTCATACAC AAAAAAAGTC AGAACTGGTG
10441 TTATTTACTG TTGATTTCAT CCTCCTGTGT ATGAAATAAC
10481 AAGCCTAGAG GAATGAACTA GTGCTACTGA ACTGTTTAAA
10521 TTATTTTTGT GTTAATAGTA CACTTTGAGT ATCTTTTTCC
10561 ACATTAAAAA CTTTCTGAAT TATAAATGTT TTCCTTACAT
10601 TATTTAACAA TGTACACTGT TAAAAATAAA AATAAAAATT
10641 CAAACTTTGG GGGTTTCTCA GCAGCCGTTA ATTGTACATT
10681 TTGCACTAAC TCTGGGTGTT GCGCTTCTTG TAAGATTGCG
10721 CTTTGTGCTT CAGTTTGTTA CCTTTGTAGA CTTATTTAAT
10761 GAAACCATTC AAATAAACCA AACTTGCTTT TGTTGA
```

Miscellaneous Section

Unless defined otherwise, all technical and scientific terms used herein have the same meaning as commonly understood by a person of ordinary skill in the art.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods, devices, and kits described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The term and/or in the context of this application means one or the other or both. For example, an aqueous solution of A and/or B means an aqueous solution of A alone, an aqueous solution of B alone and an aqueous solution of a combination of A and B.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The term "about" as used herein, when referring to a numerical value or range, allows for a degree of variability in the value or range, for example, within 10%, or within 5% of a stated value or of a stated limit of a range.

As used herein, "individual" (as in the subject of the treatment) or "patient" means humans.

The written description of this patent application includes all claims. All claims including all original claims are hereby incorporated by reference in their entirety into the written description portion of the specification and the right is reserved to physically incorporate into the written description or any other portion of the application any an all such claims. Thus, for example, under no circumstances may the patent be interpreted as allegedly not providing a written description for a claim on the assertion that the precise wording of the claim is not set forth in haec verba in written description portion of the patent.

The invention illustratively described herein suitably may be practiced in the absence of any element or elements, or limitation or limitations, which is not specifically disclosed herein as essential. Thus, for example, in each instance herein, in nonlimiting embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The term "may" in the context of this application means "is permitted to" or "is able to" and is a synonym for the term "can." The term "may" as used herein does not mean possibility or chance.

REFERENCES

1. Kearney P M, Whelton M, Reynolds K, Muntner P, Whelton P K, He J. Global burden of hypertension: Analysis of worldwide data. *Lancet* 2005; 365:217-223.
2. James P A, Oparil S, Carter B L, Cushman W C, Dennison-Himmelfarb C, Handler J, Lackland D T, LeFevre M L, Mackenzie T D, Ogedegbe O, Smith S C, Jr., Svetkey L P, Taler S J, Townsend R R, Wright J T, Jr., Narva A S, Ortiz E. 2014 evidence-based guideline for the management of high blood pressure in adults: Report from the panel members appointed to the eighth joint national committee (jnc 8). *JAMA* 2014; 311:507-520.
3. Doroszko A, Janus A, Szahidewicz-Krupska E, Mazur G, Derkacz A. Resistant hypertension. Advances in clinical and experimental medicine: official organ Wroclaw Medical University 2016; 25:173-183.
4. Smithwick R H, Thompson J E. Splanchnicectomy for essential hypertension; results in 1,266 cases. *J Am Med Assoc* 1953; 152:1501-1504.
5. Esler M D, Bohm M, Sievert H, Rump C L, Schmieder R E, Krum H, Mahfoud F, Schlaich M P. Catheter-based renal denervation for treatment of patients with treatment-resistant hypertension: 36 month results from the symplicity htn-2 randomized clinical trial. *Eur Heart J* 2014; 35:1752-1759.
6. Krum H, Schlaich M P, Sobotka P A, Bohm M, Mahfoud F, Rocha-Singh K, Katholi R, Esler M D. Percutaneous renal denervation in patients with treatment-resistant hypertension: Final 3-year report of the symplicity htn-1 study. *Lancet* 2014; 383:622-629.
7. Symplicity H T N I, Esler M D, Krum H, Sobotka P A, Schlaich M P, Schmieder R E, Bohm M. Renal sympathetic denervation in patients with treatment-resistant hypertension (the symplicity htn-2 trial): A randomised controlled trial. *Lancet* 2010; 376:1903-1909.
8. Bhatt D L, Kandzari D E, O'Neill W W, D'Agostino R, Flack J M, Katzen B T, Leon M B, Liu M, Mauri L, Negoita M, Cohen S A, Oparil S, Rocha-Singh K, Townsend R R, Bakris G L, Investigators S H-. A controlled trial of renal denervation for resistant hypertension. *N Engl J Med* 2014; 370:1393-1401.
9. Calhoun D A, Jones D, Textor S, Goff D C, Murphy T P, Toto R D, White A, Cushman W C, White W, Sica D, Ferdinand K, Giles T D, Falkner B, Carey R M. Resistant hypertension: Diagnosis, evaluation, and treatment: A scientific statement from the american heart association professional education committee of the council for high blood pressure research. *Circulation* 2008; 117: e510-526.
10. Schlaich M P. Renal sympathetic denervation: A viable option for treating resistant hypertension. *American journal of hypertension* 2017; 30:847-856.
11. Li Z Z, Jiang H, Chen D, Liu Q, Geng J, Guo J Q, Sun R H, Zhu G Q, Shan Q J. Renal sympathetic denervation improves cardiac dysfunction in rats with chronic pressure overload. *Physiological research* 2015; 64:653-662.
12. Snyder E M, Turner S T, Joyner M J, Eisenach J H, Johnson B D. The arg16gly polymorphism of the {beta}2- adrenergic receptor and the natriuretic response to rapid saline infusion in humans. *J Physiol* 2006; 574:947-954.
13. Vangjeli C, Clarke N, Quinn U, Dicker P, Tighe O, Ho C, O'Brien E, Stanton A V. Confirmation that the renin gene distal enhancer polymorphism ren-5312c/t is associated with increased blood pressure. *Circulation Cardiovascular genetics* 2010; 3:53-59.
14. Tsioufis C, Dimitriadis K, Thomopoulos C, Doumas M, Papademetriou V, Stefanadis C. Renal and cardiac effects of renal sympathetic denervation and carotid baroreceptor stimulation. *Current vascular pharmacology* 2014; 12:55-62.
15. Pinkham M I, Loftus M T, Amirapu S, Guild S J, Quill G, Woodward W R, Habecker B A, Barrett C J. Renal denervation in male rats with heart failure improves ventricular sympathetic nerve innervation and function. *Am J Physiol* Regul Integr Comp Physiol 2017; 312: R368-R379.
16. Watanabe H, Iwanaga Y, Miyaji Y, Yamamoto H, Miyazaki S. Renal denervation mitigates cardiac remodeling and renal damage in dahl rats: A comparison with beta-receptor blockade. *Hypertens Res* 2016; 39:217-226.
17. Clayton S C, Haack K K, Zucker I H. Renal denervation modulates angiotensin receptor expression in the renal cortex of rabbits with chronic heart failure. *Am J Physiol Renal Physiol* 2011; 300: F31-39.
18. Ding X, Xu X, Yan Y, Song X, Liu S, Wang G, Su D, Jing Q, Qin Y. Effects of renal sympathetic denervation and angiotensin-converting enzyme inhibitor on left ventricular hypertrophy. Comparison in spontaneously hypertensive rats. *Herz* 2015; 40:695-701.
19. Liu Q, Zhang Q, Wang K, Wang S, Lu D, Li Z, Geng J, Fang P, Wang Y, Shan Q. Renal denervation findings on cardiac and renal fibrosis in rats with isoproterenol induced cardiomyopathy. *Scientific reports* 2015; 5:18582.
20. Gupta A K. Racial differences in response to antihypertensive therapy: Does one size fits all? *International journal of preventive medicine* 2010; 1:217-219.
21. Jones E S, Spence J D, Mcintyre A D, Nondi J, Gogo K, Akintunde A, Hackam D G, Rayner B L. High frequency of variants of candidate genes in black africans with low renin-resistant hypertension. *American journal of hypertension* 2017; 30:478-483.
22. Ulgen M S, Ozturk O, Alan S, Kayrak M, Turan Y, Tekes S, Toprak N. The relationship between angiotensin-converting enzyme (insertion/deletion) gene polymorphism and left ventricular remodeling in acute myocardial infarction. *Coron Artery Dis* 2007; 18:153-157.
23. McNamara D M, Holubkov R, Postava L, Janosko K, MacGowan G A, Mathier M, Murali S, Feldman A M, London B. Pharmacogenetic interactions between angiotensin-converting enzyme inhibitor therapy and the angiotensin-converting enzyme deletion polymorphism in patients with congestive heart failure. *J Am Coll Cardiol* 2004; 44:2019-2026.
24. Pilati M, Cicoira M, Zanolla L, Nicoletti I, Muraglia S, Zardini P. The role of angiotensin-converting enzyme polymorphism in congestive heart failure. *Congest Heart Fail* 2004; 10:87-93; quiz 94-85.
25. Pilbrow A P, Palmer B R, Frampton C M, Yandle T G, Troughton R W, Campbell E, Skelton L, Lainchbury J G, Richards A M, Cameron V A. Angiotensinogen m235t and t174m gene polymorphisms in combination doubles the risk of mortality in heart failure. *Hypertension* 2007; 49:322-327.
26. Tang W, Devereux R B, Rao D C, Oberman A, Hopkins P N, Kitzman D W, Arnett D K. Associations between angiotensinogen gene variants and left ventricular mass and function in the hypergen study. *Am Heart J* 2002; 143:854-860.
27. Miller J A, Thai K, Scholey J W. Angiotensin ii type 1 receptor gene polymorphism predicts response to losartan and angiotensin ii. *Kidney Int* 1999; 56:2173-2180.
28. Baudin B. Angiotensin ii receptor polymorphisms in hypertension. Pharmacogenomic considerations. *Pharmacogenomics* 2002; 3:65-73.
29. Brodde O E. The functional importance of beta 1 and beta 2 adrenoceptors in the human heart. *Am J Cardiol* 1988; 62: 24C-29C.
30. Bristow M R, Hershberger R E, Port J D, Minobe W, Rasmussen R. Beta 1- and beta 2-adrenergic receptor-mediated adenylate cyclase stimulation in nonfailing and failing human ventricular myocardium. *Mol Pharmacol* 1989; 35:295-303.
31. Busjahn A, Li G-H, Faulhaber H-D, Rosenthal M, Becker A, Jeschke E, Schuster H, Timmermann B, Hoehe M R, Luft F C. {beta}-2 adrenergic receptor gene variations, blood pressure, and heart size in normal twins. *Hypertension* 2000; 35:555-560.
32. Snyder E M, Beck K C, Dietz N M, Eisenach J H, Joyner M J, Turner S T, Johnson B D. Arg16gly polymorphism of the {beta}2-adrenergic receptor is associated with differences in cardiovascular function at rest and during exercise in humans. *J Physiol* 2006; 571:121-130.
33. Drysdale C M, McGraw D W, Stack C B, Stephens J C, Judson R S, Nandabalan K, Arnold K, Ruano G, Liggett S B. Complex promoter and coding region beta 2-adrenergic receptor haplotypes alter receptor expression and predict in vivo responsiveness. *Proc Natl Acad Sci USA* 2000; 97:10483-10488.
34. Johnson J A, Turner S T. Hypertension pharmacogenomics: Current status and future directions. *Curr Opin Mol Ther* 2005; 7:218-225.
35. La Rosee K, Huntgeburth M, Rosenkranz S, Bohm M, Schnabel P. The arg389gly beta1-adrenoceptor gene polymorphism determines contractile response to catecholamines. *Pharmacogenetics* 2004; 14:711-716.
36. Liu J, Liu Z-Q, Tan Z-R, Chen X-P, Wang L-S, Zhou G, Zhou H-H. Gly389arg polymorphism of [beta]1-adrenergic receptor is associated with the cardiovascular response to metoprolol [ast]. *Clin Pharmacol Ther* 2003; 74:372-379.
37. Kurnik D, Li C, Sofowora G G, Friedman E A, Muszkat M, Xie H G, Harris P A, Williams S M, Nair U B, Wood A J, Stein C M. Beta-1-adrenoceptor genetic variants and ethnicity independently affect response to beta-blockade. *Pharmacogenetics and genomics* 2008; 18:895-902.
38. Snyder E M, Hulsebus M L, Turner S T, Joyner M J, Johnson B D. Genotype related differences in beta2 adrenergic receptor density and cardiac function. *Med Sci Sports Exerc* 2006; 38:882-886.
39. Snyder E M, Johnson B D, Joyner M J. Genetics of beta2-adrenergic receptors and the cardiopulmonary response to exercise. *Exerc Sport Sci Rev* 2008; 36:98-105.
40. Snyder E M, Joyner M J, Turner S T, Johnson B D. Blood pressure variation in healthy humans: A possible interaction with beta-2 adrenergic receptor genotype and renal epithelial sodium channels. *Med Hypotheses* 2005; 65:296-299.
41. Meisler M H, Barrow L L, Canessa C M, Rossier B C. Scnn1, an epithelial cell sodium channel gene in the conserved linkage group on mouse chromosome 6 and human chromosome 12. *Genomics* 1994; 24:185-186.

42. Jin H S, Hong K W, Lim J E, Hwang S Y, Lee S H, Shin C, Park H K, Oh B. Genetic variations in the sodium balance-regulating genes enac, nedd41, ndfip2 and usp2 influence blood pressure and hypertension. *Kidney Blood Press Res* 2010; 33:15-23.
43. Pratt J H. Central role for enac in development of hypertension. *J Am Soc Nephrol* 2005; 16:3154-3159.
44. Zhang L N, Ji L D, Fei L J, Yuan F, Zhang Y M, Xu J. Association between polymorphisms of alpha-adducin gene and essential hypertension in chinese population. *BioMed research international* 2013; 2013:451094.
45. Psaty B M, Smith N L, Heckbert S R, Vos H L, Lemaitre R N, Reiner A P, Siscovick D S, Bis J, Lumley T, Longstreth W T, Jr., Rosendaal F R. Diuretic therapy, the alpha-adducin gene variant, and the risk of myocardial infarction or stroke in persons with treated hypertension. *JAMA* 2002; 287:1680-1689.
46. Turner S T, Schwartz G L, Chapman A B, Boerwinkle E. Wnk1 kinase polymorphism and blood pressure response to a thiazide diuretic. *Hypertension* 2005; 46:758-765.
47. Kurnik, D., et al., Genetic variants in the alpha2C-adrenoceptor and G-protein contribute to ethnic differences in cardiovascular stress responses. Pharmacogenet Genomics, 2008. 18 (9): p. 743-50.
48. Kohli, U., et al., Genetic variation in the presynaptic norepinephrine transporter is associated with blood pressure responses to exercise in healthy humans. Pharmacogenet Genomics, 2011. 21 (4): p. 171-8.
49. Bristow, M. R., et al., An alpha2C-adrenergic receptor polymorphism alters the norepinephrine-lowering effects and therapeutic response of the beta-blocker bucindolol in chronic heart failure. Circ Heart Fail, 2010. 3 (1): p. 21-8.
50. Kurnik, D., et al., Genetic variations in the alpha (2A)-adrenoreceptor are associated with blood pressure response to the agonist dexmedetomidine. Circ Cardiovasc Genet, 2011. 4 (2): p. 179-87.
51. Ghimire, L. V., et al., Variation in the alpha (2A) adrenoceptor gene and the effect of dexmedetomidine on plasma insulin and glucose. Pharmacogenet Genomics, 2013. 23 (9): p. 479-86.

What is claimed is:

1. A method for renal denervation treatment of a human patient with cardiovascular hypertension where the patient has been classified as having Protocol 1i, 1ii, 2 or 3 comprising:

a) obtaining a nucleic acid sample from the patient comprising gene sequences of the ADRA2A, ADRA2C, ADRB1, ADRB2, renin, AGT, ACE, AGT1R, WNK1, ADD1, SLC12A3 and SCNN1A genes;

b) screening the nucleic acid sample to determine whether the sample contains one or more of the gene sequences of categories A, B, C, D and E to thereby obtain a genetic panel:

Category A:

1. An ADRA2A nucleic acid with a cytosine at the variable position rs2484516;
2. An ADRA2A nucleic acid with a thymine at the variable position rs553668;
3. An ADRA2C nucleic acid with a DELETION at the variable position rs13118711;

Category B:

1. An ADRB1 nucleic acid with a cytosine at the variable position of rs1801253;
2. An ADRB1 nucleic acid with an adenine at the variable position of rs1801252;
3. An ADRB2 nucleic acid with a guanine at the variable position of rs1042714;
4. An ADRB2 nucleic acid with a guanine at the variable position of rs1042713;

Category C:

1. A renin nucleic acid with a thymine at the variable position of rs12750834;
2. An AGT nucleic acid with a cytosine at the variable position of rs699;
3. An AGT nucleic acid with a thymine at position rs5051;
4. An AGT nucleic acid with a guanine at rs7079;

Category D:

1. An ACE nucleic acid with a deletion in rs1799752;
2. An AGT1R nucleic acid with a cytosine at the variable position of rs5186;

Category E:

1. A WNK1 nucleic acid with a cytosine at the variable position of rs1159744;
2. A WNK1 nucleic acid with a cytosine at the variable position of rs2107614;
3. A WNK1 nucleic acid with a cytosine at the variable position of rs2277869
4. An ADD1 nucleic acid with a thymine at the variable position of rs4961;
5. A SLC12A3 nucleic acid with a thymine at the variable nucleic acid position of rs1529927;
6. A SCNN1A nucleic acid with a thymine at variable nucleic acid position rs2228576;

c) classifying the patient according to the following protocols:

Protocol 1i) the genetic panel shows that the patient has all gene sequences of categories A, B, C, D and E;

Protocol 1ii) the genetic panel shows that the patient has all gene sequences of categories A, B, C and D but no gene sequence of category E;

Protocol 2) the genetic panel shows that the patient has all gene sequences of categories A, B and D, the gene sequences C1 and C2 of category C, and all gene sequences of category D;

Protocol 3) the genetic panel shows that the patient has all gene sequences of categories A, B and D; and d) conducting a treatment of at least a partial surgical denervation of the sympathetic nerves lining the nephritic arteries of one or both of the patient's kidneys to produce a treated patient when the patient is classified as having Protocol 1i, 1ii, 2 or 3.

2. The method according to claim 1 wherein the surgical denervation is conducted as one to eight treatments along one or both nephritic arteries at the arterial distal region relative to the kidney.

3. The method according to claim 1 wherein the surgical denervation is conducted as one to twelve treatments along one or both nephritic arteries at the arterial distal region relative to the kidney.

4. The method according to claim 1 wherein the surgical denervation is conducted as one to eight treatments along one or both of the nephritic arteries at the arterial proximal region relative to the kidney.

5. The method according to claim 1 wherein the surgical denervation is conducted as four to twelve treatments along one or both of the nephritic arteries at the arterial proximal region relative to the kidney.

6. The method according to claim 1, wherein the patient has been classified as having the genetic panel of Protocol 1i, 1ii or 2.

7. The method according to claim 1, wherein the patient has been classified as having the genetic panel of Protocol 1i or 1ii.

8. The method according to claim 1, wherein the patient has been classified as having the genetic panel of Protocol 1i.

9. The method according to claim 1 further comprising:

administering to the treated patient a β blocker drug, an Angiotensin II receptor blocker drug, or an ACE II inhibitor drug according to the following regimen:

i) if the treated patient's genetic panel falls into Category A, administer the β blocker drug;

ii) if the treated patient's genetic panel falls into Category B, administer the Angiotensin II receptor blocker drug;

iii) if the treated patient's genetic panel falls into Category C, administer the ACE inhibitor drug.

10. A method for treatment of a human patient with cardiovascular hypertension comprising:

Procedure 1, conducting a treatment of at least a partial surgical denervation of one to twelve treatments of the sympathetic nerves lining one or both nephritic arteries at the arterial distal region relative to the patient's kidney or kidneys when the patient has been determined to have all nucleic acid sequences of categories A, B, C, D and E;

Procedure 2, conducting a treatment of surgical denervation of one to eight treatments of the sympathetic nerves lining one or both nephritic arteries at the arterial proximal region relative to the patient's kidney or kidneys when the patient has been determined to have all nucleic acid sequences of categories A, B, C, D but not any sequences of category E;

Procedure 3, conducting a treatment of surgical denervation of six to twelve treatments of the sympathetic nerves lining one or both nephritic arteries at the arterial proximal region relative to the patient's kidney or kidneys when the patient has been determined to have all nucleic acid sequences of categories A, B, D and sequences C1 and C2 of category C but not any of category C3 or C4 of category C or category E;

or the patient has been determined to have all nucleic acid sequences of categories A, B and D but not any of category C or E;

wherein the nucleic acid sequences of categories A, B, C, D and E are:

Category A:

1. An ADRA2A nucleic acid with a cytosine at the variable position rs2484516;
2. An ADRA2A nucleic acid with a thymine at the variable position rs553668;
3. An ADRA2C nucleic acid with a DELETION at the variable position rs13118711;

Category B:

1. An ADRB1 nucleic acid with a cytosine at the variable position of rs1801253;
2. An ADRB1 nucleic acid with an adenine at the variable position of rs1801252;
3. An ADRB2 nucleic acid with a guanine at the variable position of rs1042714;
4. An ADRB2 nucleic acid with a guanine at the variable position of rs1042713;

Category C:

1. A renin nucleic acid with a thymine at the variable position of rs12750834;
2. An AGT nucleic acid with a cytosine at the variable position of rs699;
3. An AGT nucleic acid with a thymine at position rs5051;
4. An AGT nucleic acid with a guanine at rs7079;

Category D:

1. An ACE nucleic acid with a deletion in rs1799752;
2. An AGT1R nucleic acid with a cytosine at the variable position of rs5186;

Category E:

1. A WNK1 nucleic acid with a cytosine at the variable position of rs1159744;
2. A WNK1 nucleic acid with a cytosine at the variable position of rs2107614;
3. A WNK1 nucleic acid with a cytosine at the variable position of rs2277869
4. An ADD1 nucleic acid with a thymine at the variable position of rs4961;
5. A SLC12A3 nucleic acid with a thymine at the variable nucleic acid position of rs1529927; and
6. A SCNN1A nucleic acid with a thymine at variable nucleic acid position rs2228576.

11. The method according to claim 10 comprising Procedure 1 and the surgical denervation is conducted as one to eight treatments along one or both nephritic arteries at the arterial distal region relative to the kidney.

12. The method according to claim 10 comprising Procedure 1 and the surgical denervation is conducted as four to twelve treatments of the sympathetic nerves lining one or both nephritic arteries at the arterial distal region relative to the kidney.

13. The method according to claim 10 comprising Procedure 2 and the surgical denervation is conducted as one to eight treatments of the sympathetic nerves lining one or both of the nephritic arteries at the arterial proximal region relative to the kidney.

14. The method according to claim 10 comprising Procedure 3 and the surgical denervation is conducted as four to twelve treatments of the sympathetic nerves lining one or both of the nephritic arteries at the arterial proximal region relative to the kidney.

15. The method according to claim 1 wherein the patient has hypertension and the patient's hypertension is not resistant to treatment with anti-hypertensive pharmaceuticals.

16. The method according to claim 1 wherein the patient has hypertension and the patient's hypertension is resistant to treatment with anti-hypertensive pharmaceuticals.

17. The method according to claim 2, wherein the patient has been classified as having the genetic panel of Protocol 1i, 1ii or 2.

18. The method according to claim 2, wherein the patient has been classified as having the genetic panel of Protocol 1i or 1ii.

19. The method according to claim 2, wherein the patient has been classified as having the genetic panel of Protocol 1i.

20. The method according to claim 2 further comprising: administering to the treated patient a β blocker drug, an Angiotensin II receptor blocker drug, or an ACE II inhibitor drug according to the following regimen:

i) if the treated patient's genetic panel falls into Category A, administer the β blocker drug;

ii) if the treated patient's genetic panel falls into Category B, administer the Angiotensin II receptor blocker drug;

iii) if the treated patient's genetic panel falls into Category C, administer the ACE inhibitor drug.

21. The method according to claim 3, wherein the patient has been classified as having the genetic panel of Protocol 1i, 1ii or 2.

22. The method according to claim 3, wherein the patient has been classified as having the genetic panel of Protocol 1i or 1ii.

23. The method according to claim 3, wherein the patient has been classified as having the genetic panel of Protocol 1i.

24. The method according to claim 3, further comprising: administering to the treated patient a β blocker drug, an Angiotensin II receptor blocker drug, or an ACE II inhibitor drug according to the following regimen:

i) if the treated patient's genetic panel falls into Category A, administer the β blocker drug;

ii) if the treated patient's genetic panel falls into Category B, administer the Angiotensin II receptor blocker drug;

iii) if the treated patient's genetic panel falls into Category C, administer the ACE inhibitor drug.

25. The method according to claim 4, wherein the patient has been classified as having the genetic panel of Protocol 1i, 1ii or 2.

26. The method according to claim 4, wherein the patient has been classified as having the genetic panel of Protocol 1i or 1ii.

27. The method according to claim 4, wherein the patient has been classified as having the genetic panel of Protocol 1i.

28. The method according to claim 4 further comprising: administering to the treated patient a β blocker drug, an Angiotensin II receptor blocker drug, or an ACE II inhibitor drug according to the following regimen:

i) if the treated patient's genetic panel falls into Category A, administer the β blocker drug;

ii) if the treated patient's genetic panel falls into Category B, administer the Angiotensin II receptor blocker drug;

iii) if the treated patient's genetic panel falls into Category C, administer the ACE inhibitor drug.

29. The method according to claim 5, wherein the patient has been classified as having the genetic panel of Protocol 1i, 1ii or 2.

30. The method according to claim 5, wherein the patient has been classified as having the genetic panel of Protocol 1i or 1ii.

31. The method according to claim 5, wherein the patient has been classified as having the genetic panel of Protocol 1i.

32. The method according to claim 5 further comprising: administering to the treated patient a β blocker drug, an Angiotensin II receptor blocker drug, or an ACE II inhibitor drug according to the following regimen:

i) if the treated patient's genetic panel falls into Category A, administer the β blocker drug;

ii) if the treated patient's genetic panel falls into Category B, administer the Angiotensin II receptor blocker drug;

iii) if the treated patient's genetic panel falls into Category C, administer the ACE inhibitor drug.

* * * * *

SEQUENCE LISTING

```
<160> NUMBER OF SEQ ID NOS: 156

<210> SEQ ID NO 1
<211> LENGTH: 2862
<212> TYPE: DNA
<213> ORGANISM: Homo sapiens

<400> SEQUENCE: 1

gcaccacgcc gcccgggctt ctggggtgtt ccccaaccac ggcccagccc tgccacaccc      60
cccgcccccg gcctccgcag ctcggcatgg gcgcgggggt gctcgtcctg ggcgcctccg     120
agcccggtaa cctgtcgtcg gccgcaccgc tccccgacgg cgcggccacc gcggcgcggc     180
tgctggtgcc cgcgtcgccg cccgcctcgt tgctgcctcc cgccagcgaa agccccgagc     240
cgctgtctca gcagtggaca gcgggcatgg gtctgctgat ggcgctcatc gtgctgctca     300
tcgtggcggg caatgtgctg gtgatcgtgg ccatcgccaa gacgccgcgg ctgcagacgc     360
tcaccaacct cttcatcatg tccctggcca gcgccgacct ggtcatgggg ctgctggtgg     420
tgccgttcgg ggccaccatc gtggtgtggg gccgctggga gtacggctcc ttcttctgcg     480
agctgtggac ctcagtggac gtgctgtgcg tgacggccag catcgagacc ctgtgtgtca     540
ttgccctgga ccgctacctc gccatcacct cgcccttccg ctaccagagc ctgctgacgc     600
gcgcgcgggc gcggggcctc gtgtgcaccg tgtgggccat ctcggccctg gtgtccttcc     660
tgcccatcct catgcactgg tggcgggcgg agagcgacga ggcgcgccgc tgctacaacg     720
accccaagtg ctgcgacttc gtcaccaacc gggcctacgc catcgcctcg tccgtagtct     780
ccttctacgt gcccctgtgc atcatggcct tcgtgtacct gcgggtgttc cgcgaggccc     840
agaagcaggt gaagaagatc gacagctgcg agcgccgttt cctcggcggc ccagcgcggc     900
cgccctcgcc ctcgccctcg cccgtccccg cgcccgcgcc gccgcccgga cccccgcgcc     960
ccgccgccgc cgccgccacc gccccgctgg ccaacgggcg tgcgggtaag cggcggccct    1020
cgcgcctcgt ggccctgcgc gagcagaagg cgctcaagac gctgggcatc atcatgggcg    1080
tcttcacgct ctgctggctg cccttcttcc tggccaacgt ggtgaaggcc ttccaccgcg    1140
agctggtgcc cgaccgcctc ttcgtcttct tcaactggct gggctacgcc aactcggcct    1200
tcaaccccat catctactgc cgcagccccg acttccgcaa ggccttccag ggactgctct    1260
```

-continued

```
gctgcgcgcg cagggctgcc cgccggcgcc acgcgaccca cggagaccgg ccgcgcgcct   1320

cgggctgtct ggcccggccc ggaccccccgc catcgcccgg ggccgcctcg gacgacgacg   1380

acgacgatgt cgtcggggcc acgccgcccg cgcgcctgct ggagccctgg gccggctgca   1440

acggcggggc ggcggcggac agcgactcga gcctggacga gccgtgccgc cccggcttcg   1500

cctcggaatc caaggtgtag ggcccggcgc ggggcgcgga ctccgggcac ggcttcccag   1560

gggaacgagg agatctgtgt ttacttaaga ccgatagcag gtgaactcga agcccacaat   1620

cctcgtctga atcatccgag gcaaagagaa aagccacgga ccgttgcaca aaaaggaaag   1680

tttgggaagg gatgggagag tggcttgctg atgttccttg ttgttttttt tttcttttct   1740

tttctttctt cttctttttt tttttttttt ttttttctgt ttgtggtccg gccttctttt   1800

gtgtgtgcgt gtgatgcatc tttagatttt tttcccccac caggtggttt ttgacactct   1860

ctgagaggac cggagtggaa gatgggtggg ttaggggaag ggagaagcat taggagggga   1920

ttaaaatcga tcatcgtggc tcccatccct ttcccgggaa caggaacaca ctaccagcca   1980

gagagaggag aatgacagtt tgtcaagaca tatttccttt tgctttccag agaaatttca   2040

ttttaatttc taagtaatga tttctgctgt tatgaaagca aagagaaagg atggaggcaa   2100

aataaaaaaa aatcacgttt caagaaatgt taagctcttc ttggaacaag ccccaccttg   2160

ctttccttgt gtagggcaaa cccgctgtcc cccgcgcgcc tgggtggtca ggctgaggga   2220

tttctacctc acactgtgca tttgcacagc agatagaaag acttgtttat attaaacagc   2280

ttatttatgt atcaatatta gttggaagga ccaggcgcag agcctctctc tgtgacatgt   2340

gactctgtca attgaagaca ggacattaaa agagagcgag agagagaaac agttcagatt   2400

actgcacatg tggataaaaa caaaaacaaa aaaaaggagt ggttcaaaat gccatttttg   2460

cacagtgtta ggaattacaa aatccacaga agatgttact tgcacaaaaa gaaattaaat   2520

attttttaaa gggagagggg ctgggcagat cttaaataaa attcaaactc tacttctgtt   2580

gtctagtatg ttattgagct aatgattcat tgggaaaata cctttttata ctcctttatc   2640

atggtactgt aactgtatcc atattataaa tataattatc ttaaggattt tttatttttt   2700

tttatgtcca agtgcccacg tgaatttgct ggtgaaagtt agcacttgtg tgtaaattct   2760

acttcctctt gtgtgtttta ccaagtattt atactctggt gcaactaact actgtgtgag   2820

gaattggtcc atgtgcaata aataccaatg aagcacaatc aa                     2862
```

<210> SEQ ID NO 2
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n =  A or G

<400> SEQUENCE: 2

```
ctcgttgctg cctcccgcca gcgaangccc cgagccgctg tctcagcagt g              51
```

<210> SEQ ID NO 3
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or G

<400> SEQUENCE: 3
ccccgacttc cgcaaggcct tccagngact gctctgctgc gcgcgcaggg c 51

<210> SEQ ID NO 4

<400> SEQUENCE: 4

000

<210> SEQ ID NO 5
<211> LENGTH: 2058
<212> TYPE: DNA
<213> ORGANISM: Homo sapiens

<400> SEQUENCE: 5
gcacataacg ggcagaacgc actgcgaagc ggcttcttca gagcacgggc tggaactggc 60
aggcaccgcg agcccctagc acccgacaag ctgagtgtgc aggacgagtc cccaccacac 120
ccacaccaca gccgctgaat gaggcttcca ggcgtccgct cgcggcccgc agagccccgc 180
cgtgggtccg cccgctgagg cgcccccagc cagtgcgctc acctgccaga ctgcgcgcca 240
tggggcaacc cgggaacggc agcgccttct tgctggcacc caatagaagc catgcgccgg 300
accacgacgt cacgcagcaa agggacgagg tgtgggtggt gggcatgggc atcgtcatgt 360
ctctcatcgt cctggccatc gtgtttggca atgtgctggt catcacagcc attgccaagt 420
tcgagcgtct gcagacggtc accaactact tcatcacttc actggcctgt gctgatctgg 480
tcatgggcct ggcagtggtg ccctttgggg ccgcccatat tcttatgaaa atgtggactt 540
ttggcaactt ctggtgcgag ttttggactt ccattgatgt gctgtgcgtc acggccagca 600
ttgagaccct gtgcgtgatc gcagtggatc gctactttgc cattacttca cctttcaagt 660
accagagcct gctgaccaag aataaggccc gggtgatcat tctgatggtg tggattgtgt 720
caggccttac ctccttcttg cccattcaga tgcactggta ccgggccacc caccaggaag 780
ccatcaactg ctatgccaat gagacctgct gtgacttctt cacgaaccaa gcctatgcca 840
ttgcctcttc catcgtgtcc ttctacgttc ccctggtgat catggtcttc gtctactcca 900
gggtctttca ggaggccaaa aggcagctcc agaagattga caaatctgag ggccgcttcc 960
atgtccagaa ccttagccag gtggagcagg atgggcggac ggggcatgga ctccgcagat 1020
cttccaagtt ctgcttgaag gagcacaaag ccctcaagac gttaggcatc atcatgggca 1080
ctttcaccct ctgctggctg cccttcttca tcgttaacat tgtgcatgtg atccaggata 1140
acctcatccg taaggaagtt tacatcctcc taaattggat aggctatgtc aattctggtt 1200
tcaatcccct tatctactgc cggagcccag atttcaggat tgccttccag gagcttctgt 1260
gcctgcgcag gtcttctttg aaggcctatg ggaatggcta ctccagcaac ggcaacacag 1320
gggagcagag tggatatcac gtggaacagg agaaagaaaa taaactgctg tgtgaagacc 1380
tcccaggcac ggaagacttt gtgggccatc aaggtactgt gcctagcgat aacattgatt 1440
cacaagggag gaattgtagt acaaatgact cactgctgta aagcagtttt tctactttta 1500
aagacccccc cccccaacag aacactaaac agactattta acttgagggt aataaactta 1560
gaataaaatt gtaaaattgt atagagatat gcagaaggaa gggcatcctt ctgccttttt 1620 tatttttttta agctgtaaaa agagagaaaa cttatttgag tgattatttg ttatttgtac 1680
agttcagttc ctctttgcat ggaatttgta agtttatgtc taaagagctt tagtcctaga 1740
ggacctgagt ctgctatatt ttcatgactt ttccatgtat ctacctcact attcaagtat 1800
taggggtaat atattgctgc tggtaatttg tatctgaagg agattttcct tcctacaccc 1860
ttggacttga ggattttgag tatctcggac ctttcagctg tgaacatgga ctcttccccc 1920
actcctctta tttgctcaca cggggtattt taggcaggga tttgaggagc agcttcagtt 1980
gttttcccga gcaaagtcta aagtttacag taaataaatt gtttgaccat gccttcattg 2040
caaaaaaaaa aaaaaaaa 2058

<210> SEQ ID NO 6
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = A or G

<400> SEQUENCE: 6
cagcgccttc ttgctggcac ccaatngaag ccatgcgccg gaccacgacg t 51

<210> SEQ ID NO 7
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or G

<400> SEQUENCE: 7
tgcgccggac cacgacgtca cgcagnaaag ggacgaggtg tgggtggtgg g 51

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13
<211> LENGTH: 2587
<212> TYPE: DNA
<213> ORGANISM: Homo sapiens

<400> SEQUENCE: 13

-continued

```
atcccatgag cgggcagcag ggtcagaagt ggcccccgtg ttgcctaagc aagactctcc     60
cctgccctct gccctctgca cctccggcct gcatgtccct gtggcctctt gggggtacat    120
ctcccggggc tgggtcagaa ggcctgggtg gttggcctca ggctgtcaca cacctaggga    180
gatgctcccg tttctgggaa ccttggcccc gactcctgca aacttcggta aatgtgtaac    240
tcgaccctgc accggctcac tctgttcagc agtgaaactc tgcatcgatc actaagactt    300
cctggaagag gtcccagcgt gagtgtcgct tctggcatct gtccttctgg ccagcctgtg    360
gtctggccaa gtgatgtaac cctcctctcc agcctgtgca caggcagcct gggaacagct    420
ccatccccac ccctcagcta taaatagggc atcgtgaccc ggccggggga agaagctgcc    480
gttgttctgg gtactacagc agaagggtat gcggaagcga gcaccccagt ctgagatggc    540
tcctgccggt gtgagcctga gggccaccat cctctgcctc ctggcctggg ctggcctggc    600
tgcaggtgac cgggtgtaca tacacccctt ccacctcgtc atccacaatg agagtacctg    660
tgagcagctg gcaaaggcca atgccgggaa gcccaaagac ccccaccttca tacctgctcc    720
aattcaggcc aagacatccc ctgtggatga aaaggcccta caggaccagc tggtgctagt    780
cgctgcaaaa cttgacaccg aagacaagtt gagggccgca atggtcggga tgctggccaa    840
cttcttgggc ttccgtatat atggcatgca cagtgagcta tggggcgtgg tccatggggc    900
caccgtcctc tccccaacgg ctgtctttgg caccctggcc tctctctatc tgggagcctt    960
ggaccacaca gctgacaggc tacaggcaat cctgggtgtt ccttggaagg acaagaactg   1020
cacctcccgg ctggatgcgc acaaggtcct gtctgccctg caggctgtac agggcctgct   1080
agtggcccag ggcagggctg atagccaggc ccagctgctg ctgtccacgg tggtgggcgt   1140
gttcacagcc ccaggcctgc acctgaagca gccgtttgtg cagggcctgg ctctctatac   1200
ccctgtggtc ctcccacgct ctctggactt cacagaactg gatgttgctg ctgagaagat   1260
tgacaggttc atgcaggctg tgacaggatg gaagactggc tgctccctga tgggagccag   1320
tgtggacagc accctggctt tcaacaccta cgtccacttc caagggaaga tgaagggctt   1380
ctccctgctg gccgagcccc aggagttctg ggtggacaac agcacctcag tgtctgttcc   1440
catgctctct ggcatgggca ccttccagca ctggagtgac atccaggaca acttctcggt   1500
gactcaagtg cccttcactg agagcgcctg cctgctgctg atccagcctc actatgcctc   1560
tgacctggac aaggtggagg gtctcacttt ccagcaaaac tccctcaact ggatgaagaa   1620
actatctccc cggaccatcc acctgaccat gccccaactg gtgctgcaag gatcttatga   1680
cctgcaggac ctgctcgccc aggctgagct gcccgccatt ctgcacaccg agctgaacct   1740
gcaaaaattg agcaatgacc gcatcagggt gggggaggtg ctgaacagca ttttttttga   1800
gcttgaagcg gatgagagag agcccacaga gtctacccaa cagcttaaca agcctgaggt   1860
cttggaggtg accctgaacc gcccattcct gtttgctgtg tatgatcaaa gcgccactgc   1920
cctgcacttc ctgggccgcg tggccaaccc gctgagcaca gcatgaggcc agggccccag   1980
aacacagtgc ctggcaaggc ctctgcccct ggcctttgag gcaaaggcca gcagcagata   2040
acaaccccgg acaaatcagc gatgtgtcac ccccagtctc ccaccttttc ttctaatgag   2100
tcgactttga gctggaaagc agccgtttct ccttggtcta agtgtgctgc atggagtgag   2160
cagtagaagc ctgcagcggc acaaatgcac ctcccagttt gctgggttta ttttagagaa   2220
tgggggtggg gaggcaagaa ccagtgttta gcgcgggact actgttccaa aaagaattcc   2280
aaccgaccag cttgtttgtg aaacaaaaaa gtgttccctt ttcaagttga gaacaaaaat   2340
```

-continued tgggttttaa aattaaagta tacatttttg cattgccttc ggtttgtatt tagtgtcttg 2400
aatgtaagaa catgacctcc gtgtagtgtc tgtaatacct tagttttttc cacagatgct 2460
tgtgattttt gaacaatacg tgaaagatgc aagcacctga atttctgttt gaatgcggaa 2520
ccatagctgg ttatttctcc cttgtgttag taataaacgt cttgccacaa taagcctcca 2580
aaaaaaa 2587

<210> SEQ ID NO 14
<211> LENGTH: 51
<212> TYPE: DNA
<213> ORGANISM: Homo sapiens
<220> FEATURE:
<221> NAME/KEY: misc_feature
<222> LOCATION: (0)...(0)
<223> OTHER INFORMATION: n= C or T

<400> SEQUENCE: 14
ggatggaaga ctggctgctc cctganggga gccagtgtgg acagcaccct g 51

<210> SEQ ID NO 15

<400> SEQUENCE: 15

000

<210> SEQ ID NO 16

<400> SEQUENCE: 16

000

<210> SEQ ID NO 17
<211> LENGTH: 720
<212> TYPE: DNA
<213> ORGANISM: Homo sapiens

<400> SEQUENCE: 17
attcaactag gcatcatacg tgactgtaga attgcagata ttgtggacac ggccatgcct 60
atcaccattt gtatagctta ttttaacaat tgcctgaatc ctctttttta tggctttctg 120
gggaaaaaat ttaaaagata ttttctccag cttctaaaat atattccccc aaaagccaaa 180
tcccactcaa acctttcaac aaaaaatgagc acgctttcct accgcccctc agataatgta 240
agctcatcca ccaagaagcc tgcaccatgt tttgaggttg agtgacatgt tcgaaacctg 300
tccataaagt aattttgtga aagaaggagc aagagaacat tcctctgcag cacttcacta 360
ccaaatgagc attagctact tttcagaatt gaaggagaaa atgcattatg tggactgaac 420
cgacttttct aaagctctga acaaaagctt ttctttcctt ttgcaacaag acaaagcaaa 480
gccacatttt gcattagaca gatgacggct gctcgaagaa caatgtcaga aactcgatga 540
atgtgttgat ttgagaaatt ttactgacag aaatgcaatc tccctagcct gcttttgtcc 600
tgttattttt tatttccaca taaaggtatt tagaatatat taaatcgtta gaggagcaac 660
aggagatgag agttccagat tgttctgtcc agtttccaaa gggcagtaaa gttttcgtgc 720

<210> SEQ ID NO 18
<211> LENGTH: 2185
<212> TYPE: DNA
<213> ORGANISM: Homo sapiens

<400> SEQUENCE: 18
ggcagcagcg agtgacagga cgtctggacc ggcgcgccgc tagcagctct gccgggccgc 60

```
ggcggtgatc gatgggagcg gctggagcgg acccagcgag tgagggcgca cagccggacg    120
ccgaggcggc gggcgggaga ccgcaccgcg acgccggccc tcggcggacg agtcgagcgc    180
ccgggcgcgg gtgtatttga tatagtgttt gcaacaaatt cgacccaggt gatcaaaatg    240
attctcaact cttctactga agatggtatt aaaagaatcc aagatgattg tcccaaagct    300
ggaaggcata attacatatt tgtcatgatt cctactttat acagtatcat ctttgtggtg    360
ggaatatttg gaaacagctt ggtggtgata gtcatttact tttatatgaa gctgaagact    420
gtggccagtg tttttctttt gaatttagca ctggctgact tatgcttttt actgactttg    480
ccactatggg ctgtctacac agctatggaa taccgctggc cctttggcaa ttacctatgt    540
aagattgctt cagccagcgt cagtttcaac ctgtacgcta gtgtgtttct actcacgtgt    600
ctcagcattg atcgatacct ggctattgtt cacccaatga agtcccgcct tcgacgcaca    660
atgcttgtag ccaaagtcac ctgcatcatc atttggctgc tggcaggctt ggccagtttg    720
ccagctataa tccatcgaaa tgtatttttc attgagaaca ccaatattac agtttgtgct    780
ttccattatg agtcccaaaa ttcaaccctc ccgatagggc tgggcctgac caaaaatata    840
ctgggtttcc tgtttccttt tctgatcatt cttacaagtt atactcttat ttggaaggcc    900
ctaaagaagg cttatgaaat tcagaagaac aaaccaagaa atgatgatat ttttaagata    960
attatggcaa ttgtgctttt ctttttcttt tcctggattc cccaccaaat attcactttt   1020
ctggatgtat tgattcaact aggcatcata cgtgactgta gaattgcaga tattgtggac   1080
acggccatgc ctatcaccat ttgtatagct tattttaaca attgcctgaa tcctcttttt   1140
tatggctttc tggggaaaaa atttaaaaga tattttctcc agcttctaaa atatattccc   1200
ccaaaagcca aatcccactc aaacctttca acaaaaatga gcacgctttc ctaccgcccc   1260
tcagataatg taagctcatc caccaagaag cctgcaccat gttttgaggt tgagtgacat   1320
gttcgaaacc tgtccataaa gtaattttgt gaaagaagga gcaagagaac attcctctgc   1380
agcacttcac taccaaatga gcattagcta cttttcagaa ttgaaggaga aaatgcatta   1440
tgtggactga accgactttt ctaaagctct gaacaaaagc ttttctttcc ttttgcaaca   1500
agacaaagca aagccacatt ttgcattaga cagatgacgg ctgctcgaag aacaatgtca   1560
gaaactcgat gaatgtgttg atttgagaaa ttttactgac agaaatgcaa tctccctagc   1620
ctgcttttgt cctgttattt tttatttcca cataaaggta tttagaatat attaactcgt   1680
tagaggagca acaggagatg agagttccag attgttctgt ccagtttcca aagggcagta   1740
aagttttcgt gcctgttttc agctattagc aactgtgcct acacttgcac ctggtctgca   1800
cattttgtac aaagatatgc ttaagcagta gtcgtcaagt tgcagatctt tgttgtgaaa   1860
ttcaacctgt gtcttatagg tttacactgc caaaacaatg cccgtaagat ggcttatttg   1920
tataatggtg ttacctaaag tcacatataa aagttaaact acttgtaaag gtgctgcact   1980
ggtcccaagt agtagtgtct tcctagtata ttagtttgat ttaatatctg agaagtgtat   2040
atagtttgtg gtaaaaagat tatatatcat aaagtatgcc ttcctgttta aaaaaagtat   2100
atattctaca catatatgta tatgtatatc tatatctcta aactgctgtt aattgattaa   2160
aatctggcaa agttatattt acccc                                         2185
```

<210> SEQ ID NO 19
<211> LENGTH: 51
<212> TYPE: DNA
<213> ORGANISM: Homo sapiens
<220> FEATURE:

<221> NAME/KEY: misc_feature
<222> LOCATION: 26
<223> OTHER INFORMATION: n = A or G

<400> SEQUENCE: 19
agaacaccaa agcaggctta atctgngggc acttacagag actgctttaa a 51

<210> SEQ ID NO 20
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or T

<400> SEQUENCE: 20
tttaaagcag tctctgtaag tgcccncaga ttaagcctgc tttggtgttc t 51

<210> SEQ ID NO 21
<211> LENGTH: 3497
<212> TYPE: DNA
<213> ORGANISM: Homo sapiens

<400> SEQUENCE: 21
aaacagaagg cagatagaga gggagtgaga ggcaggagct gagacacaga tcctggagga 60
agaagaccaa aggaaggggg cagagacaga aagggaggtg ctaggacaaa actcgaaagg 120
tggccctatc agggaagcag aggagaggcc gttctaggga agcccagctc cggcactttt 180
ggccccaact cccgcaggtc tgctggctcc aggaaaggtg gaggagggag ggaggagtgg 240
gagaatgtgg gcgcagggtg ggacatgggc atggccaggg gcagcctcac tcgggttcca 300
ggggtgatgg gagagggcac tcagggccca gagctcagcc ttgaccctga cccttgctct 360
ccccaatcca ctccggggct catgaagggg aacaagctgg aggagcagga ccctagacct 420
ctgcagccca taccaggtct catggagggg aacaagctgg aggagcagga ctctagccct 480
ccacagtcca ctccagggct catgaagggg aacaagcgtg aggagcaggg gctgggcccc 540
gaacctgcgg cgccccagca gcccacggcg gaggaggagg ccctgatcga gttccaccgc 600
tcctaccgag agctcttcga gttcttctgc aacaacacca ccatccacgg cgccatccgc 660
ctggtgtgct cccagcacaa ccgcatgaag acggccttct gggcagtgct gtggctctgc 720
acctttggca tgatgtactg gcaattcggc ctgcttttcg gagagtactt cagctacccc 780
gtcagcctca acatcaacct caactcggac aagctcgtct tccccgcagt gaccatctgc 840
accctcaatc cctacaggta cccggaaatt aaagaggagc tggaggagct ggaccgcatc 900
acagagcaga cgctctttga cctgtacaaa tacagctcct tcaccactct cgtggccggc 960
tcccgcagcc gtcgcgacct gcgggggact ctgccgcacc ccttgcagcg cctgagggtc 1020
ccgcccccgc ctcacggggc ccgtcgagcc cgtagcgtgg cctccagctt gcgggacaac 1080
aacccccagg tggactggaa ggactggaag atcggcttcc agctgtgcaa ccagaacaaa 1140
tcggactgct tctaccagac atactcatca ggggtggatg cggtgaggga gtggtaccgc 1200
ttccactaca tcaacatcct gtcgaggctg ccagagactc tgccatccct ggaggaggac 1260
acgctgggca acttcatctt cgcctgccgc ttcaaccagg tctcctgcaa ccaggcgaat 1320
tactctcact tccaccaccc gatgtatgga aactgctata ctttcaatga caagaacaac 1380
tccaacctct ggatgtcttc catgcctgga atcaacaacg gtctgtccct gatgctgcgc 1440
gcagagcaga atgacttcat tcccctgctg tccacagtga ctggggcccg ggtaatggtg 1500

```
cacgggcagg atgaacctgc ctttatggat gatggtggct ttaacttgcg gcctggcgtg    1560
gagacctcca tcagcatgag gaaggaaacc ctggacagac ttgggggcga ttatggcgac    1620
tgcaccaaga atggcagtga tgttcctgtt gagaaccttt acccttcaaa gtacacacag    1680
caggtgtgta ttcactcctg cttccaggag agcatgatca aggagtgtgg ctgtgcctac    1740
atcttctatc cgcggcccca gaacgtggag tactgtgact acagaaagca cagttcctgg    1800
gggtactgct actataagct ccaggttgac ttctcctcag accacctggg ctgtttcacc    1860
aagtgccgga agccatgcag cgtgaccagc taccagctct ctgctggtta ctcacgatgg    1920
ccctcggtga catcccagga atgggtcttc cagatgctat cgcgacagaa caattacacc    1980
gtcaacaaca agagaaatgg agtggccaaa gtcaacatct tcttcaagga gctgaactac    2040
aaaaccaatt ctgagtctcc ctctgtcacg atggtcaccc tcctgtccaa cctgggcagc    2100
cagtggagcc tgtggttcgg ctcctcggtg ttgtctgtgg tggagatggc tgagctcgtc    2160
tttgacctgc tggtcatcat gttcctcatg ctgctccgaa ggttccgaag ccgatactgg    2220
tctccaggcc gagggggcag gggtgctcag gaggtagcct ccaccctggc atcctcccct    2280
ccttcccact tctgccccca ccccatgtct ctgtccttgt cccagccagg ccctgctccc    2340
tctccagcct tgacagcccc tccccctgcc tatgccaccc tgggcccccg cccatctcca    2400
gggggctctg caggggccag ttcctccacc tgtcctctgg gggggccctg agagggaagg    2460
agaggtttct cacaccaagg cagatgctcc tctggtggga gggtgctggc cctggcaaga    2520
ttgaaggatg tgcagggctt cctctcagag ccgcccaaac tgccgttgat gtgtggaggg    2580
gaagcaagat gggtaagggc tcaggaagtt gctccaagaa cagtagctga tgaagctgcc    2640
cagaagtgcc ttggctccag ccctgtaccc cttggtactg cctctgaaca ctctggtttc    2700
cccacccaac tgcggctaag tctctttttc ccttggatca gccaagcgaa acttggagct    2760
ttgacaagga actttcctaa gaaaccgctg ataaccagga caaaacacaa ccaagggtac    2820
acgcaggcat gcacgggttt cctgcccagc gacggcttaa gccagccccc gactggcctg    2880
gccacactgc tctccagtag cacagatgtc tgctcctcct cttgaacttg ggtgggaaac    2940
cccacccaaa gccccctttt gttacttagg caattcccct tccctgactc ccgagggcta    3000
gggctagagc agacccgggt aagtaaaggc agacccaggg ctcctctagc ctcatacccg    3060
tgccctcaca gagccatgcc ccggcacctc tgccctgtgt ctttcatacc tctacatgtc    3120
tgcttgagat atttcctcag cctgaaagtt tccccaacca tctgccagag aactcctatg    3180
catcccttag aaccctgctc agacaccatt acttttgtga acgcttctgc cacatcttgt    3240
cttccccaaa attgatcact ccgccttctc ctgggctccc gtagcacact ataacatctg    3300
ctggagtgtt gctgttgcac catactttct tgtacatttg tgtctccctt cccaactaga    3360
ctgtaagtgc cttgcggtca gggactgaat cttgcccgtt tatgtatgct ccatgtctag    3420
cccatcatcc tgcttggagc aagtaggcag gagctcaata aatgtttgtt gcatgaagga    3480
aaaaaaaaaa aaaaaaa                                                   3497
```

<210> SEQ ID NO 22
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = A or G

<400> SEQUENCE: 22
gggctctgca ggggccagtt cctccncctg tcctctgggg gggccctgag a 51

<210> SEQ ID NO 23

<400> SEQUENCE: 23

000

<210> SEQ ID NO 24
<211> LENGTH: 3345
<212> TYPE: DNA
<213> ORGANISM: Homo sapiens

<400> SEQUENCE: 24
cttgcctgtc tgcgtctaaa gcccctgccc agagtccgcc ttctcaggtc cagtactccc 60
agttcacctg ccctcgggag ccctccttcc ttcggaaaac tcccggctct gactcctcct 120
cagcccctcc ccccgccctg ctcaccttta attgagatgc taatgagatt cctgtcgctt 180
ccatccctgg ccggccagcg ggcgggctcc ccagccaggc cgctgcacct gtcaggggaa 240
caagctggag gagcaggacc ctagacctct gcagcccata ccaggtctca tggaggggaa 300
caagctggag gagcaggact ctagccctcc acagtccact ccagggctca tgaaggggaa 360
caagcgtgag gagcaggggc tgggccccga acctgcggcg ccccagcagc ccacggcgga 420
ggaggaggcc ctgatcgagt tccaccgctc ctaccgagag ctcttcgagt tcttctgcaa 480
caacaccacc atccacggcg ccatccgcct ggtgtgctcc cagcacaacc gcatgaagac 540
ggccttctgg gcagtgctgt ggctctgcac ctttggcatg atgtactggc aattcggcct 600
gcttttcgga gagtacttca gctaccccgt cagcctcaac atcaacctca actcggacaa 660
gctcgtcttc cccgcagtga ccatctgcac cctcaatccc tacaggtacc cggaaattaa 720
agaggagctg gaggagctgg accgcatcac agagcagacg ctctttgacc tgtacaaata 780
cagctccttc accactctcg tggccggctc ccgcagccgt cgcgacctgc gggggactct 840
gccgcacccc ttgcagcgcc tgagggtccc gcccccgcct cacggggccc gtcgagcccg 900
tagcgtggcc tccagcttgc gggacaacaa cccccaggtg gactggaagg actggaagat 960
cggcttccag ctgtgcaacc agaacaaatc ggactgcttc taccagacat actcatcagg 1020
ggtggatgcg gtgagggagt ggtaccgctt ccactacatc aacatcctgt cgaggctgcc 1080
agagactctg ccatccctgg aggaggacac gctgggcaac ttcatcttcg cctgccgctt 1140
caaccaggtc tcctgcaacc aggcgaatta ctctcacttc caccacccga tgtatggaaa 1200
ctgctatact ttcaatgaca agaacaactc caacctctgg atgtcttcca tgcctggaat 1260
caacaacggt ctgtccctga tgctgcgcgc agagcagaat gacttcattc ccctgctgtc 1320
cacagtgact ggggcccggg taatggtgca cgggcaggat gaacctgcct ttatggatga 1380
tggtggcttt aacttgcggc ctggcgtgga gacctccatc agcatgagga aggaaaccct 1440
ggacagactt gggggcgatt atggcgactg caccaagaat ggcagtgatg ttcctgttga 1500
gaacctttac ccttcaaagt acacacagca ggtgtgtatt cactcctgct tccaggagag 1560
catgatcaag gagtgtggct gtgcctacat cttctatccg cggccccaga acgtggagta 1620
ctgtgactac agaaagcaca gttcctgggg gtactgctac tataagctcc aggttgactt 1680
ctcctcagac cacctgggct gtttcaccaa gtgccggaag ccatgcagcg tgaccagcta 1740
ccagctctct gctggttact cacgatggcc ctcggtgaca tcccaggaat gggtcttcca 1800

-continued

```
gatgctatcg cgacagaaca attacaccgt caacaacaag agaaatggag tggccaaagt   1860

caacatcttc ttcaaggagc tgaactacaa aaccaattct gagtctccct ctgtcacgat   1920

ggtcaccctc ctgtccaacc tgggcagcca gtggagcctg tggttcggct cctcggtgtt   1980

gtctgtggtg gagatggctg agctcgtctt tgacctgctg gtcatcatgt tcctcatgct   2040

gctccgaagg ttccgaagcc gatactggtc tccaggccga gggggcaggg gtgctcagga   2100

ggtagcctcc accctggcat cctcccctcc ttcccacttc tgcccccacc ccatgtctct   2160

gtccttgtcc cagccaggcc ctgctccctc tccagccttg acagcccctc cccctgccta   2220

tgccaccctg ggcccccgcc catctccagg gggctctgca ggggccagtt cctccacctg   2280

tcctctgggg gggccctgag agggaaggag aggtttctca caccaaggca gatgctcctc   2340

tggtgggagg gtgctggccc tggcaagatt gaaggatgtg cagggcttcc tctcagagcc   2400

gcccaaactg ccgttgatgt gtggaggggga agcaagatgg gtaagggctc aggaagttgc   2460

tccaagaaca gtagctgatg aagctgccca gaagtgcctt ggctccagcc ctgtacccct   2520

tggtactgcc tctgaacact ctggtttccc cacccaactg cggctaagtc tctttttccc   2580

ttggatcagc caagcgaaac ttggagcttt gacaaggaac tttcctaaga aaccgctgat   2640

aaccaggaca aaacacaacc aagggtacac gcaggcatgc acgggtttcc tgcccagcga   2700

cggcttaagc cagcccccga ctggcctggc cacactgctc tccagtagca cagatgtctg   2760

ctcctcctct tgaacttggg tgggaaaccc cacccaaaag ccccctttgt tacttaggca   2820

attccccttc cctgactccc gagggctagg gctagagcag acccgggtaa gtaaaggcag   2880

acccagggct cctctagcct catacccgtg ccctcacaga gccatgcccc ggcacctctg   2940

ccctgtgtct ttcatacctc tacatgtctg cttgagatat ttcctcagcc tgaaagtttc   3000

cccaaccatc tgccagagaa ctcctatgca tcccttagaa ccctgctcag acaccattac   3060

ttttgtgaac gcttctgcca catcttgtct tccccaaaat tgatcactcc gccttctcct   3120

gggctcccgt agcacactat aacatctgct ggagtgttgc tgttgcacca tactttcttg   3180

tacatttgtg tctcccttcc caactagact gtaagtgcct tgcggtcagg gactgaatct   3240

tgcccgttta tgtatgctcc atgtctagcc catcatcctg cttggagcaa gtaggcagga   3300

gctcaataaa tgtttgttgc atgaaggaaa aaaaaaaaaa aaaaa                  3345

<210> SEQ ID NO 25

<400> SEQUENCE: 25

000

<210> SEQ ID NO 26
<211> LENGTH: 3970
<212> TYPE: DNA
<213> ORGANISM: Homo sapiens

<400> SEQUENCE: 26

gcacccaggt cgggcggtgg gggcgagcgg aggggctgag gggcggagag gcctggcggg     60

ccgctgctgc gggccagggg acgggggcgg agccggagcc ggagccgacg ggcggtggcc    120

gcactgggac cccggaatcc cgcgcgctgc ccacgattcg cttctgagga acctagaaag    180

attgtacaat gaatggtgat tctcgtgctg cggtggtgac ctcaccaccc ccgaccacag    240

cccctcacaa ggagaggtac ttcgaccgag tagatgagaa caacccagag tacttgaggg    300

agaggaacat ggcaccagac cttcgccagg acttcaacat gatggagcaa aagaagaggg    360
```

-continued

```
tgtccatgat tctgcaaagc cctgctttct gtgaagaatt ggaatcaatg atacaggagc    420
aatttaagaa ggggaagaac cccacaggcc tattggcatt acagcagatt gcagatttta    480
tgaccacgaa tgtaccaaat gtctacccag cagctccgca aggagggatg gctgccttaa    540
acatgagtct tggtatggtg actcctgtga acgatcttag aggatctgat tctattgcgt    600
atgacaaagg agagaagtta ttacggtgta aattggcagc gttttataga ctagcagatc    660
tctttgggtg gtctcagctt atctacaatc atatcacaac cagagtgaac tccgagcagg    720
aacacttcct cattgtccct tttgggcttc tttacagtga agtgactgca tccagtttgg    780
ttaagatcaa tctacaagga gatatagtag atcgtggaag cactaatctg ggagtgaatc    840
aggccggctt caccttacac tctgcaattt atgctgcacg cccggacgtg aagtgcgtcg    900
tgcacattca caccccagca ggggctgcgg tctctgcaat gaaatgtggc ctcttgccaa    960
tctccccgga ggcgctttcc cttggagaag tggcttatca tgactaccat ggcattctgg   1020
ttgatgaaga ggaaaaagtt ttgattcaga aaaatctggg gcctaaaagc aaggttctta   1080
ttctccggaa ccatgggctc gtgtcagttg gagagagcgt tgaggaggcc ttctattaca   1140
tccataacct tgtggttgcc tgtgagatcc aggttcgaac tctggccagt gcaggaggac   1200
cagacaactt agtcctgctg aatcctgaga agtacaaagc caagtcccgt tccccagggt   1260
ctccggtagg ggaaggcact ggatcgcctc ccaagtggca gattggtgag caggaatttg   1320
aagccctcat gcggatgctc gataatctgg gctacagaac tggctaccct tatcgatacc   1380
ctgctctgag agagaagtct aaaaaataca gcgatgtgga ggttcctgct agtgtcacag   1440
gttactcctt tgctagtgac ggtgattcgg gcacttgctc cccactcaga cacagttttc   1500
agaagcagca gcgggagaag acaagatggc tgaactctgg ccggggcgac gaagcttccg   1560
aggaagggca gaatggaagc agtcccaagt cgaagactaa gtggactaaa gaggatggac   1620
atagaacttc cacctctgct gtccctaacc tgtttgttcc attgaacact aacccaaaag   1680
aggtccagga gatgaggaac aagatccgag agcagaattt acaggacatt aagacggctg   1740
gccctcagtc ccaggttttg tgtggtgtag tgatggacag gagcctcgtc cagggagagc   1800
tggtgacggc ctccaaggcc atcattgaaa aggagtacca gccccacgtc attgtgagca   1860
ccacgggccc caaccccttc accacactca cagaccgtga gctggaggag taccgcaggg   1920
aggtggagag gaagcagaag ggctctgaag agaatctgga cgaggctaga gaacagaaag   1980
aaaagagtcc tccagaccag cctgcggtcc cccacccgcc tcccagcact cccatcaagc   2040
tggaggaaga ccttgtgccg gagccgacta ctggagatga cagtgatgct gccaccttta   2100
agccaactct ccccgatctg tcccctgatg aaccttcaga agcactcggc ttcccaatgt   2160
tagagaagga ggaggaagcc catagacccc caagccccac tgaggcccct actgaggcca   2220
gccccgagcc agccccagac ccagccccgg tggctgaaga ggctgccccc tcagctgtcg   2280
aggagggggc cgccgcggac cctggcagcg atgggtctcc aggcaagtcc ccgtccaaaa   2340
agaagaagaa gttccgtacc ccgtcctttc tgaagaagag caagaagaag agtgactcct   2400
gaaagccctg cgctaacact gtcctgtccg gagcgaccct ggctctgcca gcgtccccgg   2460
ccacgtctgt gctctgtcct tgtgtaatgg aatgcaaaaa agccaagccc tccgcctaga   2520
ggtcccctca cgtgaccagc cccgtgtagc cccgggctga cccagtgtgt gctcagcagc   2580
cccaccccac cctgcccctt gtcctctcag agcctcagct tctgggggag acatgctctc   2640
cccacagggg ggaggcacta agtcatggtc ctggctggaa ggtactgaag gcttctgcag   2700
ctttggctgc acgtcaccct cctgagcctc acctttcctg ccgtccctcc tgttgtgaaa   2760
```

```
tcaccacatt ctgtctctgc ttggcttccc ctccacccta aagtctcagg tgacggactc   2820

agactcctgg cttcatgtgg cattctctct gctcagtgat ctcacttaaa tctatataca   2880

aagccttggt cccgtgaaaa cactcgtgtg cccaccagcg gccttgaaga ggcaggtctg   2940

ggccagatgc tgggcaggaa accccagcgg cagatgggcc tgtgtgcacc caacgtgatg   3000

ctatgcatgt ctgaccgacg atccctcgac cagaatcaga ttcaggagct cagtttcttt   3060

ttcacttggg tctctggatt cctgtcatag ggaaggtata tcaggagggg aagaggcctt   3120

tctagaattt tctttgagca ggtttacaat ttagcttaca tttttcgact gtgaacgtga   3180

ataggctgct ttttgctttc ttctttccag accccacagt agagcacttt tcacttattt   3240

gggggaggct tcaggggact gttctcacct taactcagcc agaaagatgc cctagttgtg   3300

atcaaaggta actcgaggtg gagggtagcc ctggggcccc tcgacatcac cgtcattgat   3360

ggagcctgaa ccgtgtgctc ctcggcagat gctgttgttg ttacttccct ccaagaggct   3420

ggaaaagggc tcagagctgc tgagcaggaa ccggagggtg acccatttca ggaggtgccg   3480

gtaccagcct gactaggtac aggcaagctt gtgtgggccc aacaggccct tggtagagct   3540

ggtgccagat gtgggctcag atcctgggca tgatgggccg agccacctcg gatcccactg   3600

attggccagc cgagcgagaa ccaggctgct gcatggcact gaccgccgct tccagcttcc   3660

tctgagccgc agggcctgct acgcgggcaa gcgtgctgcc tctcttctgt gtcgttttgt   3720

tgccaaggca gaatgaaaag tccttaaccg tggactcttc ctttatcccc tcctttaccc   3780

cacatatgca atgactttta attttcactt ttgtagttta atcctttgta ttacaacatg   3840

aaatatagtt gcatatatgg acaccgactt gggaggacag gtcctgaatg tcctttctcc   3900

agtgtaacat gttttactca caaataaaat tctttcagca agttccttgt ctaaaaaaaa   3960

aaaaaaaaaa                                                          3970
```

```
<210> SEQ ID NO 27
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = G or T

<400> SEQUENCE: 27

ccggggcgac gaagcttccg aggaanggca gaatggaagc agtcccaagt c              51


<210> SEQ ID NO 28

<400> SEQUENCE: 28

000


<210> SEQ ID NO 29
<211> LENGTH: 5582
<212> TYPE: DNA
<213> ORGANISM: Homo sapiens

<400> SEQUENCE: 29

ctggcccctc cctggacacc caggcgacaa tggcagaact gcccacaaca gagacgcctg     60

gggacgccac tttgtgcagc gggcgcttca ccatcagcac actgctgagc agtgatgagc    120

cctctccacc agctgcctat gacagcagcc accccagcca cctgacccac agcagcacct    180

tctgcatgcg cacctttggc tacaacacga tcgatgtggt gcccacatat gagcactatg    240
```

```
ccaacagcac ccagcctggt gagccccgga aggtccggcc cacactggct gacctgcact    300
ccttcctcaa gcaggaaggc agacacctgc atgccctggc ctttgacagc cggcccagcc    360
acgagatgac tgatgggctg gtggagggcg aggcaggcac cagcagcgag aagaaccccg    420
aggagccagt gcgcttcggc tgggtcaagg gggtgatgat tcgttgcatg ctcaacattt    480
ggggcgtgat cctctacctg cggctgccct ggattacggc ccaggcaggc atcgtcctga    540
cctggatcat catcctgctg tcggtcacgg tgacctccat cacaggcctc tccatctcag    600
ccatctccac caatggcaag gtcaagtcag gtggcaccta cttcctcatc tcccggagtc    660
tgggcccaga gcttgggggc tccatcggcc tcattttcgc tttcgccaat gccgtgggtg    720
tggccatgca cacggtgggc tttgcagaga ccgtgcggga cctgctccag gagtatgggg    780
cacccatcgt ggaccccatt aacgacatcc gcatcattgg cgtggtctcg gtcactgtgc    840
tgctggccat ctccctggct ggcatggagt gggagtccaa ggcccaggtg ctgttcttcc    900
ttgtcatcat ggtctccttt gccaactatt tagtggggac gctgatcccc ccatctgagg    960
acaaggcctc caaaggcttc ttcagctacc gggcggacat ttttgtccag aacttggtgc   1020
ctgactggcg gggtccagat ggcaccttct tcggaatgtt ctccatcttc ttcccctcgg   1080
ccacaggcat cctggcaggg gccaacatat ctggtgacct caaggaccct gctatagcca   1140
tccccaaggg gaccctcatg gccattttct ggacgaccat ttcctacctg gccatctcag   1200
ccaccattgg ctcctgcgtg gtgcgtgatg cctctggggt cctgaatgac acagtgaccc   1260
ctggctgggg tgcctgcgag ggctggcct gcagctatgg ctggaacttc accgagtgca   1320
cccagcagca cagctgccac tacggcctca tcaactatta ccagaccatg agcatggtgt   1380
caggcttcgc gcccctgatc acggctggca tcttcggggc caccctctcc tctgccctgg   1440
cctgccttgt ctctgctgcc aaagtcttcc agtgcctttg cgaggaccag ctgtacccac   1500
tgatcggctt cttcggcaaa ggctatggca agaacaagga gcccgtgcgt ggctacctgc   1560
tggcctacgc catcgctgtg gccttcatca tcatcgctga gctcaacacc atagccccca   1620
tcatttccaa cttcttcctc tgctcctatg ccctcatcaa cttcagctgc ttccacgcct   1680
ccatcaccaa ctcgcctggg tggagacctt cattccaata ctacaacaag tgggcggcgc   1740
tgtttggggc tatcatctcc gtggtcatca tgttcctcct cacctggtgg gcggccctca   1800
tcgccattgg cgtggtgctc ttcctcctgc tctatgtcat ctacaagaag ccagaggtaa   1860
attggggctc ctcggtacag gctggctcct acaacctggc cctcagctac tcggtgggcc   1920
tcaatgaggt ggaagaccac atcaagaact accgccccca gtgcctggtg ctcacggggc   1980
cccccaactt ccgcccggcc ctggtggact ttgtgggcac cttcacccgg aacctcagcc   2040
tgatgatctg tggccacgtg ctcatcggac cccacaagca gaggatgcct gagctccagc   2100
tcatcgccaa cgggcacacc aagtggctga acaagaggaa gatcaaggcc ttctactcgg   2160
atgtcattgc cgaggacctc cgcagaggcg tccagatcct catgcaggcc gcaggtctcg   2220
ggagaatgaa gcccaacatt ctggtggttg ggttcaagaa gaactggcag tcggctcacc   2280
cggccacagt ggaagactac attggcatcc tccatgatgc ctttgatttc aactatggcg   2340
tgtgtgtcat gaggatgcgg gagggactca acgtgtccaa gatgatgcag gcgcacatta   2400
accccgtgtt tgacccagcg gaggacggga aggaagccag cgccagaggt gccaggccat   2460
cagtctctgg cgctttggac cccaaggccc tggtgaagga ggagcaggcc accaccatct   2520
tccagtcgga gcagggcaag aagaccatag acatctactg gctctttgac gatggaggcc   2580
```

-continued

```
tcaccctcct cattccctat ctccttggcc gcaagaggag gtggagcaaa tgcaagatcc   2640
gtgtgttcgt aggcggccag attaacagga tggaccagga gagaaaggcg atcatttctc   2700
tgctgagcaa gttccgactg ggattccatg aagtccacat cctccctgac atcaaccaga   2760
accctcgggc tgagcacacc aagaggtttg aggacatgat tgcacccttc cgtctgaatg   2820
atggcttcaa ggatgaggcc actgtcaacg agatgcggcg ggactgcccc tggaagatct   2880
cagatgagga gattacgaag aacagagtca agtcccttcg gcaggtgagg ctgaatgaga   2940
ttgtgctgga ttactcccga gacgctgctc tcatcgtcat cactttgccc atagggagga   3000
aggggaagtg ccccagctcg ctgtacatgg cctggctgga gaccctgtcc caggacctca   3060
gacctccagt catcctgatc cgaggaaacc aggaaaacgt gctcaccttt tactgccagt   3120
aactccaggc tttgacatcc ctgtccacag ctctgagtgt gtgggataag ttggaacttg   3180
attgcctcta gtccacaggg atgagactca tgttctgttg cactttaagt ggcagcatct   3240
gatgatctca ccgaaaaaga tggtagattt ccaaatctgg ctggactcca cttccatggg   3300
acacattccc tgggtcttgt gtttataggc tagagaaata gcagatggag ctgcaaggaa   3360
aactctctaa agcatcctat tccttttaaa ggatttcttt tgattttgat gaccattaat   3420
taagagttca gtctttgatt tgtatgcaaa ttggagtccc aatgctgggc gtgaatcttg   3480
acagtttcta cagaccttcc tgggtgaaag ttcctaaatc atgccctgct tcctccaata   3540
ggagaatggg agcctcacct gtaggaccta caggctctct aaggaatgca ggtctctctc   3600
tgagcctcca cagccaggca aatacatata tatatatttt ttttttagat gaagtttttt   3660
ctcttgttgc ccaggctagg gtgtaatggc atgatctcag gtcactgcaa cctcctcccg   3720
ggttcaagca tttcttctgt ctcagcctcc cgaatagctg ggattacagg cacctgccat   3780
cacacgagct aatttttgta tttttagtag agatggggtt tcaccatgtt gaccaggctg   3840
gtgttgagct cctgacctca ggtgatccac ccacctcggt ctcccaaagt gctggggtta   3900
caggcctgag ccactgcgcc cggcccaggc aaatttcttg aaccacttct cactcccgtc   3960
actttcaata aggggtcttt gatgtcttca ctggttcttt ggacgaggga cttttcgaac   4020
tttttttggtt gcaacacaca gtaagaaata tacttcacac tgagacttgc agcgcacaca   4080
cacggaaacg accaaaacaa aaatgtcaca aaacaatact tacccttccc tgggggacgt   4140
cctccagtat gttctgttct gtttattttt cactgttggt tgcaatccaa taaaatgact   4200
ttgggatcca ctcatgggtg gggacccaca catttgaaag gcatggccac ctttctgttg   4260
tgccttgcat ttgtccacac acagggagtc tggctgagct ggggaaaggc cacggctggg   4320
tgtcattgcc attttcccag ctcatctcac cgggaagaaa agcagattga cagaacacgt   4380
gaggaggggt attgatggca ggagagtcaa aaaagagttt taaagaaggg gcaaggttga   4440
aggagtctag tggcaagggt aagatttcag gcatggttaa gaacagacga caaggatgtc   4500
aggaatgaag atgtggagag gggtgtagag atggcaaggt tggcaaggaa cagataggca   4560
ggagcaggtc caagccaagc ctagcccaag accaggtgaa aggagagggg aggaggagcc   4620
acctgcaaga gatggaaaga gcaggcggca gagggggctg gcagggaggg gctgttaaga   4680
gtggggttgg aggtgggaga gaagctagga caagggagat ggagaaagga cctatacctg   4740
gctcacggaa ggccttcagg tcactacacg ttgaacatcc ccagtgtttg agcccccaaa   4800
gctagggtgc aagagcactg ccatcgaatg ccagtgggtg aggccaagtg agggtatttg   4860
cagctctaga cataaccaag aagcgtaaag gtgagttgtt tggtggtacg actgcctgtg   4920
ccttcttccg atggcactgg ggtggctgaa ggaacagaca tctttgggtt tcatcagcct   4980
```

cctccaagac tgctgcagtg cctacacttt agacttcaga aggagactaa agacttctag 5040
aatttagaag gagatctgaa gtctcctttc tggagttaca acccaaagga tgttagcatt 5100
tctcaggtca tcccactgca aagcccagaa ggcttggggc tcccaggctg ctctgaagcc 5160
ccactgtctg accgcctcag ggcttgctac gagggactgg ggcacggcca agctgactag 5220
gaacagctct cgtgctcctg agggacctgg aggatgggcc tgcctcccag ccattgagct 5280
ggattctggg ataattctta actcgaaata aggggaagca tccatcaggg aatgctggcc 5340
tttctagagc cacgtagaaa acaattttct ggttcttcaa acctcaaaga gtccttggtc 5400
caaaaaacag aatgttttgg cttcgggtgt caaaaaaaaa atttcacga tgtcagaaat 5460 agtatgtttt taacaatagt aatagctttg taaaaaaata aaaagcttta acagcgaggc 5520
cataaacaat gaaatgaata aaaacggtgg tcattcagtc aacggaaaaa aaaaaaaaaa 5580
aa 5582

<210> SEQ ID NO 30
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or G

<400> SEQUENCE: 30
cccattaacg acatccgcat cattgncgtg gtctcggtca ctgtgctgct g 51

<210> SEQ ID NO 31

<400> SEQUENCE: 31

000

<210> SEQ ID NO 32

<400> SEQUENCE: 32

000

<210> SEQ ID NO 33
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or T

<400> SEQUENCE: 33
cacttcctcc aaaaaaaaag aaaacnccat ttcccctcaa ctcttccagt t 51

<210> SEQ ID NO 34
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or G

<400> SEQUENCE: 34
aatgttaaca gtatagaaaa ttttanctca acaaatagag aatatcagta a 51

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 3889
<212> TYPE: DNA
<213> ORGANISM: Homo sapiens

<400> SEQUENCE: 50
cagcagcagc tccagctcgg tgcagaagcc cagcagccgg cgtgccgccg cccggccact 60
ccagcgcctt cttccccgcc ttgcgctcct gccccaactc gcgctgtcgt cggaccccgg 120
cccatccagc agcgctcggc gcccaccagg cggacgccca ggagaacccc tgcctccgtc 180
gcggctcctg gagagctgat cgttcacctg ccccggcccg cctgaggacg ggggtgcctt 240
catgcggccc ccacactcct caccccgccg ccgccgccgt cccggagctc cgcacagtgt 300
gccccagccc cagcagggcg cacaactttg gaagtctcgc ggcgctccga gaggcggcag 360
agtccgcgcc ccagccccgg gccgggccgg gccagaaccg cagcgtctgg gggaagccag 420
agagtcggta atcgcttcgg ggatgtaagg cgacagacat aggacccccg agctcgcatc 480
agcacccttc ggctgcctcc cggggtgggg gcgggccccg cacacggtaa gacctcttgc 540
tttcgctcag gctcaagatt caagatacag atattgatat gtatatatat atttaatttc 600
ctgtcatcct tccaagttat caggccaccg atgatttttg ttctcccttc ttgaagaata 660
aatctctctt tacccatcgg ctctccctac tctctcccgc cgcttagaaa taaaacttgg 720
ctgtattagg agctcggagc aagaaggcgc ccaccgagag cgtctgaagc gcgagccagg 780
cgcagttcgc gggacccggg ccatgggccg ctagcggtcc tccagttcgg gcccggcctc 840
cctgcggccc cctccctatg tgagccgcag ccaggcgagc ggggcgccgg aggaagagga 900
ggacccacgg gcgccgggcc ggaaggcagc tggcagcagg cccaggccag cgggcgcccg 960
cgttcatgtt ccgccaggag cagccgttgg ccgagggcag ctttgcgccc atgggctccc 1020
tgcagccgga cgcgggcaac gcgagctgga acgggaccga ggcgccgggg ggcggcgccc 1080
gggccacccc ttactccctg caggtgacgc tgacgctggt gtgcctggcc ggcctgctca 1140
tgctgctcac cgtgttcggc aacgtgctcg tcatcatcgc cgtgttcacg agccgcgcgc 1200
tcaaggcgcc ccaaaacctc ttcctggtgt ctctggcctc ggccgacatc ctggtggcca 1260
cgctcgtcat ccctttctcg ctggccaacg aggtcatggg ctactggtac ttcggcaagg 1320
cttggtgcga gatctacctg gcgctcgacg tgctcttctg cacgtcgtcc atcgtgcacc 1380

```
tgtgcgccat cagcctggac cgctactggt ccatcacaca ggccatcgag tacaacctga   1440
agcgcacgcc gcgccgcatc aaggccatca tcatcaccgt gtgggtcatc tcggccgtca   1500
tctccttccc gccgctcatc tccatcgaga agaagggcgg cggcggcggc ccgcagccgg   1560
ccgagccgcg ctgcgagatc aacgaccaga agtggtacgt catctcgtcg tgcatcggct   1620
ccttcttcgc tccctgcctc atcatgatcc tggtctacgt gcgcatctac cagatcgcca   1680
agcgtcgcac ccgcgtgcca cccagccgcc ggggtccgga cgccgtcgcc gcgccgccgg   1740
ggggcaccga gcgcaggccc aacggtctgg gccccgagcg cagcgcgggc ccgggggggcg   1800
cagaggccga accgctgccc acccagctca acggcgcccc tggcgagccc gcgccggccg   1860
ggccgcgcga caccgacgcg ctggacctgg aggagagctc gtcttccgac cacgccgagc   1920
ggcctccagg gccccgcaga cccgagcgcg gtccccgggg caaaggcaag gcccgagcga   1980
gccaggtgaa gccgggcgac agcctgccgc ggcgcgggcc gggggcgacg gggatcggga   2040
cgccggctgc agggccgggg gaggagcgcg tcggggctgc caaggcgtcg cgctggcgcg   2100
ggcggcagaa ccgcgagaag cgcttcacgt tcgtgctggc cgtggtcatc ggagtgttcg   2160
tggtgtgctg gttccccttc ttcttcacct acacgctcac ggccgtcggg tgctccgtgc   2220
cacgcacgct cttcaaattc ttcttctggt tcggctactg caacagctcg ttgaacccgg   2280
tcatctacac catcttcaac cacgatttcc gccgcgcctt caagaagatc ctctgtcggg   2340
gggacaggaa gcggatcgtg tgaggtttcc gctggcgccc gcgtagactc acgctgactg   2400
caggcagcgg ggggcatcga ggggtgctta gccccagggc actcagaaac ccgggcgctg   2460
cctgctctgc gtttcctcgt ctggggtggc tctgcagcct cctgcgggcg ggcgtctgct   2520
gctcctacaa gggaagcttc ttgctgccag gcccacacat ccccagttgt tggtttggcc   2580
actcttgacc tggagccatc ttcctagtgg gccacccct a atcactattg cttcctaaag   2640
gtattttcac cctcttcgcc tggtacagcc ctcacagctc ttcagagcaa gcactggact   2700
acaagggcat ggctcacaaa aggttaatgg atgggggtta cctagccctg gctaattccc   2760
cttccattcc caactctctc tctcttttta aagaaaaatg ctaagggcag ccctgcctgc   2820
cctccccatc ccccgctgta aatatacact atttttgata gcacacatgg ggcccccata   2880
tctcttggcc ttggttttga tgttgaaatc ctggccttgg gagagatgcc ttccaggcag   2940
acacagctgt ctggttcagg ccaagcccct ttgcaatgca agccctttct ggtgttatga   3000
agtccctcta tgtcgtcgtt ttcaccagca actggtgact gtcccttcga cacggacctg   3060
ctttgagatt tcctgacagg gaaaagattt ctgtccattt ttttcctgtg cctaacagca   3120
taattgcctt ttcctatgta aatattatga tggtggatca agacataagt aaatgagcct   3180
ttctgcctca catcagccct gtgtataaag ccattattct ctgatgcact gtttgcccca   3240
gtaactcact ttaaaacctc tctttccagt gttccctctc tccctccagg gccactgctt   3300
gaagaagaat atgtatgttt ctatcttgta tgtctgtgtg cccctcctgc cccgaaagtg   3360
ctgactatgg ggaaatcttt tagctgctgt ttttagactc caaggagtgg aaattatgtg   3420
gaagaagcaa acctgataca atttgcccaa ggtaaacagt ttgaaaagac aaatgggcct   3480
gccaaactgt acagtttctt ccccaagagc tgttaggtat caaaatgttg tcctttcccc   3540
cctccgtgct tttctggttg agatcatgtc attgatgaac tgccaaagtc aggggaggag   3600
ggcagagact ttgtgtttac atctgcattt ctacatgttt tagacagaga caatttaagg   3660
cctgcactct tatttcacta aagaaaaact aatgtcagca catgttgcta atgacagtgg   3720
```

-continued

```
atttttttt aaataaaaaa gtttacagat caaatgtgaa ataaatatga atggagtggt   3780

cctcttgtct gttatctgag ttttcaaaag ctttaagact ctgggaacat ctgattttat   3840

ggattttta aaaataaaaa atgtacatta taaaaaaaaa aaaaaaaaa                3889
```

<210> SEQ ID NO 51
<211> LENGTH: 1958
<212> TYPE: DNA
<213> ORGANISM: Homo sapiens

<400> SEQUENCE: 51

```
ccggctccag gagggacggc gtagctcgcg ggaggaccat ggcgtccccg gcgctggcgg     60

cggcgctggc ggtggcggca gcggcgggcc ccaatgcgag cggcgcgggc gagaggggca    120

gcggcggggt tgccaatgcc tcgggggctt cctgggggcc gccgcgcggc cagtactcgg    180

cgggcgcggt ggcagggctg gctgccgtgg tgggcttcct catcgtcttc accgtggtgg    240

gcaacgtgct ggtggtgatc gccgtgctga ccagccgggc gctgcgcgcg ccacagaacc    300

tcttcctggt gtcgctggcc tcggccgaca tcctggtggc cacgctggtc atgcccttct    360

cgttggccaa cgagctcatg gcctactggt acttcgggca ggtgtggtgc ggcgtgtacc    420

tggcgctcga tgtgctgttt tgcacctcgt cgatcgtgca tctgtgtgcc atcagcctgg    480

accgctactg gtcggtgacg caggccgtcg agtacaacct gaagcgcaca ccacgccgcg    540

tcaaggccac catcgtggcc gtgtggctca tctcggccgt catctccttc ccgccgctgg    600

tctcgctcta ccgccagccc gacggcgccg cctacccgca gtgcggcctc aacgacgaga    660

cctggtacat cctgtcctcc tgcatcggct ccttcttcgc gccctgcctc atcatgggcc    720

tggtctacgc gcgcatctac cgagtggcca agctgcgcac gcgcacgctc agcgagaagc    780

gcgcccccgt gggccccgac ggtgcgtccc cgactaccga aaacgggctg ggcgcggcgg    840

caggcgcagg cgagaacggg cactgcgcgc ccccgcccgc cgacgtggag ccggacgaga    900

gcagcgcagc ggccgagagg cggcggcgcc ggggcgcgtt gcggcggggc gggcggcggc    960

gagcgggcgc ggagggggc gcgggcggtg cggacgggca gggggcgggg ccgggggcgg   1020

ctgagtcggg ggcgctgacc gcctccaggt ccccggggcc cggtggccgc ctgtcgcgcg   1080

ccagctcgcg ctccgtcgag ttcttcctgt cgcgccggcg ccgggcgcgc agcagcgtgt   1140

gccgccgcaa ggtggcccag gcgcgcgaga agcgcttcac ctttgtgctg gctgtggtca   1200

tgggcgtgtt cgtgctctgc tggttcccct tcttcttcag ctacagcctg tacggcatct   1260

gccgcgaggc ctgccaggtg cccggcccgc tcttcaagtt cttcttctgg atcggctact   1320

gcaacagctc gctcaacccg gtcatctaca cggtcttcaa ccaggatttc cggcgatcct   1380

ttaagcacat cctcttccga cggaggagaa ggggcttcag gcagtgactc gcacccgtct   1440

gggaatcctg gacagctccg cgctcggggc tgggcagaag ggcggcccg gacgggggag   1500

ctttcccaga gacccgggga tggattggcc tccagggcgc aggggagggt gcggcagggc   1560

aggagcttgg cagagagata gccgggctcc agggagtggg gaggagagag gggagaccc   1620

ctttgccttc ccccctcagc aaggggctgc ttctggggct ccctgcctgg atccagctct   1680

gggagccctg ccgaggtgtg gctgtgaggt cagggtttta gagagcagtg gcagaggtag   1740

ccccctaaat gggcaagcaa ggagcccccc aaagacacta ccactcccca tccccgtctg   1800

accaagggct gacttctcca ggacctagtc ggggggtggc tgccaggggg caaggagaaa   1860

gcaccgacaa tctttgatta ctgaaagtat ttaaatgttt gccaaaaaca acagccaaaa   1920

caaccaaact attttctaaa taaacctttg taatctaa                           1958
```

<210> SEQ ID NO 52
<211> LENGTH: 1462
<212> TYPE: DNA
<213> ORGANISM: Homo sapiens

<400> SEQUENCE: 52
agaacctcag tggatctcag agagagcccc agactgaggg aagcatggat ggatggagaa 60
ggatgcctcg ctggggactg ctgctgctgc tctggggctc ctgtaccttt ggtctcccga 120
cagacaccac cacctttaaa cggatcttcc tcaagagaat gccctcaatc cgagaaagcc 180
tgaaggaacg aggtgtggac atggccaggc ttggtcccga gtggagccaa cccatgaaga 240
ggctgacact tggcaacacc acctcctccg tgatcctcac caactacatg gacacccagt 300
actatggcga gattggcatc ggcaccccac cccagacctt caaagtcgtc tttgacactg 360
gttcgtccaa tgtttgggtg ccctcctcca agtgcagccg tctctacact gcctgtgtgt 420
atcacaagct cttcgatgct tcggattcct ccagctacaa gcacaatgga acagaactca 480
ccctccgcta ttcaacaggg acagtcagtg gctttctcag ccaggacatc atcaccgtgg 540
gtggaatcac ggtgacacag atgtttggag aggtcacgga gatgcccgcc ttacccttca 600
tgctggccga gtttgatggg gttgtgggca tgggcttcat tgaacaggcc attggcaggg 660
tcacccctat cttcgacaac atcatctccc aaggggtgct aaaagaggac gtcttctctt 720
tctactacaa cagagattcc gagaattccc aatcgctggg aggacagatt gtgctgggag 780
gcagcgaccc ccagcattac gaagggaatt tccactatat caacctcatc aagactggtg 840
tctggcagat tcaaatgaag ggggtgtctg tggggtcatc caccttgctc tgtgaagacg 900
gctgcctggc attggtagac accggtgcat cctacatctc aggttctacc agctccatag 960
agaagctcat ggaggccttg ggagccaaga agaggctgtt tgattatgtc gtgaagtgta 1020
acgagggccc tacactcccc gacatctctt tccacctggg aggcaaagaa tacacgctca 1080
ccagcgcgga ctatgtattt caggaatcct acagtagtaa aaagctgtgc acactggcca 1140
tccacgccat ggatatcccg ccacccactg gacccacctg ggccctgggg gccaccttca 1200
tccgaaagtt ctacacagag tttgatcggc gtaacaaccg cattggcttc gccttggccc 1260
gctgaggccc tctgccaccc aggcaggccc tgccttcagc cctggcccag agctggaaca 1320
ctctctgaga tgcccctctg cctgggctta tgccctcaga tggagacatt ggatgtggag 1380
ctcctgctgg atgcgtgccc tgacccctgc accagccctt ccctgctttg aggacaaaga 1440
gaataaagac ttcatgttca ca 1462

<210> SEQ ID NO 53
<211> LENGTH: 10796
<212> TYPE: DNA
<213> ORGANISM: Homo sapiens

<400> SEQUENCE: 53
agactcccgg cgccatttag cgcggagagt ttcccgggtg gacgcggctc ctctctcggc 60
cactccgcac ccccatcttc ggtgacagaa ggcgcctggt gggggtggct gctcttttct 120
ctccctgttc cccctcaccc agtcctctag gtctcctctc ctcttgcctc agagaagcag 180
cggagctcgg gccccgcggt gagcggccct cccctccccg ccgttccctc ctccgtcagc 240
ccccggcacc ggcccgggag gagacgggtt tgccaggcct ggggcgggcg gggaggcctc 300
ggggaagggg gggcccgctc ctcaggcgcc gaggctccga ggctccggcc cttcgcctct 360

-continued

```
gggcgatggg cgacctgtga ggccggtccc catcgctggg ggcgcgtgtg ggaggaggcg    420
gccgcccgag tgaccgggag ccgggccgcg gccttccctc gcccgcctcg gcccctccca    480
ctcctctgcc ccggggccgc caccgcccgg gcgtcggacc tggtcccgtg ctcgcggtgc    540
cgccgccctc tgggcctagc ccgcccagct cggcgagcgg cggcagtggg agccgcgtcc    600
gccgcatccg cctcgactcg gtgccggccc ctggccctcc cctcatgact gcggcgcctc    660
tgctgccacc gcccgcccgg ccgccgctcg ccgcaggatg gatgcggacc gtgcggcgct    720
aacccccgtg gctcagctcc cgaatcgccc gccttcgagc cctcctcgtg agccgcagca    780
gcctcggtgc cagcccccgc cgcagctggg cccagcggtc cgcctgtccc tcgttgcggc    840
ttgtcggtgc tgagtgaggc gtcgtccggg tcggcgcgaa cccgcccggc cgcggttccc    900
tgcagacctc tgcgcgggcg gctcggccct tcacgccctt ttcgttcacg aatccgagcc    960
cgctcgcctc tctccagcga accgaccatg tctggcggcg ccgcagagaa gcagagcagc   1020
actcccggtt ccctgttcct ctcgccgccg gctcctgccc ccaagaatgg ctccagctcc   1080
gattcctccg tgggggagaa actgggagcc gcggccgccg acgctgtgac cggcaggacc   1140
gaggagtaca ggcgccgccg ccacactatg gacaaggaca gccgtggggc ggccgcgacc   1200
actaccacca ctgagcaccg cttcttccgc cggagcgtca tctgtgactc caatgccact   1260
gcactggagc ttcccggcct tcctctttcc ctgccccagc ccagcatccc cgcggctgtc   1320
ccgcagagtg ctccaccgga gccccaccgg gaagagaccg tgaccgccac cgccacttcc   1380
caggtagccc agcagcctcc agccgctgcc gcccctgggg aacaggccgt cgcgggccct   1440
gcccccctcga ctgtccccag cagtaccagc aaagaccgcc cagtgtccca gcctagcctt   1500
gtggggagca aagaggagcc gccgccggcg agaagtggca gcggcggcgg cagcgccaag   1560
gagccacagg aggaacggag ccagcagcag gatgatatcg aagagctgga gaccaaggcc   1620
gtgggaatgt ctaacgatgg ccgctttctc aagtttgaca tcgaaatcgg cagaggctcc   1680
tttaagacgg tctacaaagg tctggacact gaaaccaccg tggaagtcgc ctggtgtgaa   1740
ctgcaggatc gaaaattaac aaagtctgag aggcagagat ttaaagaaga agctgaaatg   1800
ttaaaaggtc ttcagcatcc caatattgtt agattttatg attcctggga atccacagta   1860
aaaggaaaga agtgcattgt tttggtgact gaacttatga cgtctggaac acttaaaacg   1920
tatctgaaaa ggtttaaagt gatgaagatc aaagttctaa gaagctggtg ccgtcagatc   1980
cttaaaggtc ttcagtttct tcatactcga actccaccta tcattcaccg cgatcttaaa   2040
tgtgacaaca tctttatcac cggccctact ggctcagtca agattggaga cctcggtctg   2100
gcaaccctga agcgggcttc ttttgccaag agtgtgatag gtaccccaga gttcatggcc   2160
cctgagatgt atgaggagaa atatgatgaa tccgttgacg tttatgcttt tgggatgtgc   2220
atgcttgaga tggctacatc tgaatatcct tactcggagt gccaaaatgc tgcacagatc   2280
taccgtcgcg tgaccagtgg ggtgaagcca gccagttttg acaaagtagc aattcctgaa   2340
gtgaaggaaa ttattgaagg atgcatacga caaaacaaag atgaaagata ttccatcaaa   2400
gacctttga accatgcctt cttccaagag gaaacaggag tacgggtaga attagcagaa   2460
gaagatgatg gagaaaaaat agccataaaa ttatggctac gtattgaaga tattaagaaa   2520
ttaaagggaa aatacaaaga taatgaagct attgagtttt cttttgattt agagagagat   2580
gtcccagaag atgttgcaca agaaatggta gagtctgggt atgtctgtga aggtgatcac   2640
aagaccatgg ctaaagctat caaagacaga gtatcattaa ttaagaggaa acgagagcag   2700
cggcagttgg tacgggagga gcaagaaaaa aaaaagcagg aagagagcag tctcaaacag   2760
```

```
caggtagaac aatccagtgc ttcccagaca ggaatcaagc agctcccttc tgctagcacc   2820
ggcataccta ctgcttctac cacttcagct tcagtttcta cacaagtaga acctgaagaa   2880
cctgaggcag atcaacatca acaactacag taccagcaac ccagtatatc tgtgttatct   2940
gatgggacgg ttgacagtgg tcagggatcc tctgtcttca cagaatctcg agtgagcagc   3000
caacagacag tttcatatgg ttcccaacat gaacaggcac attctacagg cacagtccca   3060
gggcatatac cttctactgt ccaagcacag tctcagcccc atggggtata tccaccctca   3120
agtgtggcac aggggcagag ccagggtcag ccatcctcaa gtagcttaac aggggtttca   3180
tcttcccaac ccatacaaca tcctcagcag cagcagggaa tacagcagac agcccctcct   3240
caacagacag tgcagtattc actttcacag acatcaacct ccagtgaggc cactactgca   3300
cagccagtga gtcagcctca agctccacaa gtcttgcctc aagtatcagc tggaaaacag   3360
cttccagttt cccagccagt accaactatc caaggcgaac ctcagatccc agttgcgaca   3420
caaccctcgg ttgttccagt ccactctggt gctcatttcc ttccagtggg acagccgctc   3480
cctactccct tgctccctca gtaccctgtc tctcagattc ccatatcaac tcctcatgtg   3540
tctacggctc agacaggttt ctcatccctt cccatcacaa tggcagctgg cattactcag   3600
cctctgctca cgttggcttc atctgctaca acagctgcga tcccgggggt atcaactgtg   3660
gttcctagtc agcttccaac ccttctgcag cctgtgactc agctgccaag tcaggttcac   3720
ccacagctcc tacaaccagc agttcagtcc atgggaatac cagctaacct tggacaagct   3780
gctgaggttc cactttcctc tggagatgtt ctgtaccagg gcttcccacc tcgactgcca   3840
ccacagtacc caggagattc aaatattgct ccctcttcca acgtggcttc tgtttgcatc   3900
cattctacag tcctatcccc tcccatgccg acagaagtac tggctacacc tgggtacttt   3960
cccacagtgg tgcagcctta tgtggaatca aatcttttag ttcctatggg tggtgtagga   4020
ggacaggttc aagtgtccca gccaggaggg agtttagcac aagcccccac tacatcctcc   4080
cagcaagcag ttttggagag tactcaggga gtctctcagg ttgctcctgc agagccagtt   4140
gcagtagcac agacccaagc tacccagccg accactttgg cttcctctgt agacagtgca   4200
cattcagatg ttgcttcagg tatgagtgat ggcaatgaga acgtcccatc ttccagtgga   4260
aggcatgaag gaagaactac aaaacggcat taccgaaaat ctgtaaggag tcgctctcga   4320
catgaaaaaa cttcacgccc aaaattaaga attttgaatg tttcaaataa aggagaccga   4380
gtagtagaat gtcaattaga gactcataat aggaaaatgg ttacattcaa atttgaccta   4440
gatggtgaca accccgagga gatagcaaca attatggtga acaatgactt tattctagca   4500
atagagagag agtcgtttgt ggatcaagtg cgagaaatta ttgaaaaagc tgatgaaatg   4560
ctcagtgagg atgtcagtgt ggaaccagag ggtgatcagg gattggagag tctacaagga   4620
aaggatgact atggcttttc aggttctcag aaattggaag gagagttcaa acaaccaatt   4680
cctgcgtctt ccatgccaca gcaaataggc attcctacca gttctttaac tcaagttgtt   4740
cattctgcgg gaaggcggtt tatagtgagt cctgtgccag aaagccgatt acgagaatca   4800
aaagttttcc ccagtgaaat aacagataca gttgctgcct ctacagctca gagccctgga   4860
atgaacttgt ctcactctgc atcatccctt agtctacaac aggccttttc tgaacttaga   4920
cgtgcccaaa tgacagaagg acccaacaca gcacctccaa actttagtca tacaggacca   4980
acatttccag tagtacctcc tttcttaagt agcattgctg gagtcccaac cacagcagca   5040
gccacagcac cagtccctgc aacaagcagc cctcctaatg acatttccac atcagtaatt   5100
```

-continued

```
cagtctgagg ttacagtgcc cactgaagag gggattgctg gagttgccac cagcacaggt   5160
gtggtaactt caggtggtct ccccatacca cctgtgtctg aatcaccagt actttccagc   5220
gtagtttcaa gtatcacaat acctgcagtt gtctcaatat ctactacatc cccgtcactt   5280
caagtcccca catccacatc tgagatcgtt gtttctagta cagcactgta tccttcagta   5340
acagtttcag caacttcagc ctctgcaggg ggcagtactg ctaccccagg tcctaagcct   5400
ccagctgtag tatctcagca ggcagcaggc agcactactg tgggagccac attaacatca   5460
gtttctacca ccacttcatt cccaagcaca gcttcacagc tgtgcattca gcttagcagc   5520
agtacttcta ctcctacttt agctgaaacc gtggtagtta gcgcacactc actagataag   5580
acatctcata gcagtacaac tggattggct ttctccctct ctgcaccatc ttcctcttcc   5640
tctcctggag caggagtgtc tagttatatt tctcagcctg gtgggctgca tcctttggtc   5700
attccatcag tgatagcttc tactcctatt cttccccaag cagcaggacc tacttctaca   5760
cctttattac cccaagtacc tagtatccca cccttggtac agcctgttgc caatgtgcct   5820
gctgtacagc agacactaat tcatagtcag cctcaaccag ctttgcttcc caaccagccc   5880
catactcatt gtcctgaagt agattctgat acacaaccca aagctcctgg aattgatgac   5940
ataaagactc tagaagaaaa gctgcggtct ctgttcagtg aacacagctc atctggagct   6000
cagcatgcct ctgtctcact ggagacctca ctagtcatag agagcactgt cacaccaggc   6060
atcccaacta ctgctgttgc accaagcaaa ctcctgactt ctaccacaag tacttgctta   6120
ccaccaacca atttaccact aggaacagtt gctttgccag ttacaccagt ggtcacacct   6180
gggcaagttt ctaccccagt cagcactact acatcaggag tgaaacctgg aactgctccc   6240
tccaagccac ctctaactaa ggctccggtg ctgccagtgg gtactgaact tccagcaggt   6300
actctaccca gcgagcagct gccacctttt ccaggacctt ctctaaccca gtcccagcaa   6360
cctctagagg atcttgatgc tcaattgaga agaacactta gtccagagat gatcacagtg   6420
acttctgcgg ttggtcctgt gtccatggcg gctccaacag caatcacaga agcaggaaca   6480
cagcctcaga agggtgtttc tcaagtcaaa gaaggccctg tcctagcaac tagttcagga   6540
gctggtgttt ttaagatggg acgatttcag gtttctgttg cagcagacgg tgcccagaaa   6600
gagggtaaaa ataagtcaga agatgcaaag tctgttcatt ttgaatccag cacctcagag   6660
tcctcagtgc tatcaagtag tagtccagag agtaccttgg tgaaaccaga gccgaatggc   6720
ataaccatcc ctggtatctc ttcagatgtg ccagagagtg cccacaaaac tactgcctca   6780
gaggcaaagt cagacactgg gcagcctacc aaggttggac gttttcaggt gacaactaca   6840
gcaaacaaag tgggtcgttt ctctgtatca aaaactgagg acaagatcac tgacacaaag   6900
aaagaaggac cagtggcatc tcctcctttt atggatttgg aacaagctgt tcttcctgct   6960
gtgataccaa agaaagagaa gcctgaactg tcagagcctt cacatctaaa tgggccgtct   7020
tctgacccgg aggccgcttt tttaagtagg gatgtggatg atggttccgg tagtccacac   7080
tcgccccatc agctgagctc aaagagcctt cctagccaga atctaagtca aagccttagt   7140
aattcattta actcctctta catgagtagc gacaatgagt cagatatcga agatgaagac   7200
ttaaagttag agctgcgacg actacgagat aaacatctca aagagattca ggacctgcag   7260
agtcgccaga agcatgaaat tgaatctttg tataccaaac tgggcaaggt gccccctgct   7320
gttattattc ccccagctgc tccccctttca gggagaagac gacgacccac taaaagcaaa   7380
ggcagcaaat ctagtcgaag cagttccttg gggaataaaa gcccccagct ttcaggtaac   7440
ctgtctggtc agagtgcagc ttcagtcttg cacccccagc agaccctcca ccctcctggc   7500
```

```
aacatcccag agtccgggca gaatcagctg ttacagcccc ttaagccatc tccctccagt   7560
gacaacctct attcagcctt caccagtgat ggtgccattt cagtaccaag cctttctgct   7620
ccaggtcaag gaaccagcag cacaaacact gttggggcaa cagtgaacag ccaagccgcc   7680
caagctcagc ctcctgccat gacgtccagc aggaagggca cattcacaga tgacttgcac   7740
aagttggtag acaattgggc ccgagatgcc atgaatctct caggcaggag aggaagcaaa   7800
gggcacatga attacgaggg ccctggaatg gcaaggaagt tctctgcacc tgggcaactg   7860
tgcatctcca tgacctcgaa cctgggtggc tctgccccca tctctgcagc atcagctacc   7920
tctctaggtc acttcaccaa gtctatgtgc cccccacagc agtatggctt tccagctacc   7980
ccatttggcg ctcaatggag tgggacgggt ggcccagcac cacagccact tggccagttc   8040
caacctgtgg gaactgcctc cttgcagaat ttcaacatca gcaatttgca gaaatccatc   8100
agcaaccccc caggctccaa cctgcggacc acttagacct agagacatta actgaataga   8160
tctgggggca ggagatggaa tgctgagggg gtgggtgggg gtgggaagta gcctatatac   8220
taactactag tgctgcattt aactggttat ttcttgccag aggggaatgt tttaatact    8280
gcattgagcc ctcagaatgg agagtctccc ccgctccagt tattggaatg ggagaggaag   8340
gaaagaacag ctttttttgtc aaggggcagc ttcagaccat gctttcctgt ttatctatac   8400
tcagtaatga ggatgagggc taggaaagtc ttgttcataa ggaagctgga gaactcaatg   8460
taaaatcaaa cccatctgta atttcgagtg ggtggagctc ttgcttttgg tacatgccct   8520
gaatccctca ctccctcaag aatccgaacc acaggacaaa aaccacctac tgggctctct   8580
cctaccctgc cctcctccct ttttttacc cctctctttt ttattttttc tttgctcttt   8640
agaacccagt gaaaaatacc agggtactgg ggtgcaactc tttcttatga taggtcatta   8700
gtgctttaag caaaagatat tagcagcttt gactgcagca ttagcaatta ggaaaaaaaa   8760
aaaattaagt tccctgcgga catgtaactt tgccatcagt tttgatgtgg aaacactgtg   8820
atatataaaa tgttgttgga caacagtagt tttaagagta aaatatgaaa cgtttaaaaa   8880
gttccaaaaa aagctagctc tgtcctttac ttattgagac actttaactt tttcctttgt   8940
atttccattg tattagataa ataaatgtga atgtaaaatt gtataaatta ctgtacttga   9000
atacttctgt ttcccagtgt tgcttgctgg acattttagt gccttggact tctattgctt   9060
ctgccattag catcaactta ccagacccca gatcaataaa gggcatgtgg aaggaaatcg   9120
taggtccatg tgaccccagc agtccagcag tggttatgcc aaagggaaat tgaaaaagta   9180
ttttttttaag tcattcaaca actttgtcta gagcaggtgt aagatgagta gggtgggaag   9240
ttaggttggc atcagtggtt aaaaacagaa agttctgttt cgggaatagt gaggaggggg   9300
tgttgtaaca aaattggaca acttaaaaga atggtgtgtg ctgggtgaaa gacaaagact   9360
aaagaatgag gaaacaaacg tgatgcctgg ccagtgactg tcatataaac ctttcttatt   9420
tgagctaggc ttgaacagac gtgacctaga agaaactgaa cataaagaga agggggtggg   9480
gggctagttt tcaagttggg gaacctgata gtgaaaagtc acagatggag aaaattgctc   9540
tcagaaaaac tgtttggatt gctttcctct tgttgcacat gtaccatgca tttctcagct   9600
tggggtacta cattttgtgg aaagttaatc tatctatctt tccacatctg aattaatcat   9660
tctaggaaag aatacttatt cctactcatt tcctttatga tgtccaaatg gttgcaggat   9720
cataatctat tgtgccacct ttatttctag aagtacaact aatatgttca cattttcaaa   9780
taaataatac tccccgtaag taataactgc aaccaatcag tgttattcag tgctatgcct   9840
```

```
ccttgtaatg ggtagttatt aattattttc agagctttcc ggaaatactg tcctaactgg   9900

ctatgtttag gatctttgtt atctctgaag acaaagaaag aagctaggac tcttaatttt   9960

ggggtgcttc ttgactctta gttgggaaac tgaaaatatt tccaaccttt tacccacgtc  10020

aatggcatat tctgggaatc accaccacca ccaccactac cacagaaaga ggctggaggc  10080

tcctgtaccc tgttcattcc ttaagggccc tgcttccctt agtaagtaag taagttggtc  10140

tacggcccta aatatgcaaa tgagagctga aggtttttaa aaggtagaaa ggaaaagggc  10200

aagggcttcc acccctgctt taaaatgatt tatttattct ctgcttgtat ttcttgtgga  10260

gagagtaagg atagaaccaa caaggggctg agtagctgag aaaggggcca cccaagagtg  10320

aaacatactt tataccagag gagcagtgga gcctcatgca gcacattatc atttgttatt  10380

tgggtttaat aataattttg acatcttttc actcatacac aaaaaaagtc agaactggtg  10440

ttatttactg ttgatttcat cctcctgtgt atgaaataac aagcctagag gaatgaacta  10500

gtgctactga actgtttaaa ttatttttgt gttaatagta cactttgagt atctttttcc  10560

acattaaaaa ctttctgaat tataaatgtt ttccttacat tatttaacaa tgtacactgt  10620

taaaaataaa aataaaaatt caaactttgg gggtttctca gcagccgtta attgtacatt  10680

ttgcactaac tctgggtgtt gcgcttcttg taagattgcg ctttgtgctt cagtttgtta  10740

cctttgtaga cttatttaat gaaaccattc aaataaacca aacttgcttt tgttga      10796
```

<210> SEQ ID NO 54
<211> LENGTH: 29
<212> TYPE: DNA
<213> ORGANISM: Artificial Sequence
<220> FEATURE:
<223> OTHER INFORMATION: A synthetic oligonucleotide sequence

<400> SEQUENCE: 54

```
acgttggatg ttcatgcggc ccccacact                                      29
```

<210> SEQ ID NO 55
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 55

```
acgttggatg gagacttcca aagttgtgcg                                     30
```

<210> SEQ ID NO 56
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 56

```
acgttggatg ccccatgtgt gctatcaaaa                                     30
```

<210> SEQ ID NO 57
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 57

```
acgttggatg attccccttc cattcccaac                                     30
```

<210> SEQ ID NO 58
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 58
acgttggatg tactcagtag tattgctacc 30

<210> SEQ ID NO 59
<211> LENGTH: 31
<212> TYPE: DNA
<213> ORGANISM: Artificial Sequence
<220> FEATURE:
<223> OTHER INFORMATION: A synthetic oligonucleotide sequence

<400> SEQUENCE: 59
acgttggatg cttatattga taggcaatga g 31

<210> SEQ ID NO 60
<211> LENGTH: 28
<212> TYPE: DNA
<213> ORGANISM: Artificial Sequence
<220> FEATURE:
<223> OTHER INFORMATION: A synthetic oligonucleotide sequence

<400> SEQUENCE: 60
acgttggatg gtgggtgatg ggcagaag 28

<210> SEQ ID NO 61
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 61
acgttggatg ctgcagagac tcctcggtct 30

<210> SEQ ID NO 62
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 62
acgttggatg caccttagtc ttcgacttgg 30

<210> SEQ ID NO 63
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 63
acgttggatg acaagatggc tgaactctgg 30

<210> SEQ ID NO 64
<211> LENGTH: 30
<212> TYPE: DNA
<213> ORGANISM: Artificial Sequence
<220> FEATURE:

<223> OTHER INFORMATION: A synthetic oligonucleotide sequence

<400> SEQUENCE: 64
acgttggatg cgaacttggc aatggctgtg 30

<210> SEQ ID NO 65
<211> LENGTH: 29
<212> TYPE: DNA
<213> ORGANISM: Artificial Sequence
<220> FEATURE:
<223> OTHER INFORMATION: A synthetic oligonucleotide sequence

<400> SEQUENCE: 65
acgttggatg agcgccttct tgctggcac 29

<210> SEQ ID NO 66
<211> LENGTH: 33
<212> TYPE: DNA
<213> ORGANISM: Artificial Sequence
<220> FEATURE:
<223> OTHER INFORMATION: A synthetic oligonucleotide sequence

<400> SEQUENCE: 66
acgttggatg tgagttgttc agccttagca gca 33

<210> SEQ ID NO 67
<211> LENGTH: 32
<212> TYPE: DNA
<213> ORGANISM: Artificial Sequence
<220> FEATURE:
<223> OTHER INFORMATION: A synthetic oligonucleotide sequence

<400> SEQUENCE: 67
acgttggatg cctaggttac aatttcagga ag 32

<210> SEQ ID NO 68
<211> LENGTH: 28
<212> TYPE: DNA
<213> ORGANISM: Artificial Sequence
<220> FEATURE:
<223> OTHER INFORMATION: A synthetic oligonucleotide sequence

<400> SEQUENCE: 68
acgttggatg cctcgttgct gcctcccg 28

<210> SEQ ID NO 69
<211> LENGTH: 29
<212> TYPE: DNA
<213> ORGANISM: Artificial Sequence
<220> FEATURE:
<223> OTHER INFORMATION: A synthetic oligonucleotide sequence

<400> SEQUENCE: 69
acgttggatg atgagcgcca tcagcagac 29

<210> SEQ ID NO 70
<211> LENGTH: 29
<212> TYPE: DNA
<213> ORGANISM: Artificial Sequence
<220> FEATURE:
<223> OTHER INFORMATION: A synthetic oligonucleotide sequence

<400> SEQUENCE: 70
acgttggatg ttggactccc actccatgc 29

<210> SEQ ID NO 71
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 71
acgttggatg cccatcgtgg accccattaa 30

<210> SEQ ID NO 72
<211> LENGTH: 29
<212> TYPE: DNA
<213> ORGANISM: Artificial Sequence
<220> FEATURE:
<223> OTHER INFORMATION: A synthetic oligonucleotide sequence

<400> SEQUENCE: 72
acgttggatg aggcttattg tggcaagac 29

<210> SEQ ID NO 73
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 73
acgttggatg gtgaaagatg caagcacctg 30

<210> SEQ ID NO 74
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 74
acgttggatg tcaaccccat catctactgc 30

<210> SEQ ID NO 75
<211> LENGTH: 29
<212> TYPE: DNA
<213> ORGANISM: Artificial Sequence
<220> FEATURE:
<223> OTHER INFORMATION: A synthetic oligonucleotide sequence

<400> SEQUENCE: 75
acgttggatg ggtctccgtg ggtcgcgtg 29

<210> SEQ ID NO 76
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 76
acgttggatg gattgacagg ttcatgcagg 30

<210> SEQ ID NO 77
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 77
acgttggatg tggacgtagg tgttgaaagc 30

<210> SEQ ID NO 78
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 78
acgttggatg gcaaccatca cagtactaag 30

<210> SEQ ID NO 79
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 79
acgttggatg cacaactgga agagttgagg 30

<210> SEQ ID NO 80
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 80
acgttggatg tccctctcca gccttgacag 30

<210> SEQ ID NO 81
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 81
acgttggatg aacctctcct tccctctcag 30

<210> SEQ ID NO 82
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 82
acgttggatg acaggctacc tggctttaac 30

<210> SEQ ID NO 83
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 83
acgttggatg ggaatccagg agaataggtc 30

<210> SEQ ID NO 84
<211> LENGTH: 31

<212> TYPE: DNA
<213> ORGANISM: Artificial Sequence
<220> FEATURE:
<223> OTHER INFORMATION: A synthetic oligonucleotide sequence

<400> SEQUENCE: 84
acgttggatg agaagcctgc accatgtttt g 31

<210> SEQ ID NO 85
<211> LENGTH: 31
<212> TYPE: DNA
<213> ORGANISM: Artificial Sequence
<220> FEATURE:
<223> OTHER INFORMATION: A synthetic oligonucleotide sequence

<400> SEQUENCE: 85
acgttggatg cagtccacat aatgcatttt c 31

<210> SEQ ID NO 86
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 86
acgttggatg atgagagaca tgacgatgcc 30

<210> SEQ ID NO 87
<211> LENGTH: 29
<212> TYPE: DNA
<213> ORGANISM: Artificial Sequence
<220> FEATURE:
<223> OTHER INFORMATION: A synthetic oligonucleotide sequence

<400> SEQUENCE: 87
acgttggatg agcgccttct tgctggcac 29

<210> SEQ ID NO 88
<211> LENGTH: 31
<212> TYPE: DNA
<213> ORGANISM: Artificial Sequence
<220> FEATURE:
<223> OTHER INFORMATION: A synthetic oligonucleotide sequence

<400> SEQUENCE: 88
acgttggatg gtttttcagt tcctgaattt g 31

<210> SEQ ID NO 89
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 89
acgttggatg gaaacagtga cagccaaatg 30

<210> SEQ ID NO 90
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 90

-continued acgttggatg tgtagtaccc agaacaacgg 30

<210> SEQ ID NO 91
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 91
acgttggatg agcctgggaa cagctccatc 30

<210> SEQ ID NO 92
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 92
acgttggact ggagaccact cccatccttt 30

<210> SEQ ID NO 93
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 93
acgttgatgt ggccatcaca ttcgtcagat 30

<210> SEQ ID NO 94
<211> LENGTH: 30
<212> TYPE: DNA
<213> ORGANISM: Artificial Sequence
<220> FEATURE:
<223> OTHER INFORMATION: A synthetic oligonucleotide sequence

<400> SEQUENCE: 94
acgttgattg agaccatccc ggctaaaacg 30

<210> SEQ ID NO 95
<211> LENGTH: 15
<212> TYPE: DNA
<213> ORGANISM: Artificial Sequence
<220> FEATURE:
<223> OTHER INFORMATION: A synthetic oligonucleotide sequence

<400> SEQUENCE: 95
cgccgccgcc gtccc 15

<210> SEQ ID NO 96
<211> LENGTH: 16
<212> TYPE: DNA
<213> ORGANISM: Artificial Sequence
<220> FEATURE:
<223> OTHER INFORMATION: A synthetic oligonucleotide sequence

<400> SEQUENCE: 96
cgccgccgcc gtcccc 16

<210> SEQ ID NO 97
<211> LENGTH: 16
<212> TYPE: DNA
<213> ORGANISM: Artificial Sequence
<220> FEATURE:
<223> OTHER INFORMATION: A synthetic oligonucleotide sequence

<400> SEQUENCE: 97
cgccgccgcc gtcccg 16

<210> SEQ ID NO 98
<211> LENGTH: 18
<212> TYPE: DNA
<213> ORGANISM: Artificial Sequence
<220> FEATURE:
<223> OTHER INFORMATION: A synthetic oligonucleotide sequence

<400> SEQUENCE: 98
gcccttagca tttttctt 18

<210> SEQ ID NO 99
<211> LENGTH: 19
<212> TYPE: DNA
<213> ORGANISM: Artificial Sequence
<220> FEATURE:
<223> OTHER INFORMATION: A synthetic oligonucleotide sequence

<400> SEQUENCE: 99
gcccttagca tttttcttc 19

<210> SEQ ID NO 100
<211> LENGTH: 19
<212> TYPE: DNA
<213> ORGANISM: Artificial Sequence
<220> FEATURE:
<223> OTHER INFORMATION: A synthetic oligonucleotide sequence

<400> SEQUENCE: 100
gcccttagca tttttcttt 19

<210> SEQ ID NO 101
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 101
ctttacctat gattcagtct ta 22

<210> SEQ ID NO 102
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 102
ctttacctat gattcagtct tac 23

<210> SEQ ID NO 103
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 103
ctttacctat gattcagtct tag 23

<210> SEQ ID NO 104
<211> LENGTH: 17
<212> TYPE: DNA
<213> ORGANISM: Artificial Sequence
<220> FEATURE:
<223> OTHER INFORMATION: A synthetic oligonucleotide sequence

<400> SEQUENCE: 104
cgcatctccc accccca 17

<210> SEQ ID NO 105
<211> LENGTH: 18
<212> TYPE: DNA
<213> ORGANISM: Artificial Sequence
<220> FEATURE:
<223> OTHER INFORMATION: A synthetic oligonucleotide sequence

<400> SEQUENCE: 105
cgcatctccc acccccaa 18

<210> SEQ ID NO 106
<211> LENGTH: 18
<212> TYPE: DNA
<213> ORGANISM: Artificial Sequence
<220> FEATURE:
<223> OTHER INFORMATION: A synthetic oligonucleotide sequence

<400> SEQUENCE: 106
cgcatctccc acccccag 18

<210> SEQ ID NO 107
<211> LENGTH: 17
<212> TYPE: DNA
<213> ORGANISM: Artificial Sequence
<220> FEATURE:
<223> OTHER INFORMATION: A synthetic oligonucleotide sequence

<400> SEQUENCE: 107
actgcttcca ttctgcc 17

<210> SEQ ID NO 108
<211> LENGTH: 18
<212> TYPE: DNA
<213> ORGANISM: Artificial Sequence
<220> FEATURE:
<223> OTHER INFORMATION: A synthetic oligonucleotide sequence

<400> SEQUENCE: 108
actgcttcca ttctgccc 18

<210> SEQ ID NO 109
<211> LENGTH: 18
<212> TYPE: DNA
<213> ORGANISM: Artificial Sequence
<220> FEATURE:
<223> OTHER INFORMATION: A synthetic oligonucleotide sequence

<400> SEQUENCE: 109
actgcttcca ttctgcca 18

<210> SEQ ID NO 110
<211> LENGTH: 17
<212> TYPE: DNA
<213> ORGANISM: Artificial Sequence
<220> FEATURE:
<223> OTHER INFORMATION: A synthetic oligonucleotide sequence

<400> SEQUENCE: 110
gtccggcgca tggcttc 17

<210> SEQ ID NO 111
<211> LENGTH: 18
<212> TYPE: DNA
<213> ORGANISM: Artificial Sequence
<220> FEATURE:
<223> OTHER INFORMATION: A synthetic oligonucleotide sequence

<400> SEQUENCE: 111
gtccggcgca tggcttcc 18

<210> SEQ ID NO 112
<211> LENGTH: 18
<212> TYPE: DNA
<213> ORGANISM: Artificial Sequence
<220> FEATURE:
<223> OTHER INFORMATION: A synthetic oligonucleotide sequence

<400> SEQUENCE: 112
gtccggcgca tggcttct 18

<210> SEQ ID NO 113
<211> LENGTH: 18
<212> TYPE: DNA
<213> ORGANISM: Artificial Sequence
<220> FEATURE:
<223> OTHER INFORMATION: A synthetic oligonucleotide sequence

<400> SEQUENCE: 113
attcccagtt catcctct 18

<210> SEQ ID NO 114
<211> LENGTH: 19
<212> TYPE: DNA
<213> ORGANISM: Artificial Sequence
<220> FEATURE:
<223> OTHER INFORMATION: A synthetic oligonucleotide sequence

<400> SEQUENCE: 114
attcccagtt catcctctc 19

<210> SEQ ID NO 115
<211> LENGTH: 19
<212> TYPE: DNA
<213> ORGANISM: Artificial Sequence
<220> FEATURE:
<223> OTHER INFORMATION: A synthetic oligonucleotide sequence

<400> SEQUENCE: 115
attcccagtt catcctctt 19

<210> SEQ ID NO 116
<211> LENGTH: 19
<212> TYPE: DNA
<213> ORGANISM: Artificial Sequence
<220> FEATURE:
<223> OTHER INFORMATION: A synthetic oligonucleotide sequence

<400> SEQUENCE: 116
gctgcctccc gccagcgaa 19

<210> SEQ ID NO 117

<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 117
gctgcctccc gccagcgaaa 20

<210> SEQ ID NO 118
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 118
gctgcctccc gccagcgaag 20

<210> SEQ ID NO 119
<211> LENGTH: 19
<212> TYPE: DNA
<213> ORGANISM: Artificial Sequence
<220> FEATURE:
<223> OTHER INFORMATION: A synthetic oligonucleotide sequence

<400> SEQUENCE: 119
cacagtgacc gagaccacg 19

<210> SEQ ID NO 120
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 120
cacagtgacc gagaccacgc 20

<210> SEQ ID NO 121
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 121
cacagtgacc gagaccacgg 20

<210> SEQ ID NO 122
<211> LENGTH: 19
<212> TYPE: DNA
<213> ORGANISM: Artificial Sequence
<220> FEATURE:
<223> OTHER INFORMATION: A synthetic oligonucleotide sequence

<400> SEQUENCE: 122
gggagaaata accagctat 19

<210> SEQ ID NO 123
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 123
gggagaaata accagctatg 20

<210> SEQ ID NO 124
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 124
gggagaaata accagctatt 20

<210> SEQ ID NO 125
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 125
aattccgcaa ggccttccag 20

<210> SEQ ID NO 126
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 126
aattccgcaa ggccttccag c 21

<210> SEQ ID NO 127
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 127
aattccgcaa ggccttccag g 21

<210> SEQ ID NO 128
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 128
gaagactggc tgctccctga 20

<210> SEQ ID NO 129
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 129
gaagactggc tgctccctga c 21

<210> SEQ ID NO 130
<211> LENGTH: 21
<212> TYPE: DNA

<213> ORGANISM: Artificial Sequence
<220> FEATURE:
<223> OTHER INFORMATION: A synthetic oligonucleotide sequence

<400> SEQUENCE: 130
gaagactggc tgctccctga t 21

<210> SEQ ID NO 131
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 131
tcctccaaaa aaaaagaaaa c 21

<210> SEQ ID NO 132
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 132
tcctccaaaa aaaaagaaaa cc 22

<210> SEQ ID NO 133
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 133
tcctccaaaa aaaaagaaaa ct 22

<210> SEQ ID NO 134
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 134
gctgcagggg ccagttcctc c 21

<210> SEQ ID NO 135
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 135
gctgcagggg ccagttcctc ca 22

<210> SEQ ID NO 136
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 136
gctgcagggg ccagttcctc cg 22

<210> SEQ ID NO 137
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 137
ggacaaagca ggcttaatct g 21

<210> SEQ ID NO 138
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 138
ggacaaagca ggcttaatct ga 22

<210> SEQ ID NO 139
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 139
ggacaaagca ggcttaatct gg 22

<210> SEQ ID NO 140
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 140
cacttcccac taccaaatga gc 22

<210> SEQ ID NO 141
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 141
cacttcccac taccaaatga gcc 23

<210> SEQ ID NO 142
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 142
cacttcccac taccaaatga gca 23

<210> SEQ ID NO 143
<211> LENGTH: 23
<212> TYPE: DNA
<213> ORGANISM: Artificial Sequence
<220> FEATURE:

<223> OTHER INFORMATION: A synthetic oligonucleotide sequence

<400> SEQUENCE: 143
taccacccac acctcgtccc ttt 23

<210> SEQ ID NO 144
<211> LENGTH: 24
<212> TYPE: DNA
<213> ORGANISM: Artificial Sequence
<220> FEATURE:
<223> OTHER INFORMATION: A synthetic oligonucleotide sequence

<400> SEQUENCE: 144
taccacccac acctcgtccc tttc 24

<210> SEQ ID NO 145
<211> LENGTH: 24
<212> TYPE: DNA
<213> ORGANISM: Artificial Sequence
<220> FEATURE:
<223> OTHER INFORMATION: A synthetic oligonucleotide sequence

<400> SEQUENCE: 145
taccacccac acctcgtccc tttg 24

<210> SEQ ID NO 146
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 146
actgatattc tctatttgtt gag 23

<210> SEQ ID NO 147
<211> LENGTH: 24
<212> TYPE: DNA
<213> ORGANISM: Artificial Sequence
<220> FEATURE:
<223> OTHER INFORMATION: A synthetic oligonucleotide sequence

<400> SEQUENCE: 147
actgatattc tctatttgtt gagc 24

<210> SEQ ID NO 148
<211> LENGTH: 24
<212> TYPE: DNA
<213> ORGANISM: Artificial Sequence
<220> FEATURE:
<223> OTHER INFORMATION: A synthetic oligonucleotide sequence

<400> SEQUENCE: 148
actgatattc tctatttgtt gagg 24

<210> SEQ ID NO 149
<211> LENGTH: 24
<212> TYPE: DNA
<213> ORGANISM: Artificial Sequence
<220> FEATURE:
<223> OTHER INFORMATION: A synthetic oligonucleotide sequence

<400> SEQUENCE: 149
ccgaacaacg gcagcttctt cccc 24

```
<210> SEQ ID NO 150
<211> LENGTH: 25
<212> TYPE: DNA
<213> ORGANISM: Artificial Sequence
<220> FEATURE:
<223> OTHER INFORMATION: A synthetic oligonucleotide sequence

<400> SEQUENCE: 150

ccgaacaacg gcagcttctt ccccc                                    25

<210> SEQ ID NO 151
<211> LENGTH: 25
<212> TYPE: DNA
<213> ORGANISM: Artificial Sequence
<220> FEATURE:
<223> OTHER INFORMATION: A synthetic oligonucleotide sequence

<400> SEQUENCE: 151

ccgaacaacg gcagcttctt cccct                                    25

<210> SEQ ID NO 152
<211> LENGTH: 26
<212> TYPE: DNA
<213> ORGANISM: Artificial Sequence
<220> FEATURE:
<223> OTHER INFORMATION: A synthetic oligonucleotide sequence

<400> SEQUENCE: 152

gacctgctgc ctatacagtc actttt                                   26

<210> SEQ ID NO 153
<211> LENGTH: 27
<212> TYPE: DNA
<213> ORGANISM: Artificial Sequence
<220> FEATURE:
<223> OTHER INFORMATION: A synthetic oligonucleotide sequence

<400> SEQUENCE: 153

gacctgctgc ctatacagtc actttta                                  27

<210> SEQ ID NO 154
<211> LENGTH: 27
<212> TYPE: DNA
<213> ORGANISM: Artificial Sequence
<220> FEATURE:
<223> OTHER INFORMATION: A synthetic oligonucleotide sequence

<400> SEQUENCE: 154

gacctgctgc ctatacagtc acttttt                                  27

<210> SEQ ID NO 155
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 155

cccatttctc tagacctgct                                          20

<210> SEQ ID NO 156
<211> LENGTH: 20
<212> TYPE: DNA
<213> ORGANISM: Artificial Sequence
<220> FEATURE:
<223> OTHER INFORMATION: A synthetic oligonucleotide sequence
```

-continued

```
<400> SEQUENCE: 156

gggatggtgt ctcgtacata                                              20
```